(12) United States Patent
Yoo et al.

(10) Patent No.: US 12,059,474 B2
(45) Date of Patent: Aug. 13, 2024

(54) METHODS FOR SELECTING ANTIBODIES THAT SPECIFICALLY BIND GLYCOSYLATED IMMUNE CHECKPOINT PROTEINS

(71) Applicants: STCUBE & CO., INC., Seoul (KR); BOARD OF REGENTS, THE UNIVERSITY OF TEXAS SYSTEM, Austin, TX (US)

(72) Inventors: Stephen S. Yoo, Centreville, VA (US); Mien-Chie Hung, Houston, TX (US)

(73) Assignees: STCUBE & CO., INC., Seoul (KR); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 1377 days.

(21) Appl. No.: 16/086,574

(22) PCT Filed: Mar. 24, 2017

(86) PCT No.: PCT/US2017/024024
§ 371 (c)(1),
(2) Date: Sep. 19, 2018

(87) PCT Pub. No.: WO2017/172517
PCT Pub. Date: Oct. 5, 2017

(65) Prior Publication Data
US 2019/0105403 A1    Apr. 11, 2019

Related U.S. Application Data

(60) Provisional application No. 62/314,940, filed on Mar. 29, 2016, provisional application No. 62/361,298, filed on Jul. 12, 2016.

(51) Int. Cl.
| | |
|---|---|
| *A61K 47/68* | (2017.01) |
| *A01K 67/0278* | (2024.01) |
| *C07K 16/00* | (2006.01) |
| *C07K 16/28* | (2006.01) |
| *C07K 16/30* | (2006.01) |
| *C12N 15/10* | (2006.01) |
| *G01N 33/563* | (2006.01) |

(52) U.S. Cl.
CPC ...... *A61K 47/6849* (2017.08); *A01K 67/0278* (2013.01); *A61K 47/6803* (2017.08); *A61K 47/6855* (2017.08); *C07K 16/00* (2013.01); *C07K 16/2827* (2013.01); *C07K 16/3015* (2013.01); *C12N 15/1037* (2013.01); *G01N 33/563* (2013.01); *A01K 2217/206* (2013.01); *A01K 2227/105* (2013.01); *A01K 2267/0331* (2013.01); *C07K 2317/30* (2013.01); *C07K 2317/73* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 8,354,509 | B2 | 1/2013 | Carven et al. |
| 9,845,361 | B2 * | 12/2017 | Goletz ................. A61P 35/00 |
| 10,836,827 | B2 | 11/2020 | Yoo et al. |
| 2003/0148406 | A1 | 8/2003 | King et al. |
| 2003/0158162 | A1 | 8/2003 | Aiken |
| 2005/0281815 | A1 | 12/2005 | Eshel et al. |
| 2008/0118978 | A1 | 5/2008 | Sato et al. |
| 2008/0187954 | A1 | 8/2008 | Kallmeier et al. |
| 2009/0041783 | A1 | 2/2009 | Takayama et al. |
| 2009/0176317 | A1 | 7/2009 | Kwon et al. |
| 2010/0285039 | A1 * | 11/2010 | Chen .................... A61P 37/04 514/18.9 |

(Continued)

FOREIGN PATENT DOCUMENTS

| | | |
|---|---|---|
| CN | 102321923 A | 1/2012 |
| JP | 2006340714 A | 12/2006 |

(Continued)

OTHER PUBLICATIONS

Hamilton et al. (Infection and immunity, vol. 60, No. Jan. 1, 1992 pp. 143-149). (Year: 1992).*
Jacob Plieth et al.: 11 PD-I / PD-LI Combination Therapies 11, Sep. 8, 2015 (Sep. 18, 2015), XP055404205, Retrieved from the Internet: URL:nfo.evaluategroup.com/rs/607-YGS-364/i, mages/epv-pdct17.pdf [retrieved on Sep. 6, 2017].
M36239, GenBank Accession No. M36239, "Mouse Ig Kappa-chain mRNA V region, partial cds, from hybridoma H147-25H1VK," Apr. 27, 1993, retrieved on Jun. 9, 2016, http://www.ncbi.nlm.nih.gov/nuccore/M36239.

(Continued)

*Primary Examiner* — Meera Natarajan
(74) *Attorney, Agent, or Firm* — Ballard Spahr LLP

(57) ABSTRACT

Methods for producing and screening for antibodies that specifically bind to glycosylated immune checkpoint proteins (ICPs) relative to non-glycosylated ICPs are provided. Such antibodies recognize specific epitopes of glycosylated ICPs and can prevent or block the binding of a glycosylated ICP with its ligand, such as another ICP, and can inhibit the interactions between the two proteins that can lead to immunosuppression, as exemplified by the human PD-L1/PD-1 interaction. By way of specific example, human PD-L1 and PD-1 polypeptides comprising glycosylated amino acid residues within their extracellular domains are provided for generating anti-glycosylated PD-L1 or anti-glycosylated PD-1 antibodies that specifically bind PD-L1 or PD-1, respectively, and inhibit the PD-L1/PD-1 interaction. The antibodies produced and selected by the methods are especially useful as cancer therapeutics for disrupting, blocking, or neutralizing the ICP system and specific ICP interactions therein.

22 Claims, 15 Drawing Sheets
Specification includes a Sequence Listing.

(56) References Cited

U.S. PATENT DOCUMENTS

| | | | |
|---|---|---|---|
| 2011/0271358 | A1 | 11/2011 | Freeman et al. |
| 2012/0034229 | A1 | 2/2012 | Rousselle et al. |
| 2013/0017251 | A1 | 1/2013 | Huang et al. |
| 2014/0056902 | A1 | 2/2014 | Shimizu et al. |
| 2014/0170134 | A1 | 6/2014 | Schneewind et al. |
| 2016/0376367 | A1 | 12/2016 | Yuan et al. |
| 2017/0106065 | A1 | 4/2017 | Foy et al. |
| 2017/0247454 | A1 | 8/2017 | Benz et al. |
| 2018/0118830 | A1 | 5/2018 | Yoo |

FOREIGN PATENT DOCUMENTS

| | | | |
|---|---|---|---|
| JP | 2018512175 A | | 5/2018 |
| JP | 2019509976 A | | 4/2019 |
| WO | WO 2006/004988 | | 1/2006 |
| WO | WO 2006/121168 | | 11/2006 |
| WO | WO 2008/156712 | | 12/2008 |
| WO | WO 2011/066389 | | 6/2011 |
| WO | 2013063395 A1 | | 5/2013 |
| WO | WO 2013/079174 | | 6/2013 |
| WO | 2013181634 | | 12/2013 |
| WO | WO 2014/055897 A2 | | 4/2014 |
| WO | WO 2014/055897 A3 | | 4/2014 |
| WO | WO 2015/035606 | | 3/2015 |
| WO | WO 2015/061668 | | 4/2015 |
| WO | WO 2015/095418 | | 6/2015 |
| WO | WO 2015/112800 | | 7/2015 |
| WO | WO 2016/160792 | | 10/2016 |
| WO | WO 2017/055443 | | 4/2017 |
| WO | 2017096051 | | 6/2017 |
| WO | WO2017/055443 | * | 6/2017 |

OTHER PUBLICATIONS

DQ372788, GenBank Accession No. DQ372788, "Mus Muculus clone AiDWTimmB-27 immunoglobulin kappa light chain mRNA, partial cds," Feb. 2, 2006, retrieved on Jun. 9, 2016, http://www.ncbi.nlm.nih.gov/nuccore/DQ372788.
Wang, C et al., In Vitro Characterization of the Anti-PD-1 Antibody Nivolumab, BMS-936558, and In Vivo Toxicology in Non-Human Primates. Cancer Immunology Research. May 28, 2014; vol. 2, No. 9; pp. 846-856; p. 848, col. 2, paragraph 4; DOI: 10.1158/2326-6066.CIR-14-0040.
Jeffries, R, Glycosylation as a Strategy to Improve Antibody-Based Therapeutics. Nature Reviews Drug Dlscovt1ry. M<trdr, 2009, Vul. 8, Nu. 3; pp. 220-234; p. 229, col. 1, paragraph 4—p. 229, col. 2, paragraph 1; DOI: 10.1038/nrd2804.
Warrington, Arthur E et al: 1-39 11 Neuron-binding human monoclonal antibodies support central nervous system neurite extension 11, Journal of Neuropathology and Experimental Neurol, Lippincott Williams and Wilkins, New York, NY, vol. 63, No. 5, May 1, 2004 (May 1, 2004), pp. 461-473.
A J Hamilton et al: "A 34-to 38-Kilodalton Cryptococcus neoformans Glycoprotein Produced as an Exoantigen Bearing a Glycosylated Species-Specific Epitope 11", Infection and Immunity, vol. 60. No. 1 • Jan. 1, 1992 (Jan. 1, 1992). pp. 143-149.
Antje Danielczyk et al: 11 PankOMab: a potent new generation anti-tumour MUCI antibody 11 • Cancer Immunology, Immunotherapy, Springer, Berlin, DE, vol. 55, No. 11, Feb. 17, 2006 (Feb. 17, 2006). pp. 1337-1347.
Hertzog et al: 11 Oncofetal expression of the human intestinal mucin glycoprotein antigens in gastrointestinal epithelium defined by monoclonal antibodies. 11, International Journal of Cancer May 30, 1991. vol. 48, No. 3, May 30, 1991 (May 30, 1991), pp. 355-363.
US National Library of Medicine (NLM), Bethesda, MD, US; Nov. 2011 (Nov. 2011).Zhou Ying et al: 11 [Preparation and characterization of three novel monoclonal antibodies against human PD-LI]. 11 , XP002770553, Database accession No. NLM22078450, abstract & Zhou Ying et al: 11 [Preparation and characterization of three novel monoclonal antibodies against human PD-LI]. 11, Xi Bao Yu Fen Zi Mian Yi Xue Za Zhi =Chinese Journal of Cellular and Molecular Immunology Nov. 2011, vol. 27, No. 11, Nov. 2011 pp. 1208-1211.
Maria-Luisa Del Rio, et al: "Antibody-mediated signaling through PD-1 costimulates T cells and enhances CD28-dependent proliferation", European Journal of Immunology, vol. 35, No. 12, Dec. 1, 2005, pp. 3545-3560.
K. M. Mahoney et al: "PD-LI Antibodies to Its Cytoplasmic Domain Most Clearly Delineate Cell Membranes in Immunohistochemical Staining of Tumor Cells", Cancer Immunology Research, vol. 3 , No. 12, Dec. 1, 2015 (Dec. 1, 2015), pp. 1308-1315.
J W Kim et al: "Prospects for Targeting PD-1 and PD-LI in Various Tumor Types", Oncology (Norwalk), vol. 28, No. Suppl. 3, Nov. 10, 2014 (Nov. 10, 2014), pp. 15-28.
Chia-Wei Li et al: "Glycosylation and stabilization of prograrnned death ligand-1 suppresses T-cell activity", Nature Communications, vol. 7, Aug. 30, 2016 (Aug. 30, 2016), p. 12632.
Gang Hao et al., "Epitope characterization of an anti-PD-L 1 antibody using orthogonal approaches", J. Mal. Recagnit. 2015; 28: pp. 269-276.
Taube, et al. "Colocalization of Inflammatory Response with B-7H1 Expression in Human Melanocytic Lesions Supports an Adaptive Resistance Mechanism of Immune Escape" Sci. Trasnl. Med., 2012, vol. 4, No. 127, p. 127.
Leighton JK. Center for Drug Evaluation and Research. Application No. 1255540rig1s000. OPDIVO nivolumab) https://www.accessdata.fda.gov/drugsatfda docs/nda/2014/1255540rig1s000SunnR.pdf, Dec. 4, 2014) (Year: 2014).
Chia-Wei Li et al: "Supplemental Information: Research Conducted at Asia University Has Provided New Information about Breast Cancer (Eradication of Triple-Negative Breast Cancer Cells by Targeting Glycosylated PD-L1)", Obesity, Fitness & Wellness Week, Mar. 17, 2018, pp. 1-19.
Salatino, et al. "Glycans Pave the Way for Immunotherapy in Triple_Negative Breat Cancer", Cancer Cell, vol. 33, No. 2, Feb. 1, 2018 pp. 155-157.
Sun, et al. "Targeting glycosylated PD-1 induces potent anti-tumor immunity", Cancer Res. Jun. 1, 2020, 80 (11) 2298-2310.
Smith, et al. "BTN1A1, the Mammary Gland butyrophilin, and BTN2A2 Are Both Inhibitors of T Cell Activation", The Journal of Immunology, vol. 184, No. 7, Apr. 1, 2010.
Banghart, et al., "Butyrophilin Is Expressed in Mammary Epithelial Cells from a Single-sized Messenger RNA as a Type I Membrane Glycoprotein", Journal of Biological Chemistry, vol. 273, No. 7, Feb. 13, 1998.
Taylor, et al. "Cloning and sequence analysis of human butyrophilin reveals a potential receptor function", Biochimica et Biophysica Acta Gene Structure and Expression, vol. 1306, No. 1, Apr. 10, 1996.
Swaika Abhisek et al, Current state of anti-PD-L1 and anti-PD-1 agents in cancer therapy, Molecular Immunology, vol. 67, No. 2, Mar. 5, 2015.
Strom and Suthanthiran, Therapeutic Approach to Organ Transplantation. Nephrol Dial Transplant (1996) 11:1176-1181 (Year 1996).
Mokhtari et al., Combination of Carbonic Anhydrase Inhibitor, Acetazolamide, and Sulforaphane, Reduces the Viability and Growth of Bronchial Carcinoid Cell Lines. BMC Cancer, 2013; 13:378, Year 2013.
Supplementary European Search Report issued for EP Patent Application No. EP 16871487 on Apr. 18, 2019, 12 pages.
Yan G. Ni et al., "Development and Fit-for-Purpose Validation of a Soluble Human Programmed Death-1 Protein Assay", The AAPS Journal, vol. 17, No. 4, May 1, 2015 (May 1, 2015), pp. 976-987.
Eszter Lazar-Molnar "Crystal structure of the complex between programmed death-1 (PD-1) and its ligand PD-L2", Proceedings of the National Academy of Sciences of the United States of America, vol. 105, No. 30, Jul. 18, 2008 (Jul. 18, 2008), pp. 10483-10488.
Brown et al. Tolerance of single, but not multiple, amino acid replacements in antibody VH CDR 2: a means of minimizing B cell wastage from somatic hypermutation? J Immunol. May 1, 1996; 156(9):3285-91. (Year: 1996).

(56) References Cited

OTHER PUBLICATIONS

Vajdos et al. Comprehensive functional maps of the antigen-binding site of an anti-ErbB2 antibody obtained with shotgun scanning mutagenesis. J. Mol. Biol. Jul. 5, 2002, 320(2):415-28. (Year: 2002).

Morales-Betanzos et al. Quantitative Mass Spectrometry Analysis of PD-L 1 Protein Expression, N-glycosylation and Expression Stoichiometry with PD-1 and PD-L2 in Human Melanoma. Molecular & Cellular Proteomics 16: 10.107 4/mcp. RA 117.000037, 1705-1717, 2017. (Year: 2017).

U.S. Appl. No. 15/778,663, filed May 24, 2018, Stephen S. Yoo.
U.S. Appl. No. 15/559,513, filed Sep. 19, 2017, Stephen S. Yoo.
U.S. Appl. No. 16/086,582, filed Sep. 19, 2018, Stephen S. Yoo.
U.S. Appl. No. 16/318,840, filed Jan. 18, 2019, Stephen S. Yoo.

David Yin-wei Lin et al., The PD-1 /PD-L 1 complex resembles the antigen-binding Fv domains of antibodies and T cell receptors, PNAS, Feb. 26, 2008, vol. 105, No. 8, pp. 3011-3016.

Agata Y et al, "Expression of the PD-1 antigen on the surface of stimulated mouse T and B lymphocytes", International Immunology, vol. 8, No. 5, May 31, 1996.

Chang, et al., Metabolic Competition in the tumor Microenvironment Is a Driver of Cancer Progression, Cell 162, 1229-1241, Sep. 10, 2015.

Edwards et al., The remarkable flexibility of the human antibody repertoire; isolation of over one thousand different antibodies to a single protein, BLyS. J Mol Biol. Nov. 14, 2003;334(1): 103-18. (Year: 2003).

Goel et al., Plasticity within the antigen-combining site may manifest as molecular mimicry in the humoral immune response. J Immunol. Dec. 15, 2004; 173(12):7358-67. (Year: 2004).

Hescamp, Noninvasive Imaging of Tumor PD-L1 expression Using Radiolabeled Anti-PD-L1 Antibodies, Cancer Res; 75(14), Jul. 15, 2015.

Kanyavuz et al., Breaking the law: unconventional strategies for antibody diversification. Nat Rev Immunol. Jun. 2019; 19(6):355-368. (Year: 2019).

Lloyd et al., Modeling the human immune response: performance of a 1011 human antibody repertoire against a broad panel of therapeutically relevant antigens. Protein Eng Des Sel. Mar. 2009;22(3): 159-68. (Year: 2009).

\* cited by examiner

FIGS. 3A-3C
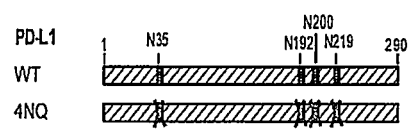
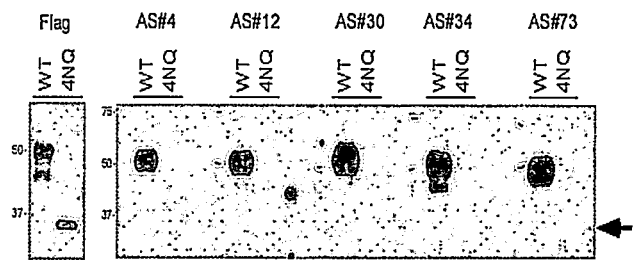
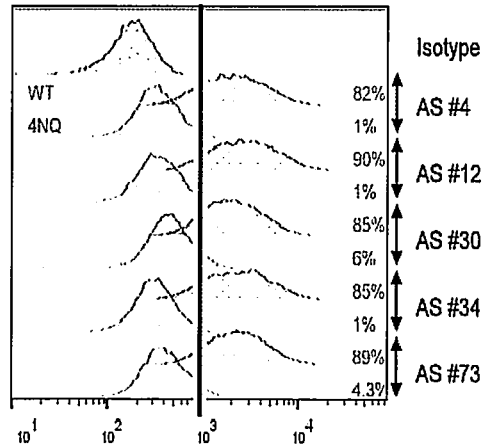
FIGS. 4A-4D
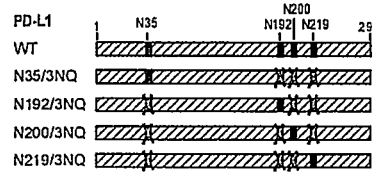
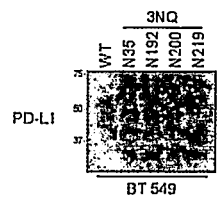
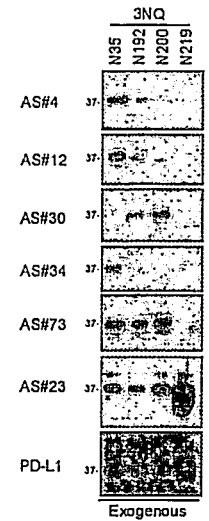
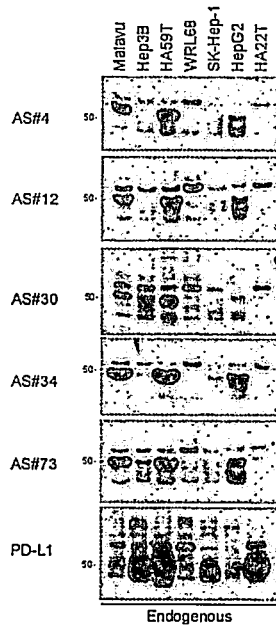

FIGS. 6A-6D
A
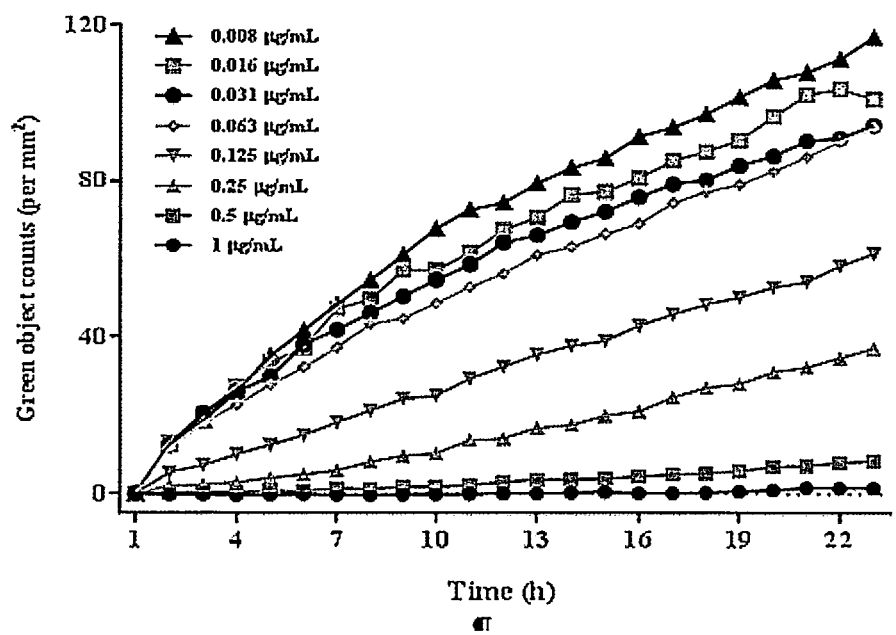
B
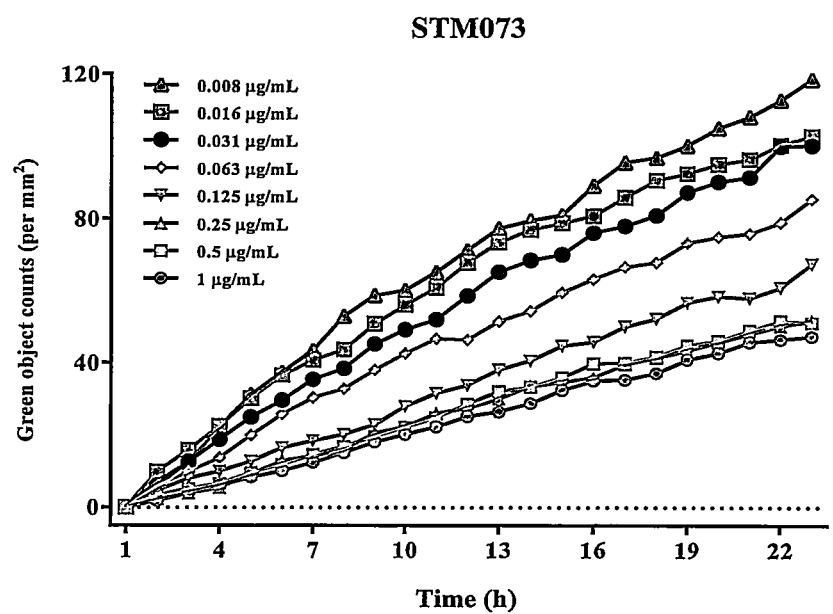

FIGS. 6A-6D (cont.)
C
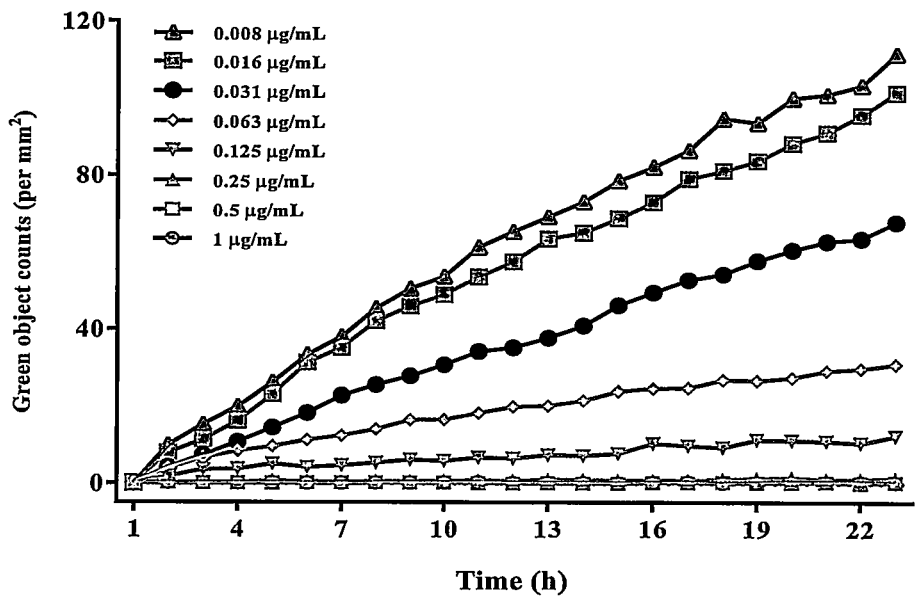
D
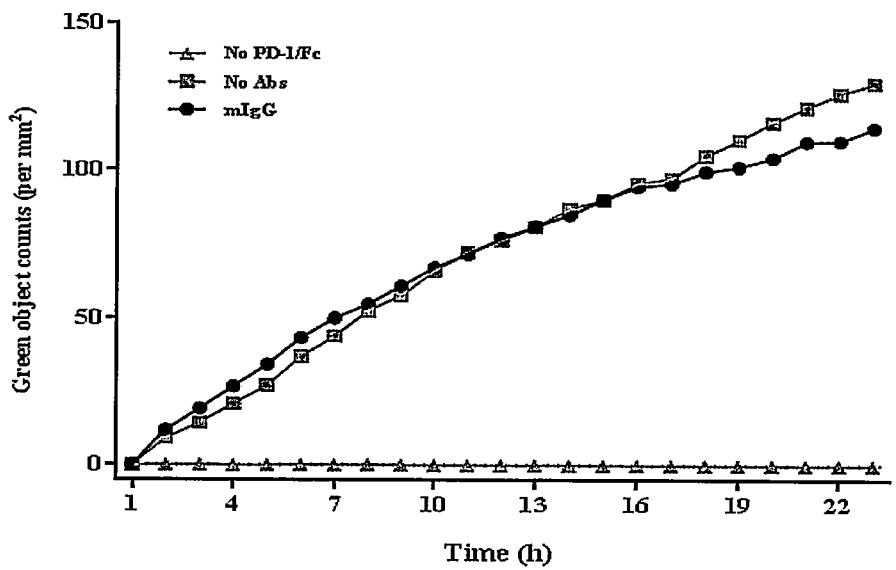

A

B

A

Time 0

B 2 minutes

C 4 minutes

FIGS. 9A-9L
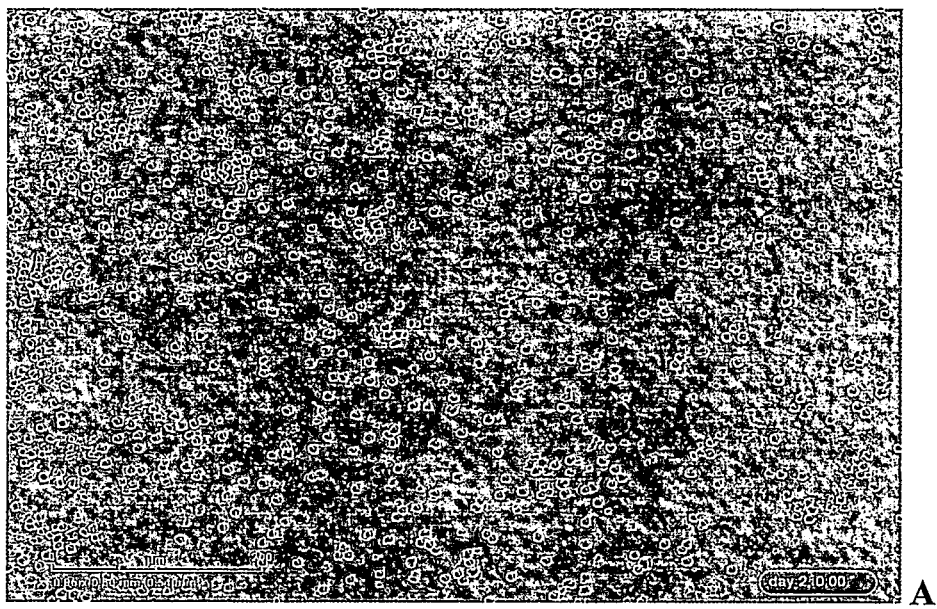
mIgG Control
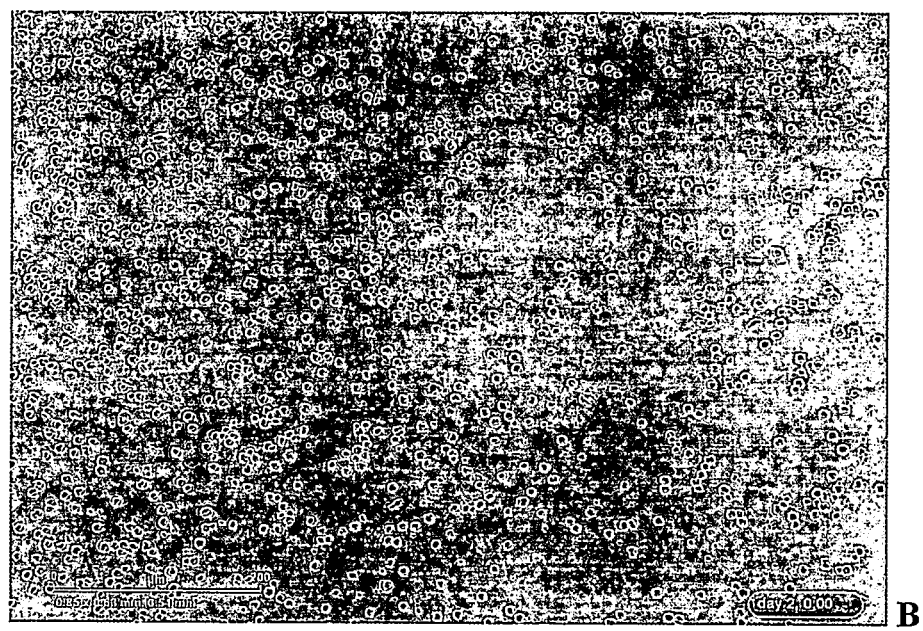
STM004 Antibody

FIGS. 9A-9L (Cont'd)
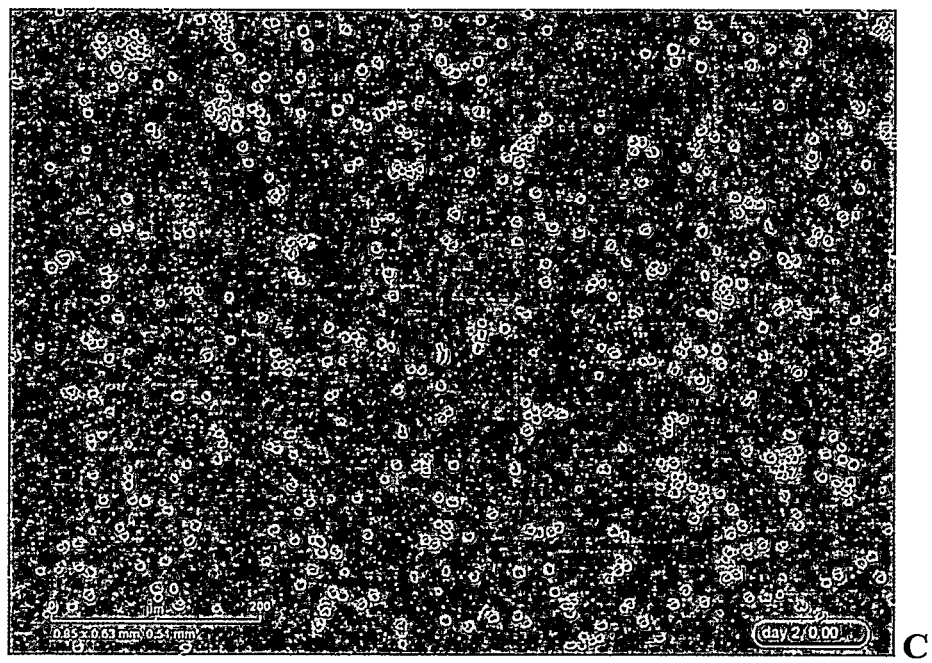
STM073 Antibody
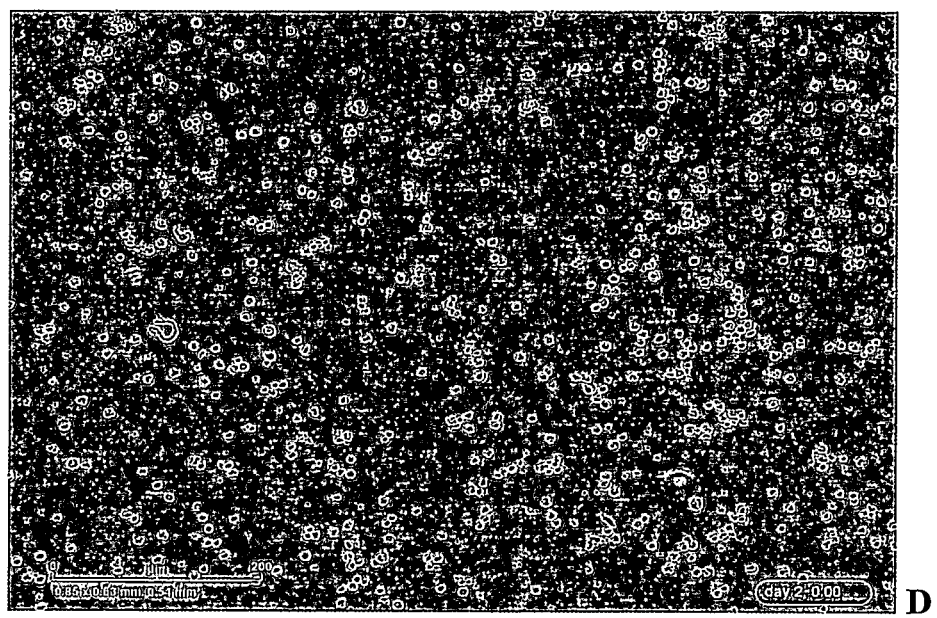
STM108 Antibody

FIGS. 9A-9L (Cont'd)
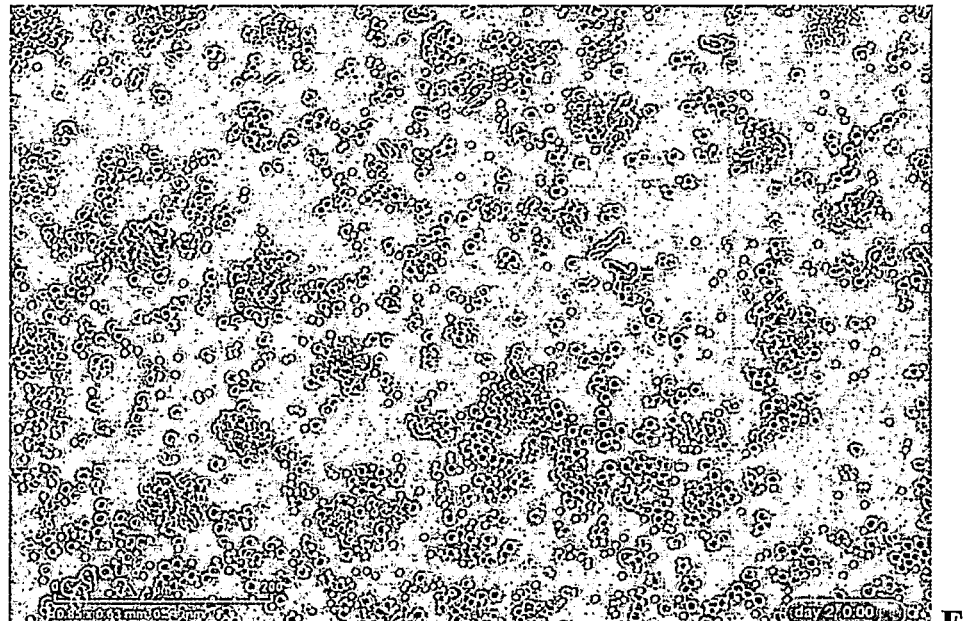
mIgG Control
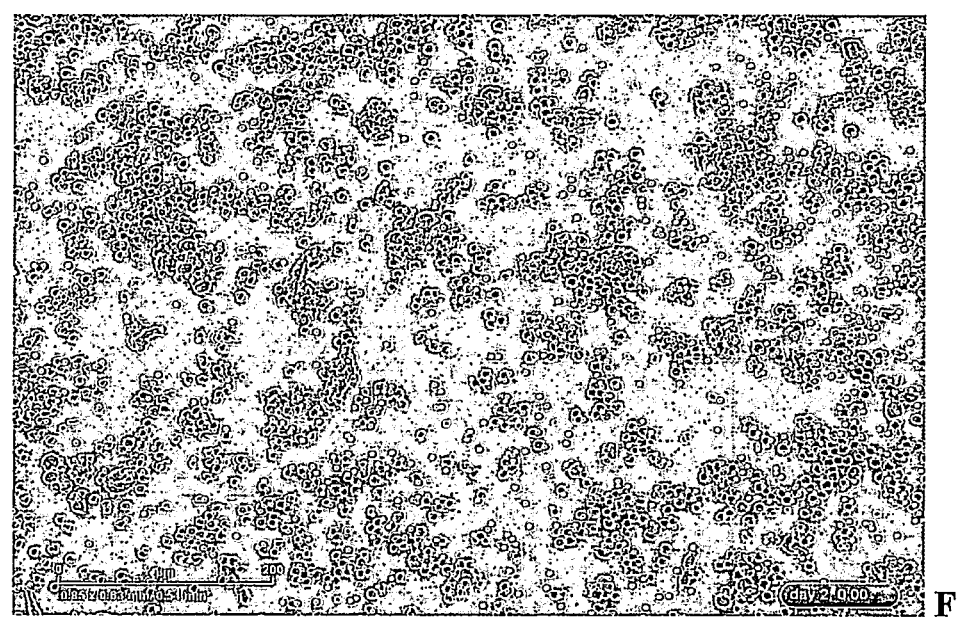
STM004 Antibody

FIGS. 9A-9L (Cont'd)
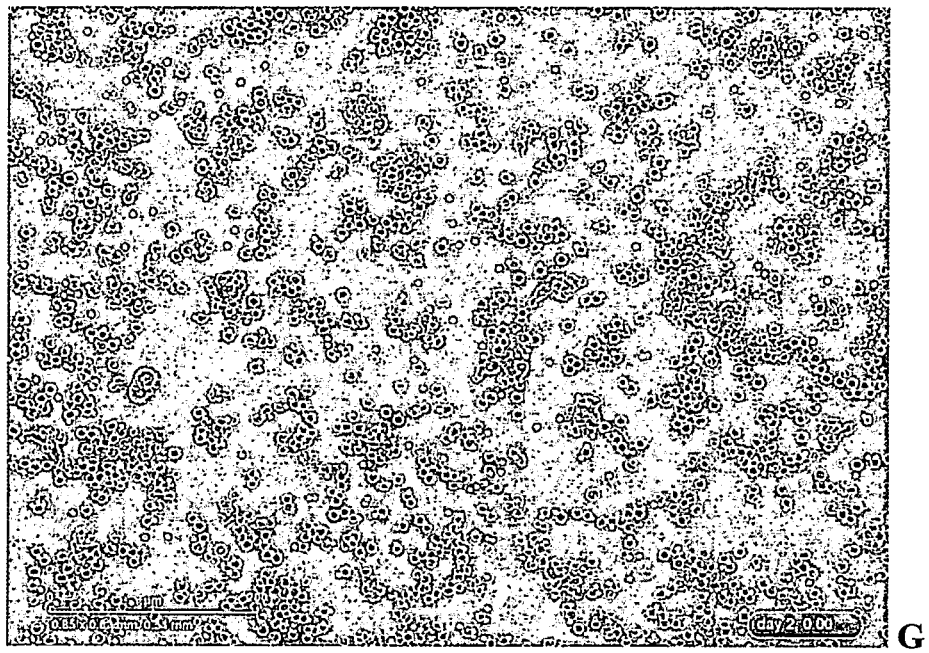
STM073 Antibody
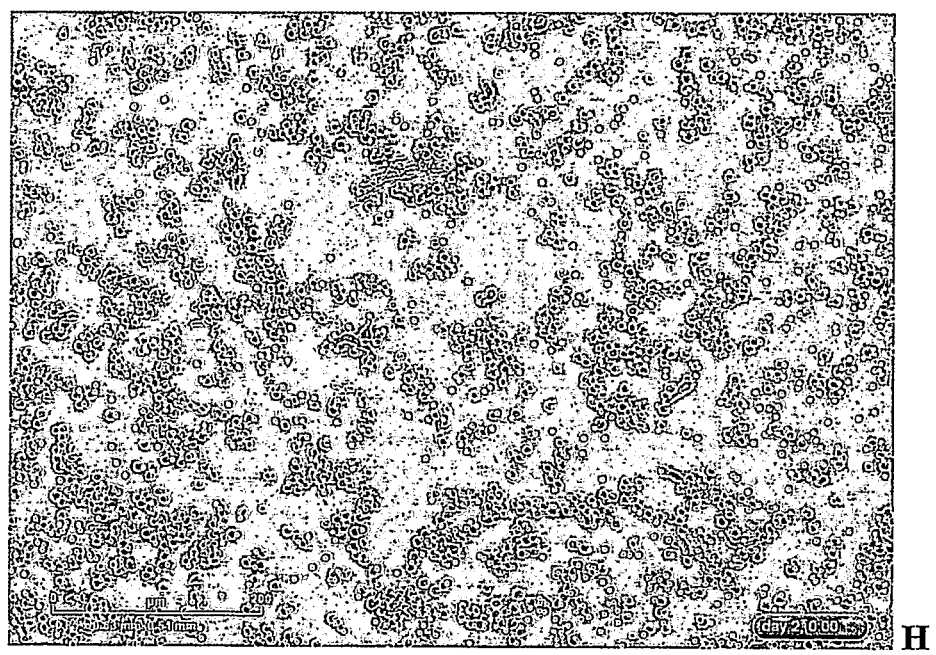
STM108 Antibody

FIGS. 9A-9L (Cont'd)
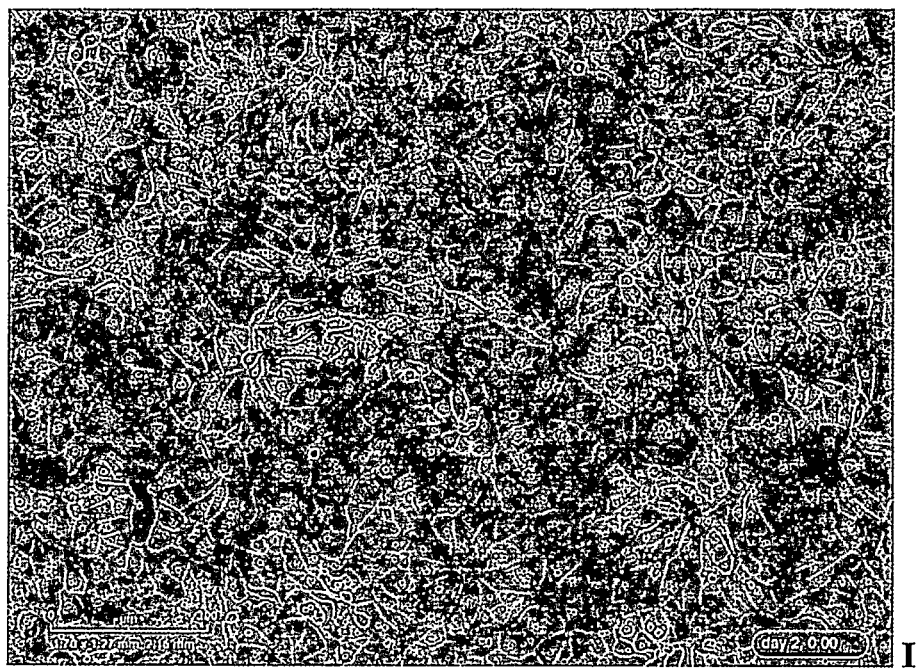
mIgG Control
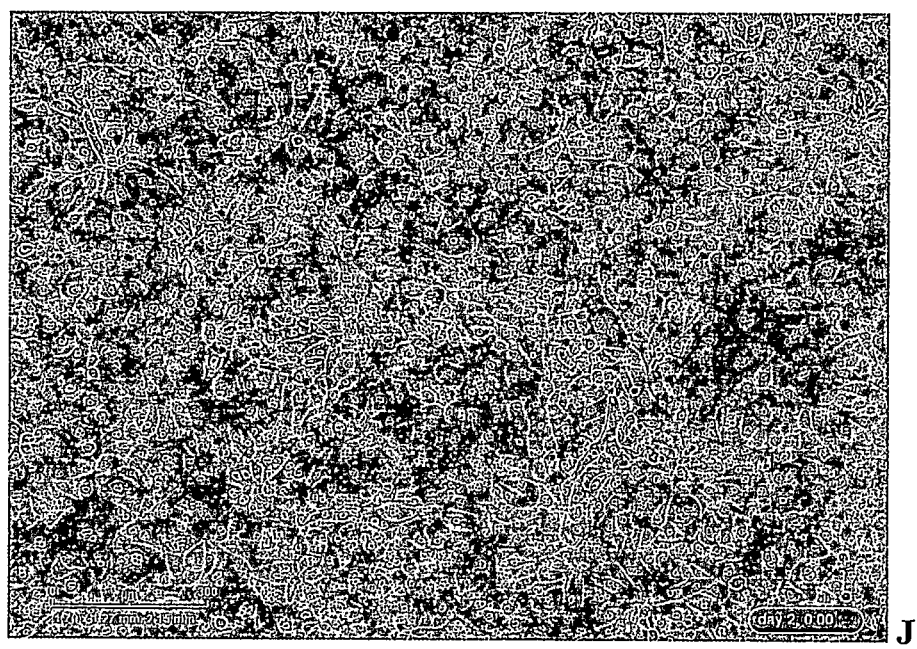
STM004 Antibody

FIGS. 9A-9L (Cont'd)
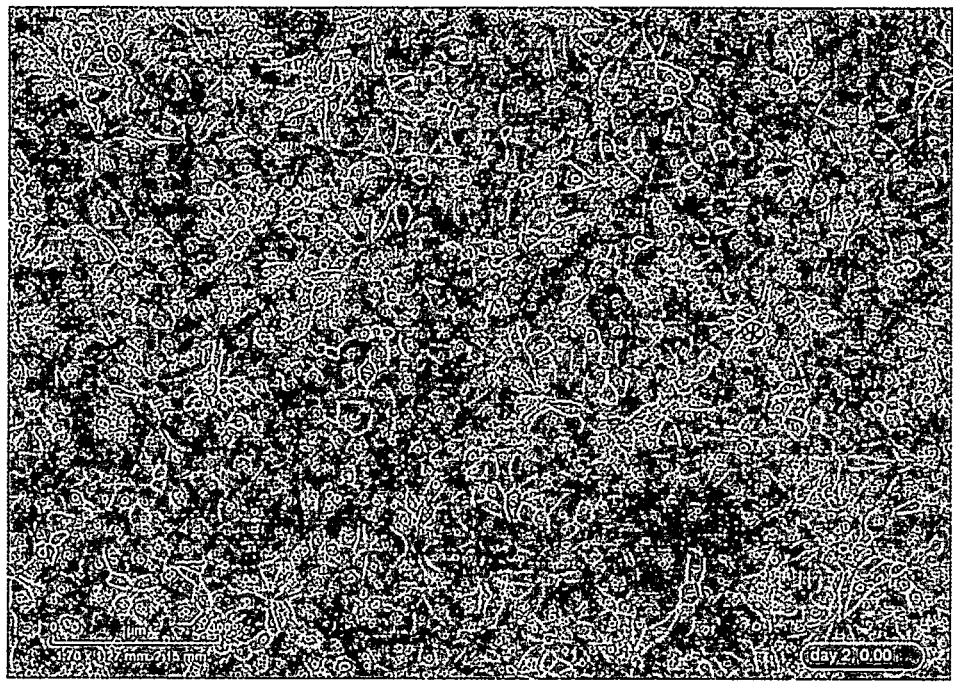
STM073 Antibody
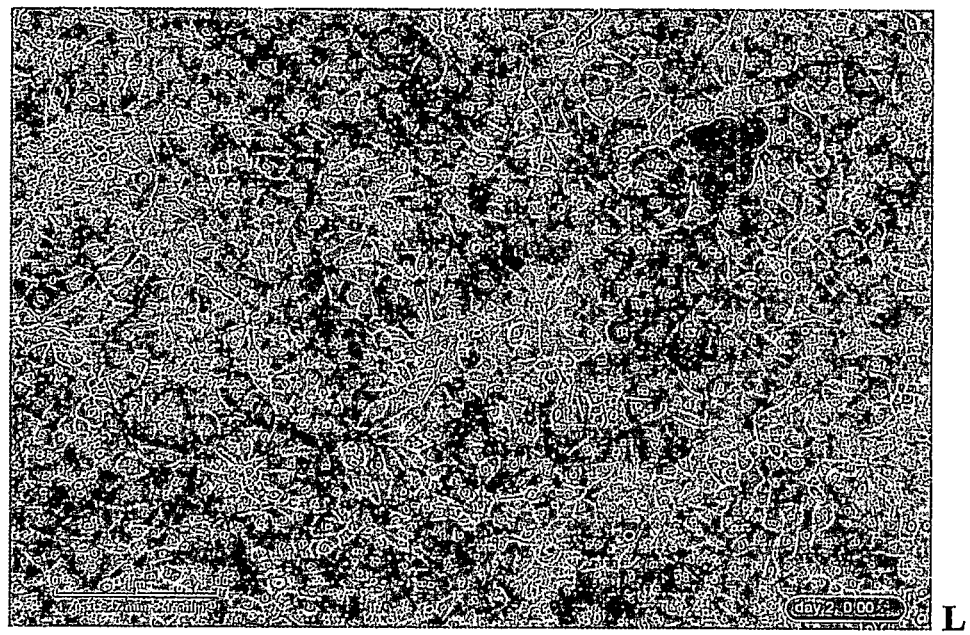
STM108 Antibody

METHODS FOR SELECTING ANTIBODIES THAT SPECIFICALLY BIND GLYCOSYLATED IMMUNE CHECKPOINT PROTEINS

SEQUENCE LISTING

The instant application contains a Sequence Listing which has been submitted electronically in ASCII format and is hereby incorporated by reference in its entirety. Said ASCII copy, created on Mar. 23, 2017, is named 24258_105006PCT_SL.txt and is 31,652 bytes in size.

RELATED FIELDS

The methods presented herein relate generally to the fields of molecular biology, medicine and oncology. More particularly, methods are provided for making, selecting and screening for antibodies that specifically and preferentially bind glycosylated immune checkpoint proteins.

BACKGROUND

Immune checkpoint pathways involve interactions between immune cells bearing immune checkpoint molecules (polypeptides and peptides) and, under normal conditions, maintain self-tolerance and limit collateral tissue damage during antimicrobial immune responses. These pathways can be utilized by cancer and tumor cells to evade immune destruction. Drugs are under development and testing in an effort to interrupt immune checkpoints, such as anti-CTLA-4, anti-PD-1, anti-PD-L1 antibodies, to block interactions of tumor cells with immune T cells, provide anti-tumor immunity and mediate sustained cancer regression therapies. The biology of immune checkpoint pathways is complex, and the full activity spectrum of checkpoint-blocking drugs, used alone or in combination, is currently the subject of intense study. (S. Topalian et al., 2015, *Cancer Cell*, 27(4): 450-461).

A confounding event in cancer disease etiology is that tumors are able to co-opt certain immune-checkpoint pathways as a major mechanism of immune resistance, particularly against T cells that are specific for tumor antigens. Because many of the immune checkpoints are initiated by ligand-receptor interactions, they can be readily blocked by antibodies or modulated by recombinant forms of ligands or receptors. For example, cytotoxic T-lymphocyte-associated antigen 4 (CTLA4) antibodies were among the first immunotherapeutics to be approved by the U.S. Food and Drug Administration (FDA). Findings with blockers of additional immune-checkpoint proteins, such as programmed cell death protein 1 (PD-1), indicate broad and diverse opportunities to enhance antitumor immunity with the potential to produce durable clinical responses. (D. Pardoll, 2012, *Nature Reviews Cancer*, 12:252-264). Therapeutic antibodies against PD-1, KEYTRUDA® pembrolizumab and OPDIVO® nivolumab, have been approved by the US FDA.

Methods are needed in the medical arena to generate and select for antibodies that specifically recognize and bind immune checkpoint molecules, particularly immune checkpoint molecules that are stably expressed on tumor cells and bind ligands on immune T cells, thus promoting immunosuppression of T cell activity against the tumor cells. Also needed are new and specific antibodies produced by such methods to block and inhibit the interaction of immune checkpoint molecules on tumor cells with a cognate ligand on effector T cells, so as to prevent or inhibit immunosuppression of the T cell response that is needed to destroy the tumor cells and ultimately treat cancer.

SUMMARY

The inventors have discovered that glycosylation of immune checkpoint proteins, abbreviated "ICP" herein, such as, for example, PD-L1 expressed on tumor cells, promotes or enhances binding to cognate ligand, for example, PD-1, on immune effector cells, thereby increasing the suppression of T cell activity against the tumor cells, and that glycosylation of ICPs, such as PD-L1, can also stabilize the expression of such immune checkpoint proteins on the cell surface. The inventors have developed methods to produce and identify antibodies that preferentially bind to glycosylated human ICPs (i.e., bind with a higher affinity to the glycosylated form of the ICP than to the unglycosylated form), such as the PD-L1 polypeptide (also known as CD274, PDCD1L1, or B7-H1) or the PD-1 polypeptide (also known as also known as CD279), relative to unglycosylated human ICPs and, by such specific binding, prevent or inhibit the interaction of the ICP, e.g., on a tumor cell, with its cognate ligand, e.g., on an immune effector cell such as a T cell, or a natural killer cell (NK cell) or vice versa. The methods herein provide antibodies that are selective for and preferentially bind glycosylated ICP and that serve as effective ICP inhibitors to prevent, reduce, block, or inhibit the immunosuppressive effects resulting from such tumor cell and T cell interaction through the ICP interaction pathway. It is to be understood that the terms "immune checkpoint protein" and "immune checkpoint polypeptide" (also called "immune checkpoint molecule") are abbreviated "ICP" herein. The term "glycosylated ICP" is abbreviated "glycICP" herein.

Provided herein are methods for producing and screening for or selecting for isolated antibodies that selectively recognize and preferentially bind a glycosylated ICP target antigen versus a non-glycosylated form or glycosylation variant form of the ICP target antigen (herein anti-glycICP antibodies), which may be present on cells of the immune system and/or on tumor cells. In some cases, the glycosylated ICP may be the wild type or naturally occurring form of the ICP (i.e., ICP WT); thus, ICP WT serves as a target antigen for antibody production and screening. In embodiments, populations of clonal antibodies produced by methods known in the art, e.g., hybridoma technology, phage display libraries of antibody repertoires, affinity matured antibodies, and the like, may be screened and selected for those antibodies that bind a glycosylated form of the ICP target antigen relative to a non-glycosylated form of the ICP target antigen.

In a particular embodiment, the glycosylated ICP antigen is human glycosylated PD-L1 polypeptide (also known as CD274, PDCD1L1, or B7-H1). In another particular embodiment, the glycosylated protein antigen is human glycosylated PD-1 polypeptide (also known as CD279). In another particular embodiment, the glycosylated ICP antigen is human glycosylated PD-L2 polypeptide. To the extent used herein, "PD-L1" refers to PD-L1 protein, polypeptide, or peptide, particularly human PD-L1 (the amino acid sequence of which is SEQ ID NO:1); and "PD-1" refers to PD-1 protein, polypeptide, or peptide, particularly human PD-1 (the amino acid sequence of which is SEQ ID NO: 2).

In another particular embodiment, the glycosylated ICP antigen is human glycosylated "T-cell Immunoglobulin and Mucin domain 3" (TIM-3), also known as CD366, FLJ14428, TIMD3 and HAVCR2 (amino acid sequence is SEQ ID NO: 4). In another particular embodiment, the glycosylated ICP antigen is human glycosylated "Lymphocyte Activation Gene-3" (LAG-3), also known as CD223 (amino acid sequence is SEQ ID NO: 5). In another particular embodiment, the glycosylated ICP antigen is human glycosylated "B and T Lymphocyte Attenuator" (BTLA), also known as CD272 (amino acid sequence is SEQ ID NO: 3). In another particular embodiment, the glycosylated ICP antigen is human glycosylated CD47, also known as TAP, MER6, and OA3. In another particular embodiment, the glycosylated ICP antigen is human glycosylated CD96, also known as CD96 molecule or CD96 antigen. In another particular embodiment, the glycosylated ICP antigen is human glycosylated "Carcinoembryonic Antigen-related Cell Adhesion Molecule 1 (biliary glycoprotein)" (CEACAM1), also known as BGP or BGP1 (amino acid sequence is SEQ ID NO: 7). In another particular embodiment, the glycosylated ICP antigen is human glycosylated "Butyrophilin subfamily 1 member A1" (BTN1A1), also known as BTN or BTN1 (amino acid sequence is SEQ ID NO: 6). In another particular embodiment, the glycosylated ICP antigen is human glycosylated Semaphorin 4D, also known as SEMAJ, CD100, coll-4 and FLJ39737 (amino acid sequence is SEQ ID NO: 8). In another particular embodiment, the glycosylated ICP antigen is human glycosylated "Butyrophilin-like 2" (BTNL2), also known as BTL-II, BTN7, HSBLMHCI and SS2. To the extent used herein, the ICP antigens of the embodiments refer to proteins, polypeptides, or peptides, particularly human ICP proteins, polypeptides, or peptides. In an aspect, by the practice of the methods described herein, antibodies made be produced and screened for preferentially binding to any of the foregoing ICPs, which include glycosylated amino acids as set forth in Table 1, infra. Briefly, the glycosylated ICP polypeptide, or a glycosylated portion thereof, may be used as immunogen to generate anti-glycICP antibodies that preferentially bind to the respective glycosylated ICP protein or portion thereof.

The antibodies that are produced and selected for their specificity for binding a glycosylated ICP versus a non-glycosylated ICP antigen may be used as ICP inhibitors that specifically bind a glycosylated ICP antigen and block the interaction of the ICP with its cognate ligand, which is usually a protein receptor expressed on another cell, for example, an immune cell or a tumor cell. For example, the antibody may bind the glycosylated form of the ICP antigen with 2 fold, 3 fold, 4 fold, 5 fold, 6 fold, 8 fold or 10 fold greater binding affinity than to the unglycosylated form of the ICP antigen but, in certain embodiments, is no greater than 20 fold, 50 fold, 100 fold, 1000 fold, or 10000 fold greater binding affinity than to the unglycosylated form of the ICP antigen.

Alternatively, the antibody may bind to the glycosylated ICP with a $K_d$ less than half of the $K_d$ exhibited by the antibody's binding to the corresponding unglycosylated ICP. In another embodiment, the antibody binds to the glycosylated ICP with a with a $K_d$ of less than 85%, less than 80%, less than 75%, less than 70%, less than 65%, less than 60%, less than 55%, less than 50%, less than 45%, less than 30%, less than 20% or less than 10% of the $K_d$ exhibited relative to the unglycosylated ICP. In further embodiment, the antibody binds to the glycosylated ICP with a $K_d$ that is no more than 10 times less, 100 times less or 1000 times less than the $K_d$ exhibited relative to the unglycosylated ICP.

Provided are methods of screening for and identifying an antibody that specifically and preferentially binds to a glycosylated ICP antigen comprising the steps of screening a population of clonal antibodies (such as, but not limited to, a population of hybridomas, a phage display library expressing a repertoire of antibodies, etc.) for one or more antibodies that specifically recognize and bind the glycosylated ICP antigen and then further screening the antibodies that specifically binding to the glycosylated ICP antigen for binding to the unglycosylated form of the ICP antigen with a lower affinity than the antibody binds to the glycosylated form. Alternatively, the population of antibodies is screened in one step for specific binding to the glycosylated ICP and preferential binding of the antibody to glycosylated ICP compared to unglycosylated ICP.

The screening can be carried out using any method known in the art, for example, panning with labeled glycosylated ICP antigen or testing the hybridoma medium or members of the library for binding to glycosylated ICP antigen or cultured cells expressing the glycosylated ICP with the antigen on a solid support, by western blotting, or by FACS or any other method known for detecting specific binding of an antibody for an antigen. Assaying for preferential binding to the glycosylated form of the ICP as compared to the unglycosylated form of the ICP can be carried out by comparing binding of the antibody to the glycosylated ICP antigen and unglycosylated ICP antigen each coated onto a solid surface or through FACS or flow cytometry.

In a preferred embodiment, the screening for preferential binding is carried out on cells expressing the glycosylated and unglycosylated forms of the ICP using flow cytometry. For example, cells that recombinantly express the WT ICP (which is glycosylated) can be mixed in culture with the same host cell that recombinantly expresses a mutant ICP that is not glycosylated (e.g., where the asparagine within a glycosylation site is substituted with glutamine), with one or both set of cells detectably or selectably labeled. For example, one set of cells can be labeled with biotin which can be detected and/or sorted through binding to streptavidin linked to a detectable or selectable marker. The mixture of cells can be contacted with the antibody to be tested (that may be directly or indirectly, such as with a secondary antibody that recognizes the antibody to be tested, labeled with a detectable or selectable marker) and, then binding to both types of cells assayed, for example, through FACS or other antibody binding assay, for example, as described in Example 2. In certain embodiments, an antibody is identified that preferentially binds to cells expressing the glycosylated ICP with at least 1.5 times, 2, times, 3 times, 4 times, 5 times, 6 times, 7 times, 8 times, 9 times, or 10 times greater frequency than to cells expressing unglycosylated ICP in a flow cytometry assay as described herein and, binding is measured, for example, by the measured fluorescence intensity (MFI) for the two populations of cells when the antibody is labeled directly or indirectly (for example with a labeled secondary antibody) with a fluorescent marker.

The glycosylated form is generally the wild type ICP or a peptide thereof. The unglycosylated form of the ICP can be generated by treating the ICP with an enzyme that removes glycosylation from the protein, particularly, N-linked glycosylation, for example, but not limited to digestion with PNGase F. Alternatively, the ICP can be mutated to remove the glycosylation site or sites within the protein. N-linked glycosylation generally occurs at the asparagine of the consensus sequence Asn-X-Ser/Thr (wherein X is any amino acid other than proline), such that a substitution of another amino acid for asparagine, preferably a glutamine, results in a protein that is not glycosylated at that site.

In an embodiment, the method further involves screening the anti-glycICP antibodies to identify anti-glycICP antibodies which specifically block interaction or binding between the glycosylated ICP antigen and its cognate ICP binding partner (ligand or receptor, such as for example, PD-1 is the cognate ICP binding partner of PD-L1). In an embodiment, the glycosylated ICP antigen or peptide thereof is expressed on a tumor or cancer cell, and the ICP ligand is expressed on an immune cell. In an embodiment, the glycosylated ICP antigen or peptide thereof is expressed on an immune cell, and the ICP ligand is expressed on a tumor or cancer cell. In an embodiment, the immune cell is an effector T cell or a natural killer cell (NK cell). The antibodies can be screened for inhibiting or blocking binding of the ICP to its ICP binding partner either by assaying for competition of the antibody for binding to the ICP with the ICP binding partner that is labeled, including a modified, soluble form of the binding partner such as an Fc fusion to the extracellular domain of the ICP binding partner. Alternatively, the antibody can be assayed for its ability to block ICP-ICP binding partner binding in a cellular assay in which a biological consequence of ICP-ICP binding partner binding is detected (for example, immunosuppression, changes in levels of certain cytokine production, etc.).

Provided are methods of generating an antibody, preferably a population of clones expressing antibodies, directed against a glycosylated ICP, comprising administering to a recipient animal a human glycosylated ICP or a peptide thereof comprising a fragment of at least 7 contiguous amino acids of a human ICP that comprises at least one glycosylated asparagine (N) amino acid modified by attachment to a glycan moiety in an amount effective to elicit an anti-glycosylated ICP immune response in the animal; and then preparing hybridomas from the animal for screening. In an embodiment, the animal is a mouse, rat, or rabbit, goat, donkey, or a non-human primate. Alternatively, a library of antibodies, for example, a phage library of antibodies, can be generated from the immunized animal or naïve libraries of antibodies may be used. In certain embodiments, the animal is transgenic for human immunoglobulins. In other embodiments, the library is a synthetic library representative of a human antibody repertoire. The antibody library may be clones expressing antibodies in any form, including tetrameric immunoglobulins, F(ab) fragments, scFvs, or single domain antibodies.

In an embodiment, the glycosylated ICP antigen for use in the methods of making and selecting antibodies is selected from PD-L1, PD-L2, PD-1, TIM-3, LAG-3, BTLA, CEACAM1, BTN1A1, BTNL2, SEMA4D, CD47, CD96, B7-H3, B7-H4, CTLA-4, VISTA, or KIR. Preferably, the ICP is a human ICP. In other embodiments, the glycosylated ICP antigen is one of the following: AGER, ALCAM, AMIGO1, AMIGO2, AMIGO3, AXL, B2M, BCAM, BCAN, BOC, BSG, BTN2A1, BTN2A2, BTN3A3, BTNL1, BTNL6, BTNL7, BTNL9, CADM1, CADM2, CADM3, CADM4, CD101, CD160, CD19, CD1D2, CD2, CD200, CD22, CD226, CD244, CD274, CD276, CD28, CD300A, CD300E, CD300LB, CD300LD, CD300LF, CD300LG, CD33, CD3E, CD3G, CD4, CD48, CD7, CD79A, CD79B, CD80, CD83, CD84, CD86, CD8A, CD8B, CD8B1, CDON, CEACAM3, CEACAM5, CHL1, CILP, CNTFR, CNTN1, CNTN2, CNTN6, CRL, CRTAM, CSF1R, CSF3R, CXADR, EMBF, ERMAP, ESAM, F11R, FAIM3, FCER1A, FCGR2B, FCGRT, FCRL1, FCRL5, FCRLA, FCRLB, FGFR1, FGFR2, FGFR4, FLT1, FLT3, GP6, GPA33, HAPLN1, HAPLN2, HAPLN3, HAVCR1, HEPACAM, HEPACAM2, ICAM1, ICAM2, ICAM4, ICAM5, ICOS, IFNGR1, KIT, L1CAM, LAIR1, LEPR, LILRA5, LILRB4, LINGO1, LINGO2, LINGO4, LRFN1, LRFN2, LRFN3, LRFN4, LRFN5, LRIG1, LRIG2, LRIG3, LRIT1, LRRC4, LRRN1, LRRN2, LRRN3, LSAMP, LSR, LY6G6F, LY9, MADCAM1, MAG, MALT1, MCAM, MERTK, MFAP3, MOG, MPZ, MPZL1, MPZL2, MPZL3, MR1, MUSK, MXRA8, NCAM1, NCAM2, NCR1, NEGR1, NEO1, NFAM1, NPTN, NRCAM, NRG1, NTM, NTRK1, NTRK2, NTRK3, OPCML, OSCAR, PAPLN, PDCD1, PDCD1LG2, PDGFRA, PDGFRB, PECAM1, PIGR, PRTG, PTGFRN, PTK7, PTPRD, PTPRK, PTPRS, PTPRT, PTPRU, PVR, PVRL1, PVRL2, PVRL3, PVRL4, PXDN, ROBO1, ROBO2, ROBO3, ROBO4, ROR1, ROR2, SCN1B, SCN2B, SCN3B, SEMA3A, SEMA3B, SEMA3C, SEMA3F, SEMA4A, SEMA4B, SEMA4C, SEMA4F, SEMA4G, SEMA7A, SIGGIR, SIGLEC1, SIGLEC5, SIRPA, SIRPB1, SLAMF1, SLAMF6, SLAMF7, SLAMF8, SLAMF9, TAPBP, TAPBPL, TEK, THY1, TIE1, TIGIT, TIMD4, TMEM25, TMEM81, TMIGD1, TREM1, TREM2, TREML1, TREML2, TREML4, TYRO3, UNC5A, UNC5B, UNC5C, VCAM1, VPREB1, VPREB3, VSIG1, VSIG2, VSIG4, VSIG8, VTCN1, WFIKKN2.

In an embodiment, the human glycosylated ICP antigen is an isolated polypeptide comprising a fragment of at least 7 contiguous amino acids of human PD-L1, wherein the polypeptide comprises at least one amino acid corresponding to position N35, N192, N200, or N219 of human PD-L1 (as numbered in SEQ ID NO:1), and wherein at least one of the amino acids corresponding to position N35, N192, N200 or N219 of PD-L1 is glycosylated. In an embodiment, the isolated polypeptide comprises at least 8-20 contiguous amino acids of human PD-L1. In an embodiment, the isolated polypeptide comprises a glycosylated amino acid corresponding to position N35, N192, N200, and/or N219 of human PD-L1. In another embodiment, the human glycosylated ICP antigen is an isolated polypeptide comprising a fragment of at least 7 contiguous amino acids of human PD-1, said polypeptide comprising at least one amino acid corresponding to position N49, N58, N74 and/or N116 of human PD-1 (as numbered in SEQ ID NO:2), wherein at least one of the amino acids corresponding to position N49, N58, N74 and/or N116 of PD-1 is glycosylated. In an embodiment, the isolated polypeptide comprises at least 8-20 contiguous amino acids of human PD-1. In an embodiment, the isolated polypeptide comprises a glycosylated amino acid corresponding to position N49, N58, N74 and/or N116 of human PD-1. In an embodiment, the isolated polypeptide is fused or conjugated at its amino or carboxy terminus to an immunogenic polypeptide that is not an ICP polypeptide.

In other embodiments where the antibody isolated is not a human antibody (e.g., it is a murine monoclonal antibody), the method further involves identifying the amino acids comprising complementarity determining regions (CDRs) of the antibody and humanizing the amino acid sequences surrounding the CDRs to produce a humanized antibody, which is recombinantly expressed. In an embodiment, the method involves recombinantly expressing the humanized antibody. Alternatively, the non-human constant domains of the antibody may be substituted with human constant domains to produce a chimeric antibody.

In another aspect, an isolated antibody produced by the above-described method is provided, wherein the antibody selectively and preferentially binds to a glycosylated ICP antigen relative to unglycosylated ICP. In an embodiment, the isolated antibody is an anti-glycosylated PD-L1 antibody. In embodiment, the isolated antibody is an anti-glycosylated PD-1 antibody. In an embodiment, the antibody is a monoclonal humanized, chimeric, or human antibody. In another embodiment, the antibody is of isotype IgM, IgG1, IgG2, IgG2a, IgG2b, IgG3, IgG4, or an antigen binding fragment thereof. In an embodiment, the antibody is selected from an Fab', an F(ab')$_2$, an F(ab')$_3$, a monovalent scFv, a bivalent scFv, or a single domain antibody. In another embodiment, the antibody is conjugated to an imaging agent, a chemotherapeutic agent, a toxin, or a radionuclide.

In a particular aspect, the methods described herein are suitable for screening and selecting an anti-glycosylated PD-L1 antibody (termed anti-glycPD-L1 antibody herein), that specifically and preferentially binds to glycosylated PD-L1 protein relative to unglycosylated PD-L1 protein. In an embodiment, the anti-glycPD-L1 antibody specifically binds to PD-L1 protein that is glycosylated at amino acid positions N35, N192, N200 and/or N219 of the PD-L1 protein, e.g., as set forth in SEQ ID NO: 1, in particular, in the extracellular domain (ECD) of the PD-L1 protein, relative to unglycosylated PD-L1 protein. In some embodiments, the anti-glycPD-L1 antibody specifically binds to one or more glycosylation motifs in the PD-L1 glycopolypeptide or peptides thereof. In some embodiments, the anti-glycPD-L1 antibody binds to a PD-L1 glycopeptide which comprises a glycosylation motif and the adjacent peptide. In some embodiments, the anti-glycPD-L1 antibody binds to a peptide sequence that is located near one or more of the glycosylation motifs in three dimensions. Accordingly, in embodiments, the anti-glycPD-L1 antibody recognizes and selectively binds to a conformational epitope of glycosylated PD-L1. By way of example, in certain embodiments, the anti-glycPD-L1 antibody binds to glycosylated PD-L1 with a $K_d$ less than half of the $K_d$ exhibited by the antibody's binding to unglycosylated PD-L1. In an embodiment, the anti-glycPD-L1 antibody binds to glycosylated PD-L1 protein with a $K_d$ at least 5 times less than the $K_d$ exhibited by the antibody's binding to unglycosylated PD-L1. In an embodiment, the anti-glycPD-L1 antibody binds to glycosylated PD-L1 protein with a $K_d$ at least 10 times less than the $K_d$ exhibited relative to unglycosylated PD-L1 protein. In an embodiment, in a cell flow cytometry binding assay as described in Example 2, the anti-glycPD-L1 antibody exhibits binding as expressed as MFI to cells expressing WT PD-L1 that is 1.5 times, 2 times, 3, times, 4 times, 5 times, 6 times, 7 times, 8 times, 9 times or 10 times greater than the MFI for binding to cells expressing unglycosylated PD-L1. In an embodiment, the anti-glycPD-L1 antibody selectively binds to glycosylated PD-L1 protein with an affinity of from 5-20 nM, 5-10 nM, or 10-20 nM. In embodiments, the antibody is a human, humanized, or recombinant antibody.

In another specific aspect, the methods are provided for screening and selecting an anti-glycosylated PD-1 antibody (termed anti-glycPD-1 antibody herein), or a binding fragment thereof, that specifically and preferentially binds to glycosylated PD-1 protein relative to unglycosylated PD-1 protein. In an embodiment, the anti-glycPD-1 antibody specifically binds to PD-1 protein that is glycosylated at amino acid positions N49, N58, N74 and/or N116 of the human PD-1 protein, e.g., as set forth in SEQ ID NO: 2, in particular, in the extracellular domain (ECD) of the PD-1 protein, relative to unglycosylated PD-1 protein. In some embodiments, the anti-glycPD-1 antibody specifically binds to one or more glycosylation motifs in the PD-1 glycopolypeptide or peptides thereof. In some embodiments, the anti-glycPD-1 antibody binds to a PD-1 glycopeptide which comprises a glycosylation motif and the adjacent peptide. In some embodiments, the anti-glycPD-1 antibody binds to a peptide sequence that is located near one or more of glycosylation motifs in three dimensions. Accordingly, in embodiments, the anti-glycPD-1 antibody recognizes and selectively binds to a nonlinear, conformational epitope of glycosylated PD-1. By way of example, in certain embodiments, the anti-glycPD-1 antibody binds to glycosylated PD-1 with a $K_d$ less than half of the $K_d$ exhibited by the antibody's binding to unglycosylated PD-1. In an embodiment, the anti-glycPD-1 antibody binds to glycosylated PD-1 protein with a $K_d$ at least 5 times less than the $K_d$ exhibited by the antibody's binding to unglycosylated PD-1. In an embodiment, the anti-glycPD-1 antibody binds to glycosylated PD-1 protein with a $K_d$ at least 10 times less than the $K_d$ exhibited relative to unglycosylated PD-1 protein. In an embodiment, in a cell flow cytometry binding assay as described in Example 2, the anti-glycPD-1 antibody exhibits binding as expressed as MFI to cells expressing WT PD-L1 that is 1.5 times, 2 times, 3, times, 4 times, 5 times, 6 times, 7 times, 8 times, 9 times or 10 times greater than the MFI for binding to cells expressing unglycosylated PD-L1. In an embodiment, the anti-glycPD-1 antibody selectively binds to glycosylated PD-1 protein with an affinity of from 5-20 nM, 5-10 nM, or 10-20 nM. In an embodiment, the antibody is a monoclonal antibody. In embodiments, the antibody is a human, humanized, or recombinant antibody.

In yet another aspect, provided are methods for assessing glycosylation, N-linked glycosylation, or N-glycosylation of an ICP in a biological sample, in which the method comprises contacting the ICP-containing sample with an antibody produced by the methods described herein (e.g., an antibody that selectively binds to glycosylated ICP relative to unglycosylated ICP). In some aspects, the method is an in vitro method or assay. In certain aspects, the biological sample is cell sample, a tissue sample, a body fluid (e.g., plasma, serum, blood, urine, sputum, lymph, ascites fluid, intraperitoneal fluid, cerebral or spinal fluid, and the like). In particular embodiments, the sample is a cell sample or a cell sample from a tumor or cancer obtained from a subject having a cancer or tumor. Such a cancer or tumor cell sample may be assayed for glycosylated ICP on the cancer or tumor cell surface using anti-glycosylated protein antibodies, particularly to determine that, if glycosylated ICP is present on the subject's cancer or tumor cells, the cells would likely be appropriate targets for treatment with one or more anti-glycosylated ICP antibodies. By way of example, a glycosylated ICP detectable by isolated antibodies that specifically bind to such glycosylated proteins and prevent or block their interaction with their cognate binding partner include PD-L1, PD-L2, PD-1, TIM-3, LAG-3, BTLA, CEACAM1, BTN1A1, BTNL2, SEMA4D, CD47, CD96, B7-H3, B7-H4, CTLA-4, VISTA, or KIR and the like.

In other embodiments, the antibody blocks interaction of the following with its cognate binding partner: AGER, ALCAM, AMIGO1, AMIGO2, AMIGO3, AXL, B2M, BCAM, BCAN, BOC, BSG, BTN2A1, BTN2A2, BTN3A3, BTNL1, BTNL6, BTNL7, BTNL9, CADM1, CADM2, CADM3, CADM4, CD101, CD160, CD19, CD1D2, CD2, CD200, CD22, CD226, CD244, CD274, CD276, CD28, CD300A, CD300E, CD300LB, CD300LD, CD300LF, CD300LG, CD33, CD3E, CD3G, CD4, CD48, CD7, CD79A, CD79B, CD80, CD83, CD84, CD86, CD8A, CD8B, CD8B1, CDON, CEACAM3, CEACAM5, CHL1, CILP, CNTFR, CNTN1, CNTN2, CNTN6, CRL, CRTAM, CSF1R, CSF3R, CXADR, EMBF, ERMAP, ESAM, F11R, FAIM3, FCER1A, FCGR2B, FCGRT, FCRL1, FCRL5, FCRLA, FCRLB, FGFR1, FGFR2, FGFR4, FLT1, FLT3, GP6, GPA33, HAPLN1, HAPLN2, HAPLN3, HAVCR1, HEPACAM, HEPACAM2, ICAM1, ICAM2, ICAM4, ICAM5, ICOS, IFNGR1, KIT, L1CAM, LAIR1, LEPR, LILRA5, LILRB4, LINGO1, LINGO2, LINGO4, LRFN1, LRFN2, LRFN3, LRFN4, LRFN5, LRIG1, LRIG2, LRIG3, LRIT1, LRRC4, LRRN1, LRRN2, LRRN3, LSAMP, LSR, LY6G6F, LY9, MADCAM1, MAG, MALT1, MCAM, MERTK, MFAP3, MOG, MPZ, MPZL1, MPZL2, MPZL3, MR1, MUSK, MXRA8, NCAM1, NCAM2, NCR1, NEGR1, NEO1, NFAM1, NPTN, NRCAM, NRG1, NTM, NTRK1, NTRK2, NTRK3, OPCML, OSCAR, PAPLN, PDCD1, PDCD1LG2, PDGFRA, PDGFRB, PECAM1, PIGR, PRTG, PTGFRN, PTK7, PTPRD, PTPRK, PTPRS, PTPRT, PTPRU, PVR, PVRL1, PVRL2, PVRL3, PVRL4, PXDN, ROBO1, ROBO2, ROBO3, ROBO4, ROR1, ROR2, SCN1B, SCN2B, SCN3B, SEMA3A, SEMA3B, SEMA3C, SEMA3F, SEMA4A, SEMA4B, SEMA4C, SEMA4F, SEMA4G, SEMA7A, SIGGIR, SIGLEC1, SIGLEC5, SIRPA, SIRPB1, SLAMF1, SLAMF6, SLAMF7, SLAMF8, SLAMF9, TAPBP, TAPBPL, TEK, THY1, TIE1, TIGIT, TIMD4, TMEM25, TMEM81, TMIGD1, TREM1, TREM2, TREML1, TREML2, TREML4, TYRO3, UNC5A, UNC5B, UNC5C, VCAM1, VPREB1, VPREB3, VSIG1, VSIG2, VSIG4, VSIG8, VTCN1, or WFIKKN2.

In an aspect, by the practice of the methods disclosed herein, there is provided an isolated antibody that selectively binds to an epitope, such as a conformational epitope, of a glycosylated ICP comprising a fragment of at least 7 contiguous amino acids with at least one glycosylated amino acid (e.g., an amino acid (N or asparagine) modified by attachment to a glycan moiety) relative to a non-glycosylated form of the polypeptide. In a particular embodiment, an isolated antibody is provided that selectively binds to an epitope, such as a conformational epitope, of PD-L1 comprising at least one amino acid corresponding to position N35, N192, N200 or N219 of human PD-L1, wherein at least one of the amino acids corresponding to position N35, N192, N200 or N219 of PD-L1 is glycosylated. In a particular embodiment, an isolated antibody is provided that selectively binds to an epitope, such as a conformational epitope, of PD-1 comprising at least one amino acid corresponding to position N49, N58, N74 or N116 of human PD-1, wherein at least one of the amino acids corresponding to position N49, N58, N74 or N116 of PD-1 is glycosylated.

In specific embodiments, the invention provides methods of making biparatopic antibodies that have two different antigen binding domains that each bind an epitope that does not overlap with the epitope of the other antigen binding domain of a glycosylated ICP, and at least one binding domain (and in certain embodiments, both binding domains) binds preferentially to a glycosylated form of the ICP, for example by binding an epitope containing one or more of the glycosylation sites listed herein. These antibodies can cross-link cell surface proteins promoting internalization, lysosomal trafficking and degradation. Such biparatopic antibodies may be generated by screening for antibodies that preferentially bind to a glycosylated ICP relative to a non-glycosylated form of the ICP using the screening methods described herein, identifying two antibodies that bind non-overlapping epitopes of the glycosylated ICP, where preferably one or both preferentially bind the glycosylated form of the ICP as compared to the non-glycosylated form. Antibodies against any of the glycosylation containing epitopes or epitopes described herein to which antibodies preferentially bind to glycosylated ICPs can be used. The two antigen binding domains can be arranged in an antibody molecule, for example, as described in Dimasi et al., *J. Mol. Biol.*, 393:672-692 (2009). In specific embodiments, one of the antigen binding domains is engineered to be in the format of a single chain Fv which is then linked to the N terminus of the heavy and/or light chains of an antibody having the other antigen binding domain or to the C-terminus of the CH3 domain, e.g., via a peptide linker.

In a particular aspect, the anti-glycICP antibody promotes the internalization and degradation of its target glycICP antigen after binding to the target antigen on the cell surface. If the target glycICP antigen is expressed, or highly expressed, on tumor cells, then internalization of glycosylated target antigen expressed on tumor cells following binding by the anti-glycICP antibodies provided herein results in less glycosylated ICP available on the tumor cell for interaction with cognate binding molecules on immune cells, such as T cells, for example, thereby increasing T cell cytotoxic effector function against the tumor cells and reducing T cell anergy resulting from the glycICP/cognate binding molecule interaction. In a specific embodiment, the antibody is an anti-glycPD-L1 antibody that inhibits the interaction of PD-1 with PD-L1, and particularly inhibits the interaction of PD-1 expressed by effector T-cells with PD-L1, particularly glycosylated PD-L1, expressed by tumor cells and also reduces the levels of PD-L1, particularly glycosylated PD-L1, on the surface of the tumor cells, particularly, by increasing the internalization and intracellular degradation of the PD-L1. Internalization of the PD-L1 expressed on tumor cells following binding by the anti-glycosylated PD-L1 antibodies provided herein is a beneficial feature of the anti-glycPD-L1 antibodies, as less glycosylated PD-L1 is available on the tumor cell for interaction with PD-1 on T cells, thereby increasing T cell cytotoxic effector function against the tumor cells and reducing T cell anergy resulting from the PD-L1/PD-1 interaction.

In another aspect, antibody-drug conjugates (ADCs) are provided, in which the anti-glycICP antibodies as described herein, in particular, those that show effective internalization activity following binding to glycosylated target antigen, are chemically linked to antineoplastic drugs and agents to produce an anti-glycICP antibody-drug conjugate (anti-glycICP antibody or MAb ADC), as described and exemplified herein. In certain embodiments, the anti-glycICP antibody-ADCs are highly effective in killing tumor or cancer cells and in antineoplastic therapies for treating subjects with cancer. In embodiments, the anti-glycICP antibody component of the ADC is a bispecific, multispecific, biparatopic, or multiparatopic antibody, or an antigen binding portion thereof. In other embodiments, the anti-glycICP antibody is chemically linked to an antimitotic agent, such as a maytansine derivative, e.g., a maytansinoid such as DM1 or DM4, or to a tubulin-polymerizing auristatin, e.g., monomethyl auristatin E (MMAE) or monomethyl auristatin F (MMAF), as described further herein. In an embodiment, the linker to the anti-glycICP antibody is stable in extracellular fluid, but is cleaved by cathepsin once the ADC has entered a tumor or cancer cell, thus activating the antimitotic mechanism of MMAE or other toxin drug. In an specific embodiment, the antibody component of the ADC is STM073 MAb or STM108 MAb as described herein. In an embodiment, the anti-glycICP antibody-containing ADC (anti-glycICP antibody-ADC), e.g., STM108 MAb-containing ADC (STM108-ADC), is chemically linked to MMAE via a cleavable linker. In a particular embodiment, the anti-glycICP antibody-ADC (e.g., STM108-ADC) comprises a structure in which the anti-glycICP antibody (e.g., STM108 MAb) is chemically linked via cysteine residues in its C-region to a maleimide and caproic acid (MC) attachment group, which is chemically linked to a cathepsin-cleavable linker, such as "vc" consisting of valine (Val) and citruline (Cit), which is chemically attached to the spacer "PAB", i.e., paraminobenzoic acid, which is chemically linked to MMAE cytotoxin, thus producing the ADC, designated by its component structure anti-glycICP antibody-MC-vc-PAB-MMAE, e.g., STM108-MC-vc-PAB-MMAE.

BRIEF DESCRIPTION OF THE DRAWINGS

The following drawings form part of the present specification and are included to further demonstrate certain aspects of the methods and antibodies described herein. They may be better understood by reference to one or more of these drawings in combination with the detailed description of the embodiments presented herein although they are not intended to be limiting. The patent or application file contains at least one drawing executed in color. Copies of this patent or patent application publication with color drawing(s) will be provided by the Office upon request and payment of the necessary fee.

FIGS. 3A-3C. Characterization of anti-glycosylated PD-L1 monoclonal antibodies. A. Schematic depiction of PD-L1 WT and non-glycosylated PD-L1 generated by mutating glycosylation sites within the PD-L1 amino acid sequence (PD-L1 4NQ for 4 glutamine (Q) for asparagine (N) substitutions). B. Western blot analysis of 5 anti-glycPD-L1 antibodies. Left panel shows equal amount of PD-L1 WT and 4NQ expression using anti-Flag antibody. C. Flow cytometry analysis of 5 anti-glycPD-L1 antibodies.

FIGS. 4A-4D. Characterization of anti-glycosylated PD-L1 antibodies. A. Schematic depiction of PD-L1 WT and non-glycosylated PD-L1 variants. B. Western blot analysis of stable clones of BT 549 expressing WT, N35/3NQ, N192/3NQ, N200/3NQ, and N219/3NQ PD-L1. C. Western blot analysis of 6 anti-glycPD-L1 antibodies. D. Western blot analysis of 5 anti-glycPD-L1 antibodies in liver cancer cell lines.

FIGS. 6A-6D. Binding Assays. FIGS. 6A-6C show the results of a binding assay as described in Example 5. Anti-glycPD-L1 antibodies block binding of PD-1 to BT549 target cells expressing WT PD-L1 in a dose dependent manner (FIG. 6A shows STM004 binding, FIG. 6B shows STM073 binding, and FIG. 6C shows STM108 binding) versus assay controls, No PD-1/Fc; No Ab; mIgG Ab (FIG. 6D).

FIGS. 7A (STM004) and 7B (STM073) show death (apoptosis) of PD-L1 WT expressing BT549 cells treated with the two different antibodies, respectively, in real time. In FIGS. 7A and 7B, the bottom graph (solid blue squares) represents the control (no T cells from PBMCs); the solid red circles represent a No Antibody control; the solid black squares represent 20 µg/ml of the anti-glycosylated PD-L1 antibody used in the assay; and the solid brown circles represent 40 µg/ml of the anti-glycosylated PD-L1 antibody used in the assay. As shown in FIGS. 7A and 7B, the killing of PD-L1 bearing tumor cells over time is dose-dependent.

FIGS. 8A-8C show the results of live cell imaging of PD-L1-expressing cells incubated with dual function anti-glycPD-L1 antibody. In FIGS. 8A-8C, the anti-PD-L1 antibody is STM108 MAb conjugated to a red fluorescent dye, pHrodo™ Red (succinimidyl ester (pHrodo™ Red, SE), (ThermoFisher Scientific, Waltham, MA). pHrodo™ Red dye conjugates are non-fluorescent outside the cell, but fluoresce brightly red in phagosomes, which makes them useful reagents for studies ranging from phagocytosis of bioparticles to receptor internalization. Green staining reflects cells stained with LysoTracker® Green DND-26, which is a cell permeable green dye that stains acidic compartments (lysosomes) in live cells imaged via live cell imaging. FIG. 8A shows that at a first time point (Time 0), STM108 is internalized into cells as depicted by the intense red intracellular staining of cells indicated by the arrow. FIG. 8B shows the weakened intracellular red staining in the same cells depicted in FIG. 8A, at a time 2 minutes after the time point in FIG. 8A. FIG. 8C shows the lack of red intracellular staining 4 minutes after the time point in FIG. 8A, which reflects the degradation of the STM108 antibody and/or the antibody-antigen complex inside the cells.

FIGS. 9A-9L. Internalization of PD-L1 Bound by Anti-PD-L1 Antibodies in Tumor Cells Versus Total T Cells. FIGS. 9A-9L present images of cells showing the ability of the dual function anti-glycPD-L1 antibodies to internalize into PD-L1 positive tumor cells, but not into either activated or non-activated T cells. FIGS. 9A-9D show images of non-activated total T cells from peripheral blood following incubation with the following antibodies: mouse IgG antibody control (FIG. 9A); non-internalizing anti-glycPD-L1 MAb STM004 (FIG. 9B); dual function anti-glycPD-L1 MAb STM073 (FIG. 9C); and dual function anti-glycPD-L1 antibody STM108 (FIG. 9D). FIGS. 9A-9D show that none of the antibodies tested were internalized into non-activated total T cells. FIGS. 9E-9H show images of activated total T cells from peripheral blood following incubation with the following antibodies: mouse IgG antibody control (FIG. 9E); non-internalizing STM004 (FIG. 9F); dual function STM073 (FIG. 9G); and dual function STM108 (FIG. 9ll). For T cell activation, total T cells were mixed with beads, e.g., inert, superparamagnetic beads, covalently coupled with anti-CD3 and anti-CD28 antibodies (e.g., ThermoFisher Scientific, Rochester, NY) at a 1:1 ratio. FIGS. 9E-9H show that virtually no internalization into activated total T cells was observed with any of the antibodies tested. FIGS. 9I-9L show images of NCI-H226 cells (human lung cancer cell line, squamous cell mesothelioma) following incubation with the following antibodies: mouse IgG antibody control (FIG. 9I); non-internalizing anti-glycPD-L1 antibody STM004 (FIG. 9J); dual function anti-glycPD-L1 MAb STM073 (FIG. 9K); and dual function anti-glycPD-L1 MAb STM108 (FIG. 9L). FIGS. 9I-9L show that the dual function, internalizing STM073 and STM108 MAbs were internalized into NCI-H226 cells following incubation with these cells, as evidenced by red intracellular staining, compared with the control antibody, mIgG (FIG. 9I) and with a non-internalizing STM004 MAb.

FIGS. 10A-10D present the results of experiments evaluating the efficacy of ADCs comprising dual function anti-glycPD-L1 MAb STM108, coupled to MMAE to produce an antibody-drug conjugate (STM108-ADC) as described herein, in killing PD-L1-expressing and non-PD-L1-expressing tumor cells and in reducing the volume of tumors in tumor-grafted mice following injection of tumored animals with the STM108 ADC compared with tumored animals injected with controls (IgG and STM108 MAb alone). FIG. 10A shows the % viability of PD-L1-expressing MDA-MB231 (human breast carcinoma cell line) tumor cells ("MB231") following exposure to different concentrations (nM) of STM108-ADC (filled black circles) compared with the % viability of MB231 cells molecularly engineered to knock out their expression of PD-L1 ("MB231 PDL1 KO") following exposure to different concentrations of STM108-ADC, i.e., "ADC108" (filled black squares). In FIG. 10B, an MDA-MB231 mouse model of breast cancer was used in which animals grafted with tumors derived from MB231 cells were treated with either an IgG-MMAE control (100 µg); or with STM108 ADC ("ADC") at 50 at 100 or at 150 µg; or with 100 µg of STM108 MAb, as indicated on the graph in FIG. 10B. Complete response ("CR") was observed in 3 of 5 mice administered 100 µg STM108-ADC and in 4 of 5 mice administered 150 µg STM108-ADC. FIG. 10C shows the % viability of 4T1 mammary carcinoma cells molecularly engineered to express human PD-L1 on the cell surface ("4T1 hPDL1") following exposure to different concentrations (nM) of STM108-ADC (open red circles) compared with the % viability of 4T1 cells that naturally do not express PD-L1 ("4T1") following exposure to different concentrations of STM108-ADC, i.e., "ADC108" (open red squares). In FIG. 10D, 4T1 syngeneic mouse models of breast cancer were used in which the animals (Balb/c mice) were grafted with tumors derived from 4T1 mammary carcinoma cells that had been molecularly engineered to express PD-L1 or the cell surface ("4T1 hPD-L1"), or in which the Balb/c mice were grafted with tumors derived from untransfected 4T1 mammary carcinoma cells that do not naturally express PD-L1 on the cell surface ("4T1"). Animals harboring tumors derived from the two types of 4T1 cells were treated with either an IgG-MMAE control (100 µg); or with STM108 MAb (100 µg), or with STM108 ADC (100 m), as indicated on the graph of FIG. 10D. See, Example 8.

Figure 1:
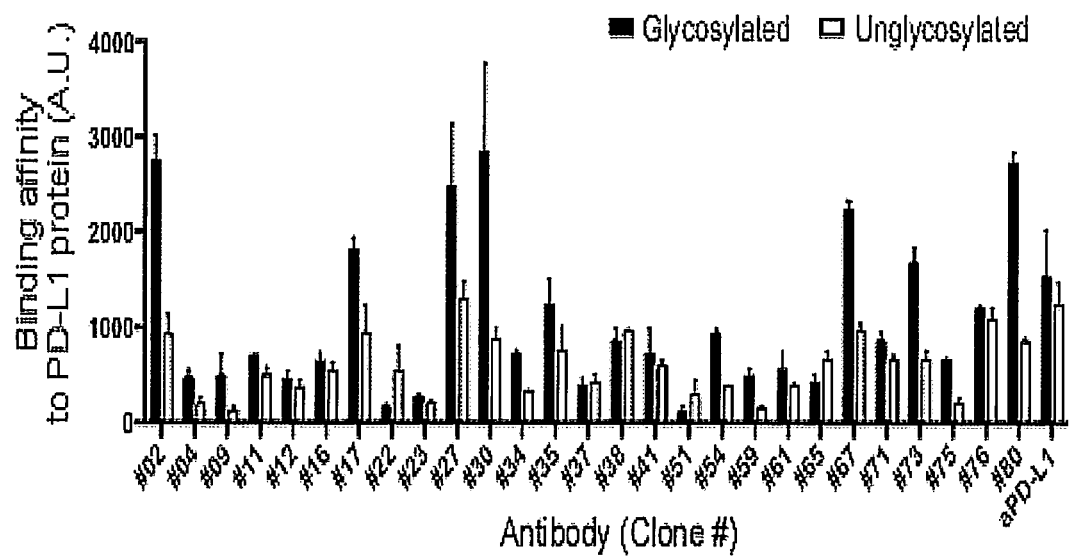
FIG. 1. In vitro human PD-L1 and anti-human PD-L1 antibody binding with or without PNGase F treatment. His-tagged PD-L1 was treated with or without PNGase F in native condition and then immobilized on an Ni-NTA coated plate. Fluorescence labeled anti-PD-L1 antibodies were incubated with the immobilized ligands, and binding affinity of the antibody for ligand was quantified.

Other aspects, features and advantages of the described embodiments will become apparent from the following detailed description and illustrative examples.

DETAILED DESCRIPTION OF THE EMBODIMENTS

Provided herein are methods for producing, screening and selecting antibodies, such as monoclonal antibodies (MAbs), that specifically and preferentially recognize and bind glycosylated immune checkpoint proteins (ICPs), or glycosylated peptides thereof, relative to non-glycosylated ICPs, or non-glycosylated peptides thereof. Nonlimiting examples of ICPs include PD-L1, PD-L2, PD-1, TIM-3, LAG-3, BTLA, CEACAM1, BTN1A1, BTNL2, SEMA4D, CD47, CD96, B7-H3, B7-H4, CTLA-4, VISTA, or KIR and the like, some or all of which are glycoproteins comprising one or more glycan structures. The acronym "MAb" is used herein to designate "monoclonal antibody."

As will be appreciated by the skilled practitioner in the art, the extracellular interaction between ICPs, such as programmed death ligand-1 protein (PD-L1) expressed on tumor cells and programmed death-1 protein (PD-1) expressed on immune effector cells, e.g., T-cells, has a marked impact on tumor-associated immune escape. (See, e.g., Pardoll, D. M., 2012, Nature Reviews, 12:252-264). Despite the clinical success of immune checkpoint blockade using anti-PD-1 or anti-PD-L1 antibodies, the regulatory mechanisms and structural features underlying the PD-L1 and PD-1 interaction remain largely unknown. N-linked glycosylation of PD-L1 was found to stabilize the PD-L1 protein ligand and also facilitate and enhance its binding to PD-1, which promotes the suppression of T cell-mediated immune response. Anti-glycPD-L1 antibodies generated by the methods described herein serve to prevent, block, or inhibit the PD-L1/PD-1 interaction and thus are useful as effective ICP inhibitors for cancer treatment.

In a particular embodiment, the glycosylated ICP antigen is human glycosylated PD-L1 polypeptide (also known as CD274, PDCD1L1, or B7-H1). In another particular embodiment, the glycosylated ICP antigen is human glycosylated PD-1 polypeptide (also known as CD279). In another particular embodiment, the glycosylated ICP antigen is human glycosylated PD-L2 polypeptide. To the extent used herein, "PD-L1" refers to PD-L1 protein, polypeptide, or peptide, particularly human PD-L1 (the amino acid sequence of which is SEQ ID NO:1); and "PD-1" refers to PD-1 protein, polypeptide, or peptide, particularly human PD-1 (the amino acid sequence of which is SEQ ID NO:2).

In particular embodiments, the glycosylated ICP antigen used in the methods described herein is an at least 7 amino acid polypeptide of PD-L1 protein that contains one of more of the glycosylation sites at positions N35, N192, N200 and/or N219 of the PD-L1 protein, e.g., as set forth in SEQ ID NO: 1. In another embodiment, the glycosylated ICP antigen used in the methods described herein is an at least 7 amino acid polypeptide of PD-1 protein that contains one or more of the glycosylation sites at amino acid positions N49, N58, N74 and/or N116 of the human PD-1 protein, e.g., as set forth in SEQ ID NO: 2.

In another particular embodiment, the glycosylated ICP antigen is human glycosylated "T-cell Immunoglobulin and Mucin domain 3" (TIM-3), also known as CD366, FLJ14428, TIMD3 and HAVCR2 (SEQ ID NO: 4). In another particular embodiment, the glycosylated ICP antigen is human glycosylated "Lymphocyte Activation Gene-3" (LAG-3), also known as CD223 (SEQ ID NO: 5). In another particular embodiment, the glycosylated ICP antigen is human glycosylated "B and T Lymphocyte Attenuator" (BTLA), also known as CD272 (SEQ ID NO: 3). In another particular embodiment, the glycosylated ICP antigen is human glycosylated CD47, also known as TAP, MER6, and OA3. In another particular embodiment, the glycosylated ICP antigen is human glycosylated CD96, also known as CD96 molecule or CD96 antigen. In another particular embodiment, the glycosylated ICP antigen is human glycosylated "Carcinoembryonic Antigen-related Cell Adhesion Molecule 1 (biliary glycoprotein)" (CEACAM1), also known as BGP or BGP1 (SEQ ID NO: 7). In another particular embodiment, the glycosylated ICP antigen is human glycosylated "Butyrophilin subfamily 1 member A1" (BTN1A1), also known as BTN or BTN1 (SEQ ID NO: 6). In another particular embodiment, the glycosylated ICP antigen is human glycosylated Semaphorin 4D, also known as SEMAJ, CD100, coll-4 and FLJ39737 (SEQ ID NO: 8). In another particular embodiment, the glycosylated ICP antigen is human glycosylated "Butyrophilin-like 2" (BTNL2), also known as BTL-II, BTN7, HSBLMHCI and SS2. To the extent used herein, the ICP antigens of the embodiments refer to proteins, polypeptides, or peptides, particularly human ICP proteins, polypeptides, or peptides.

TABLE 1

Glycosylation Sites of ICP Amino Acid Sequences

| ICP | Amino acid sequence showing N-linked glycosylation sites |
|---|---|
| BTLA | MKTLP AMLGT GKLFW VFFLI PYLDI WNIHG KESCD VQLYI KRQSE HSILA GDPFE LECPV KYCAN RPHVT WCKLN GTTCV KYLER QTSWK EEKNI SFFIL HFEPV LPNDN GSYRC SANFQ SNLIE SHSTT LYVTD VKSAS ERPSK DEMAS RPWLL YRLLP LGGLP LLITT CFCLF CCLRR HQGKQ NELSD TAGRE INLVD AHLKS EQTEA STRQN SQVLL SETGI YDNDP DLCFR MQEGS EVYSN PCLEE NKPGI VYASL NHSVI GPNSR LARNV KEAPT EYASI CVRS (SEQ ID NO: 3) |
| TIM-3 | SEVEY RAEVG QNAYL PCFYT PAAPG NLVPV CWGKG ACPVF ECGNV VLRTD ERDVN YWTSR YWLNG DFRKG DVSLT IENVT LADSG IYCCR IQIPG IMNDE KFNLK LVIKP AKVTP APTLQ RDFTA AFPRM LTTRG HGPAE TQTLG SLPDI NLTQI STLAN ELRDS RLAND LRDSG ATIRV DHEIHH HH (SEQ ID NO: 4) |
| LAG-3 | LQPGA EVPVV WAQEG APAQL PCSPT IPLQD LSLLR RAGVT WQHQP DSGPP AAAPG HPLAP GPHPA APSSW GPRPR RYTVL SVGPG GLRSG RLPLQ PRVQL DERGR QRGDF SLWLR PARRA DAGEY RAAVH LRDRA LSCRL RLRLG QASMT ASPPG SLRAS DWVIL NCSFS RPDRP ASVHW FRNRG QGRVP VRESP HHHLA ESFLF LPQVS PMDSG PWGCI LTYRD GFNVS IMYNL TVLGL EPPTP LTVYA GAGSR VGLPC RLPAG VGTRS FLTAK WTPPG GGPDL LVTGD NGDFT LRLED VSQAQ AGTYT CHIHL QEQQL NATVT LAIIT VTPKS FGSPG SLGKL LCEVT PVSGQ ERFVW SSLDT PSQRS FSGPW LEAQE AQLLS QPWQC QLYQG ERLLG AAVYF TELSS PG (SEQ ID NO: 5) |
| BTN1A1 | MAVFP SSGLP RCLLT LILLQ LPKLD SAPFD VIGPP EPILA VVGED AKLPC RLSPN ASAEH LELRW FRKKV SPAVL VHRDG REQEA EQMPE YRGRA TLVQD GIAKG RVALR IRGVR VSDDG EYTCF FREDG SYEEA LVHLK VAALG SDPHI SMQVQ ENGEI CLECT SVGWY PEPQV QWRTS KGEKF PSTSE SRNPD EEGLF TVAAS VIIRD TSAKN VSCYI QNLLL GQEKK VEISI PASSL PRLTP WIVAV AVILM VLGLL TIGSI FFTWR LYNER PRERR NEFSS KERLL EELKW KKATL HAVDV TLDPD TAHPH LFLYE DSKSV RLEDS RQKLP EKTER FDSWP CVLGR ETFTS GRHYW EVEVG DRTDW AIGVC RENVM KKGFD PMTPE NGFWA VELYG NGYWA LTPLR TPLPL AGPPR RVGIF LDYES GDISF YNMND GSDIY TFSNV TFSGP LRPFF CLWSS GKKPL TICPI ADGPE RVTVI ANAQD LSKEI PLSPM GEDSA PRDAD TLHSK LIPTQ PSQGA P (SEQ ID NO: 6) |
| CEACAM1 | MGHLS APLHR VRVPW QGLLL TASLL TFWNP PTTAQ LTTES MPFNV AEGKE VLLLV HNLPQ QLFGY SWYKG ERVDG NRQIV GYAIG TQQAT PGPAN SGRET IYPNA SLLIQ NVTQN DTGFY TLQVI KSDLV NEEAT GQFHV YPELP KPSIS SNNSN PVEDK DAVAF TCEPE TQDTT YLWWI NNQSL PVSPR LQLSN GNRTL TLLSV TRNDT GPYEC EIQNP VSANR SDPVT LNVTY GPDTP TISPS DTYYR PGANL SLSCY AASNP PAQYS WLING TFQQS TQELF IPNIT VNNSG SYTCH ANNSV TGCNR TTVKT IIVTE LSPVV AKPQI KASKT TVTGD KDSVN LTCST NDTGI SIRWF FKNQS LPSSE RMKLS QGNTT LSINP VKRED AGTYW CEVFN PISKN QSDPI MLNVN YNALP QENGL SPGAI AGIVI GVVAL VALIA VALAC FLHFG KTGRT TPMTH LTR (SEQ ID NO: 7) |
| Semaphorin 4D | MRMCT PIRGL LMALA VMFGT AMAFA PIPRI TWEHR EVHLV QFHEP DIYNY SALLL SEDKD TLYIG AREAV FAVNA LNISE KQHEV YWKVS EDKKA KCAEK GKSKQ TECLN YIRVL QPLSA TSLYV CGTNA FQPAC DHLNL TSFKF LGKNE DGKGR CPFDP AHSYT SVMVD GELYS GTSYN FLGSE PIISR NSSHS PLRTE RAANY TSSLN LPDKT LQFVK DHPLM SHTKW VRYNG PVPKP RPGAC IDSEA CAYNL STAEE VFSHG KYMQS TTVEQ SPGLK VPVFY ALFTP QLNNV GLSAV KARLI CSRPD SGLVF NVLRD VFVLR PRIAR VCKGD QGGLR TLQKK WTSFL GEDDR VYFFF TEVSV EYEFV FRVLI YAIPW LNEPS FVFAD VIRKS PDSPD DDSVT PIDNR PRLIK KDVNY TQIVV DRTQA LDGTV YDVMF VSTDR GALHK AISLE HAVHI IEETQ LFQDF EPVQT LLLSS KKGNR FVYAG SNSGV VQAPL AFCPK HGTCE DCVLA RDPYC AWSPP TATCV ALHQT ESPSR GLIQE MSGDA SVCPD KSKGS YRQHF FKHGG TAELK CSQKS NLARV FWKFQ NDVLK AESPK YGLMG RKNLL IFNLS EGDSG VYQCL SEERV KNKTV KHVLE VKVVP KPVVA PTLSV VQTEG SRIAT KVLVA STQGS SPPTP AVQAT SSGAI TLPPK PAPTG TSCEP KIVIN TVPQL HSEKT MYLKS SDNRL LMSLF LFFFV LFLCL FFYNC YKGYL PRQCL KFRSA LLIGK KKPKS DFCDR EQSLK ETLVE PGSFS QQNGE HPKPA LDTGY ETEQD TITSK VPTDR EDSQR IDDLS ARDKP FDVKC ELKFA DSDAD GD (SEQ ID NO: 8) |

In Table 1, the glycosylated amino acids (N) are indicated in bold and are underlined. Specifically, for BTLA, three glycosylation sites are shown at amino acid positions N75, N94 and N110 of the BTLA ICP protein sequence of SEQ ID NO: 3. For TIM-3, two glycosylation sites are shown at amino acid positions N78 and N151 of the TIM-3 ICP protein sequence of SEQ ID NO: 4. For LAG-3, four glycosylation sites are shown at amino acid positions N166, N228, N234 and N321 of the LAG-3 ICP protein sequence of SEQ ID NO: 5. For BTN1A1, three glycosylation sites are shown at amino acid positions N55, N215 and N449 of the BTN1A1 ICP protein sequence of SEQ ID NO: 6. For CEACAM1, three glycosylation sites are shown at amino acids positions N104, N111 and N115 of the BTLA ICP protein sequence of SEQ ID NO: 7. For Semaphorin 4D, six glycosylation sites are shown at amino acid positions N139, N191, N204, N254, N613, and N632 of the Semaphorin 4D amino acid sequence of SEQ ID NO: 8.

In certain embodiments, the glycosylated ICP antigen used in the described methods may be an at least 7 amino acid polypeptide of human BTLA that contains one or more of the glycosylation sites at amino acid positions N75, N94 and N110 of the BTLA ICP protein sequence of SEQ ID NO: 3. In certain embodiments, the glycosylated ICP antigen is an at least 7 amino acid polypeptide of human TIM-3 that contains one or both glycosylation sites at amino acid positions N78 and N151 of the TIM-3 ICP protein sequence of SEQ ID NO: 4. In certain embodiments, the glycosylated ICP antigen is an at least 7 amino acid polypeptide of human LAG-3 that contains one or more of the glycosylation sites at amino acid positions N166, N228, N234 and N321 of the LAG-3 ICP protein sequence of SEQ ID NO: 5. In certain embodiments, the glycosylated ICP antigen is an at least 7 amino acid polypeptide of human BTN1A1 that contains one or more of the glycosylation sites at amino acid positions N55, N215 and N449 of the BTN1A1 ICP protein sequence of SEQ ID NO: 6. In certain embodiments, the glycosylated ICP antigen is an at least 7 amino acid polypeptide of human CEACAM1 that contain one or more of the glycosylation sites at amino acids positions N104, N111 and N115 of the BTLA ICP protein sequence of SEQ ID NO: 7. In certain embodiments, the glycosylated ICP antigen is an at least 7 amino acid polypeptide of human Semaphorin 4D that contains one or more of the six glycosylation sites at amino acid positions N139, N191, N204, N254, N613, and N632 of the Semaphorin 4D amino acid sequence of SEQ ID NO: 8. Anti-glycICP antibodies may bind to epitopes containing one or more of these glycosylation sites.

In other embodiments, the glycosylated human ICP antigen for use in the methods of making and selecting antibodies is selected from PD-L2, BTNL2, B7-H3, B7-H4, CTLA-4, VISTA, or KIR. Preferably, the ICP is a human ICP. In other embodiments, the glycosylated ICP antigen (preferably human) is one of the following: AGER, ALCAM, AMIGO1, AMIGO2, AMIGO3, AXL, B2M, BCAM, BCAN, BOC, BSG, BTN2A1, BTN2A2, BTN3A3, BTNL1, BTNL6, BTNL7, BTNL9, CADM1, CADM2, CADM3, CADM4, CD101, CD160, CD19, CD1D2, CD2, CD200, CD22, CD226, CD244, CD274, CD276, CD28, CD300A, CD300E, CD300LB, CD300LD, CD300LF, CD300LG, CD33, CD3E, CD3G, CD4, CD48, CD7, CD79A, CD79B, CD80, CD83, CD84, CD86, CD8A, CD8B, CD8B1, CDON, CEACAM3, CEACAM5, CHL1, CILP, CNTFR, CNTN1, CNTN2, CNTN6, CRL, CRTAM, CSF1R, CSF3R, CXADR, EMBF, ERMAP, ESAM, F11R, FAIM3, FCER1A, FCGR2B, FCGRT, FCRL1, FCRL5, FCRLA, FCRLB, FGFR1, FGFR2, FGFR4, FLT1, FLT3, GP6, GPA33, HAPLN1, HAPLN2, HAPLN3, HAVCR1, HEPACAM, HEPACAM2, ICAM1, ICAM2, ICAM4, ICAM5, ICOS, IFNGR1, KIT, L1CAM, LAIR1, LEPR, LILRA5, LILRB4, LINGO1, LINGO2, LINGO4, LRFN1, LRFN2, LRFN3, LRFN4, LRFN5, LRIG1, LRIG2, LRIG3, LRIT1, LRRC4, LRRN1, LRRN2, LRRN3, LSAMP, LSR, LY6G6F, LY9, MADCAM1, MAG, MALT1, MCAM, MERTK, MFAP3, MOG, MPZ, MPZL1, MPZL2, MPZL3, MR1, MUSK, MXRA8, NCAM1, NCAM2, NCR1, NEGR1, NEO1, NFAM1, NPTN, NRCAM, NRG1, NTM, NTRK1, NTRK2, NTRK3, OPCML, OSCAR, PAPLN, PDCD1, PDCD1LG2, PDGFRA, PDGFRB, PECAM1, PIGR, PRTG, PTGFRN, PTK7, PTPRD, PTPRK, PTPRS, PTPRT, PTPRU, PVR, PVRL1, PVRL2, PVRL3, PVRL4, PXDN, ROBO1, ROBO2, ROBO3, ROBO4, ROR1, ROR2, SCN1B, SCN2B, SCN3B, SEMA3A, SEMA3B, SEMA3C, SEMA3F, SEMA4A, SEMA4B, SEMA4C, SEMA4F, SEMA4G, SEMA7A, SIGGIR, SIGLEC1, SIGLEC5, SIRPA, SIRPB1, SLAMF1, SLAMF6, SLAMF7, SLAMF8, SLAMF9, TAPBP, TAPBPL, TEK, THY1, TIE1, TIGIT, TIMD4, TMEM25, TMEM81, TMIGD1, TREM1, TREM2, TREML1, TREML2, TREML4, TYRO3, UNC5A, UNC5B, UNC5C, VCAM1, VPREB1, VPREB3, VSIG1, VSIG2, VSIG4, VSIG8, VTCN1, or WFIKKN2.

Methods of producing anti-glycICP antibodies screened for selectively and preferentially binding to glycosylated versus non-glycosylated ICPs are not intended to be limiting. In a particular embodiment, hybridoma methodology is employed to produce monoclonal antibodies (MAbs) against the glycosylated ICP antigen, which are screened for specific binding to glycosylated ICPs or glycosylated peptides thereof. According to the present methods, glycosylated ICPs or glycosylated peptides thereof, are used as an antigen or immunogen to immunize non-human animals to elicit an immune response and generate B cells that produce antibodies against the glycosylated ICP. The antibodies are then screened for specific binding to the glycosylated ICP and for preferential binding to the glycosylated ICP as compared to the unglycosylated form of the ICP. The antibodies may also be screened for blocking or inhibiting the binding of the glycosylated ICP to its ICP binding partner. In an example, the antibodies selectively and preferentially bind to glycosylated PD-L1 and block or inhibit binding of PD-L1 to PD-1. Alternatively, the antibodies selectively and preferentially bind to glycosylated PD-1 and block or inhibit binding of PD-1 to a binding partner of PD-1, including, PD-L1 or PD-L2. The antibodies selected and identified by the methods provided herein have use as therapeutics that can modulate the immune suppression activity mediated by ICPs or as reagents useful in detecting and characterizing glycosylated ICPs in biological samples.

Monoclonal antibodies are antibodies that are monospecific for a given target antigen. MAbs are synthesized and produced by identical immune B cells that are all clones of a unique parent B cell, in contrast to polyclonal antibodies which are directed to the target antigen but are produced by different B cells. Monoclonal antibodies have monovalent affinity and bind to the same epitope. In general, monoclonal antibodies can be produced that specifically bind to a target antigen used as an immunogen to generate the antibodies. Such MAbs can then serve to detect or purify the target antigen or modulate the biological activity of the target antigen. In addition, MAbs, particularly, isolated and purified MAbs, having specificity for a given target antigen may be used in treatments for diseases and pathological conditions, such as cancers, tumors, and the like. In embodiments, the target antigen is a glycosylated ICP or a glycosylated peptide portion thereof. In embodiments, MAbs generated against a glycosylated ICP or a glycosylated peptide portion thereof specifically and selectively recognize and bind the glycosylated ICP relative to a non-glycosylated ICP.

Definitions

As used herein, the term "a" or "an" may mean one or more.

As used herein, the term "or" means "and/or" unless explicitly indicated to refer to alternatives only or the alternatives are mutually exclusive, although the disclosure supports a definition that refers to only alternatives and "and/or."

As used herein, the term "another" means at least a second or more.

As used herein, the term "about" is used to indicate that a value includes the inherent variation of error for the device, the method being employed to determine the value, or the variation that exists among the study subjects.

As used herein, the term "programmed death ligand-1" or "PD-L1" refers to a polypeptide (the terms "polypeptide" and "protein" are used interchangeably herein) or any native PD-L1 from any vertebrate source, including mammals such as primates (e.g., humans, cynomolgus monkey (cyno)), dogs, and rodents (e.g., mice and rats), unless otherwise indicated, and, in certain embodiments, included various PD-L1 isoforms, related PD-L1 polypeptides, including SNP variants thereof. Similarly, the term "programmed death-1" or "PD-1" refers to PD-1 from any vertebrate source, including mammals such as primates (e.g., humans, cynomolgus monkey (cyno)), dogs, and rodents (e.g., mice and rats). Unless otherwise specified, PD-1 also includes various PD-1 isoforms, related PD-1 polypeptides, including SNP variants thereof, as well as different modified forms of PD-1, including but not limited to phosphorylated PD-1, glycosylated PD-1, and ubiquitinated PD-1.

An exemplary amino acid sequence of human PD-L1 (UniProtKB/Swiss-Prot: Q9NZQ7.1; GI:83287884) is provided below:

```
                                              (SEQ ID NO: 1)
MRIFAVFIFM TYWHLLNAFT VTVPKDLYVV EYGSNMTIEC

KFPVEKQLDL AALIVYWEME DKNIIQFVHG EEDLKVQHSS

YRQRARLLKD QLSLGNAALQ ITDVKLQDAG VYRCMISYGG

ADYKRITVKV NAPYNKINQR ILVVDPVTSE HELTCQAEGY

PKAEVIWTSS DHQVLSGKTT TTNSKREEKL FNVTSTLRIN

TTTNEIFYCT FRRLDPEENH TAELVIPELP LAHPPNERTH

LVILGAILLC LGVALTFIFR LRKGRMMDVK KCGIQDTNSK

KQSDTHLEET.
```

In SEQ ID NO: 1, the amino terminal amino acids 1-18 constitute the signal sequence of the human PD-L1 protein. Accordingly, the mature human PD-L1 protein consists of amino acids 19-290 of SEQ ID NO: 1.

An exemplary amino acid sequence of human PD-1 (UniProtKB; Q15116.3 GI:145559515) is provided below:

```
                                              (SEQ ID NO: 2)
MQIPQAPWPV VWAVLQLGWR PGWFLDSPDR PWNPPTFSPA

LLVVTEGDNA TFTCSFSNTS ESFVLNWYRM SPSNQTDKLA

AFPEDRSQPG QDCRFRVTQL PNGRDFHMSV VRARRNDSGT

YLCGAISLAP KAQIKESLRA ELRVTERRAE VPTAHPSPSP
```

-continued
```
RPAGQFQTLV VGVVGGLLGS LVLLVWVLAV ICSRAARGTI

GARRTGQPLK EDPSAVPVFS VDYGELDFQW REKTPEPPVP

CVPEQTEYAT IVFPSGMGTS SPARRGSADG PRSAQPLRPE

DGHCSWPL.
```

In SEQ ID NO: 2, the glycosylated amino acid residues are underlined and shown in bold. Also in SEQ ID NO: 2, the amino terminal amino acids 1-20 constitute the signal sequence of the human PD-1 protein. Accordingly, the mature human PD-1 protein consists of amino acids 21-288 of SEQ ID NO: 2.

Abbreviations for the amino acid residues that comprise polypeptides and peptides described herein, and conservative substitutions for these amino acid residues are shown in Table 2 below. A polypeptide that contains one or more conservative amino acid substitutions or a conservatively modified variant of a polypeptide described herein refers to a polypeptide in which the original or naturally occurring amino acids are substituted with other amino acids having similar characteristics, for example, similar charge, hydrophobicity/hydrophilicity, side-chain size, backbone conformation, structure and rigidity, etc. Thus, these amino acid changes can typically be made without altering the biological activity, function, or other desired property of the polypeptide, such as its affinity or its specificity for antigen. In general, single amino acid substitutions in nonessential regions of a polypeptide do not substantially alter biological activity. Furthermore, substitutions of amino acids that are similar in structure or function are less likely to disrupt the polypeptides' biological activity.

TABLE 2

Amino Acid Residues and Examples of Conservative Amino Acid Substitutions

| Original residue Three letter code and Single letter code | Conservative substitution(s) |
| --- | --- |
| Alanine (Ala) (A) | Gly; Ser |
| Arginine (Arg) (R) | Lys; His |
| Asparagine (Asn) (N) | Gln; His |
| Aspartic Acid (Asp) (D) | Glu; Asn |
| Cysteine (Cys) (C) | Ser; Ala |
| Glutamine (Gln) (Q) | Asn |
| Glutamic Acid (Glu) (E) | Asp; Gln |
| Glycine (Gly) (G) | Ala |
| Histidine (His) (H) | Asn; Gln |
| Isoleucine (Ile) (I) | Leu; Val |
| Leucine (Leu) (L) | Ile; Val |
| Lysine (Lys) (K) | Arg; His |
| Methionine (Met) (M) | Leu; Ile; Tyr |
| Phenylalanine (Phe) (F) | Tyr; Met; Leu |
| Proline (Pro) (P) | Ala |
| Serine (Ser) (S) | Thr |
| Threonine (Thr) (T) | Ser |
| Tryptophan (Trp) (W) | Tyr; Phe |
| Tyrosine (Tyr) (Y) | Trp; Phe |
| Valine (Val) (V) | Ile; Leu |

The terms "antibody," "immunoglobulin," and "Ig" are used interchangeably herein in a broad sense and specifically cover, for example, individual anti-glycosylated ICP antibodies, such as the monoclonal antibodies described herein, (including agonist, antagonist, neutralizing antibodies, full length or intact monoclonal antibodies, peptide fragments of antibodies that maintain antigen binding activity), anti-unglycosylated ICP antibodies and anti-glycosylated ICP antibodies; anti-ICP antibody compositions with polyepitopic or monoepitopic specificity, polyclonal or monovalent antibodies, multivalent antibodies, multi specific antibodies (e.g., bispecific antibodies or biparatopic antibodies, so long as they exhibit the desired biological activity) formed from at least two intact antibodies or antigen binding fragments thereof, single chain anti-ICP antibodies, and fragments of anti-ICP antibodies, as described below. An antibody can be human, humanized, chimeric and/or affinity matured. An antibody may be from other species, for example, mouse, rat, rabbit, etc. The term "antibody" is intended to include a polypeptide product of B cells within the immunoglobulin class of polypeptides that is able to bind to a specific molecular antigen. An antibody is typically composed of two identical pairs of polypeptide chains, wherein each pair has one heavy chain (about 50-70 kDa) and one light chain (about 25 kDa); and wherein the amino-terminal portion of the heavy and light chains includes a variable region of about 100 to about 130 or more amino acids and the carboxy-terminal portion of each chain includes a constant region (See, Borrebaeck (ed.), 1995, *Antibody Engineering*, Second Ed., Oxford University Press.; Kuby, 1997, *Immunology*, Third Ed., W.H. Freeman and Company, New York). In specific embodiments, the specific molecular antigen bound by an antibody provided herein includes an ICP antigen polypeptide, an ICP peptide fragment, or an ICP epitope. The ICP polypeptide, ICP peptide fragment, or ICP epitope can be unglycosylated or glycosylated. In a particular embodiment, the ICP polypeptide, ICP peptide fragment, or ICP epitope is glycosylated, An antibody or a peptide fragment thereof that binds to a ICP antigen can be identified, for example, by immunoassays, BIAcore, or other techniques known to those of skill in the art, and as described in the examples herein. An antibody or a fragment thereof binds specifically to an ICP antigen when it binds to the ICP antigen with higher affinity than to any cross-reactive antigen as determined using experimental techniques, such as radioimmunoassays (RIA) and enzyme linked immunosorbent assays (ELISAs). Typically, a specific or selective binding reaction will be at least twice background signal or noise, and more typically more than 5-10 times background signal or noise. See, e.g., Paul, ed., 1989, *Fundamental Immunology Second Edition*, Raven Press, New York at pages 332-336 for a discussion regarding antibody specificity.

Antibodies provided herein include, but are not limited to, synthetic antibodies, monoclonal antibodies, recombinantly produced antibodies, multispecific antibodies (including bi-specific antibodies), human antibodies, humanized antibodies, camelized antibodies, chimeric antibodies, intrabodies, anti-idiotypic (anti-Id) antibodies, and functional fragments (e.g., antigen-binding fragments such as glycosylated ICP binding fragments) of any one of the above. A binding fragment refers a portion of an antibody heavy or light chain polypeptide, such as a peptide portion, that retains some or all of the binding activity of the antibody from which the fragment is derived. Non-limiting examples of functional fragments (e.g., antigen-binding fragments such as ICP binding fragments) include single-chain Fvs (scFv) (e.g., including monospecific, bispecific, biparatopic, monovalent (e.g., with a single $V_H$ or $V_L$ domain) or bivalent, etc.), Fab fragments, F(ab') fragments, F(ab)$_2$ fragments, F(ab')$_2$ fragments, disulfide-linked Fvs (sdFv), Fd fragments, Fv fragments, diabodies, triabodies, tetrabodies and minibodies. In particular, antibodies provided herein include immunoglobulin molecules and immunologically active portions of immunoglobulin molecules, for example, antigen binding domains or molecules that contain an antigen-binding site that binds to an ICP antigen, in particular, a glycosylated ICP antigen, (e.g., one or more complementarity determining regions (CDRs) of an anti-glycosylated ICP antibody). Description of such antibody fragments can be found in, for example, Harlow and Lane, *Antibodies: A Laboratory Manual*, Cold Spring Harbor Laboratory, New York (1989); Myers (ed.), *Molec. Biology and Biotechnology: A Comprehensive Desk Reference*, New York: VCH Publisher, Inc.; Huston et al., *Cell Biophysics*, 22:189-224 (1993); Plückthun and Skerra, *Meth. Enzymol.*, 178:497-515 (1989) and in Day, E. D., *Advanced Immunochemistry*, Second Ed., Wiley-Liss, Inc., New York, NY (1990). The antibodies provided herein can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule. Anti-PD-L1 antibodies can be agonistic antibodies or antagonistic antibodies. In certain embodiments, the anti-ICP antibodies are fully human, such as fully human monoclonal anti-ICP antibodies. In certain embodiments, the anti-ICP antibodies are humanized, such as humanized monoclonal anti-glycICP antibodies. In certain embodiments, the antibodies provided herein are IgG antibodies, or a class (e.g., human IgG1 or IgG4) or subclass thereof, in particular, IgG1 subclass antibodies.

A four-chain antibody unit is a heterotetrameric glycoprotein composed of two identical light (L) chains and two identical heavy (H) chains. In the case of IgGs, the molecular weight of the four-chain (unreduced) antibody unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. At the N-terminus, each H chain has a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its carboxy terminus. The $V_L$ domain is aligned with the $V_H$ domain, and the $C_L$ domain is aligned with the first constant domain of the heavy chain ($C_{H1}$). Particular amino acid residues are believed to form an interface between the light chain and heavy chain variable domains. The pairing of a $V_H$ and $V_L$ together forms a single antigen-binding site. The basic structure of immunoglobulin molecules is understood by those having skill in the art. For example, the structure and properties of the different classes of antibodies may be found in *Basic and Clinical Immunology*, 8th edition, Daniel P. Stites, Abba I. Terr and Tristram G. Parslow (eds.), Appleton & Lange, Norwalk, CT, 1994, page 71 and Chapter 6.

As used herein, the term "antigen" or "target antigen" is a predetermined molecule to which an antibody can selectively bind. A target antigen can be a polypeptide, peptide, carbohydrate, nucleic acid, lipid, hapten, or other naturally occurring or synthetic compound. In embodiments, a target antigen is a small molecule. In certain embodiments, the target antigen is a polypeptide or peptide, preferably a glycosylated ICP.

As used herein, the term "antigen binding fragment," "antigen binding domain," "antigen binding region," and similar terms refer to that portion of an antibody which includes the amino acid residues that interact with an antigen and confer on the antibody as binding agent its specificity and affinity for the antigen (e.g., the CDRs of an antibody are antigen binding regions). The antigen binding region can be derived from any animal species, such as rodents (e.g., rabbit, rat, or hamster) and humans. In specific embodiments, the antigen binding region can be of human origin.

An "isolated" antibody is substantially free of cellular material or other contaminating proteins from the cell or tissue source and/or other contaminant components from which the antibody is derived, or is substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of an antibody that have less than about 30%, 25%, 20%, 15%, 10%, 5%, or 1% (by dry weight) of heterologous protein (also referred to herein as a "contaminating protein"). In certain embodiments, when the antibody is recombinantly produced, it is substantially free of culture medium, e.g., culture medium represents less than about 20%, 15%, 10%, 5%, or 1% of the volume of the protein preparation. In certain embodiments, when the antibody is produced by chemical synthesis, it is substantially free of chemical precursors or other chemicals, for example, it is separated from chemical precursors or other chemicals which are involved in the synthesis of the protein. Accordingly such preparations of the antibody have less than about 30%, 25%, 20%, 15%, 10%, 5%, or 1% (by dry weight) of chemical precursors or compounds other than the antibody of interest. Contaminant components can also include, but are not limited to, materials that would interfere with therapeutic uses for the antibody, and can include enzymes, hormones, and other proteinaceous or nonproteinaceous solutes. In certain embodiments, the antibody is purified (1) to greater than or equal to 95% by weight of the antibody, as determined by the Lowry method (Lowry et al. J. Bio. Chem. 193: 265-275, 1951), such as 95%, 96%, 97%, 98%, or 99%, by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody also includes the antibody in situ within recombinant cells since at least one component of the antibody's natural environment will not be present. An isolated antibody is typically prepared by at least one purification step. In some embodiments, the antibodies provided herein are isolated.

As used herein, the term "binds" or "binding" refers to an interaction between molecules including, for example, to form a complex. Illustratively, such interactions embrace non-covalent interactions, including hydrogen bonds, ionic bonds, hydrophobic interactions, and/or van der Waals interactions. A complex can also include the binding of two or more molecules held together by covalent or non-covalent bonds, interactions, or forces. The strength of the total non-covalent interactions between a single antigen-binding site of an antibody and its epitope on a target (antigen) molecule, such as PD-L1 or PD-1, is the affinity of the antibody or functional fragment for that epitope. The ratio of association ($k_{on}$) to dissociation ($k_{off}$) of an antibody to a monovalent antigen ($k_{on}/k_{off}$) is the association constant K, which is a measure of affinity. The value of K varies for different complexes of antibody and antigen and depends on both $k_{on}$ and $k_{off}$. The association constant K for an antibody provided herein may be determined using any method provided herein or any other method known to those skilled in the art. The affinity at one binding site does not always reflect the true strength of the interaction between an antibody and an antigen. When complex antigens containing multiple, repeating antigenic determinants come into contact with antibodies containing multiple binding sites, the interaction of antibody with antigen at one site will increase the probability of an interaction at a second binding site. The strength of such multiple interactions between a multivalent antibody and antigen is called the avidity. The avidity of an antibody can be a better measure of its binding capacity than is the affinity of its individual binding sites. For example, high avidity can compensate for low affinity as is sometimes found for pentameric IgM antibodies, which can have a lower affinity than IgG, but the high avidity of IgM, resulting from its multivalence, enables it to bind antigen effectively.

"Binding affinity" generally refers to the strength of the sum total of noncovalent interactions between a single binding site of a molecule (e.g., a binding protein such as an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a binding molecule X for its binding partner Y can generally be represented by the dissociation constant ($K_d$). Affinity can be measured by common methods known in the art, including those described herein. Low-affinity antibodies generally bind antigen slowly and tend to dissociate readily, while high-affinity antibodies generally bind antigen faster and tend to remain bound longer to antigen. A variety of methods for measuring binding affinity are known in the art, any of which may be used for purposes of the present disclosure. Specific illustrative embodiments include the following: In one embodiment, the "$K_d$" or "$K_d$ value" is measured by assays known in the art, for example, by a binding assay. The $K_d$ can be measured in a radiolabeled antigen binding assay (MA), for example, performed with the Fab portion of an antibody of interest and its antigen (Chen, et al., (1999) J. Mol Biol 293:865-881). The $K_d$ or $K_d$ value may also be measured by using surface plasmon resonance assays (by BIAcore) using, for example, a BIAcore™-2000 or a BIAcore™-3000 (BIAcore, Inc., Piscataway, NJ), or by biolayer interferometry using, for example, the OctetQK384 system (ForteBio, Menlo Park, CA). An "on-rate" or "rate of association" or "association rate" or "$k_{on}$" can also be determined with the same surface plasmon resonance or biolayer interferometry techniques described above, using, for example, a BIAcore™-2000 or a BIAcore™-3000 (BIAcore, Inc., Piscataway, NJ), or the OctetQK384 system (ForteBio, Menlo Park, CA).

The terms "anti-glycICP antibody," "an antibody that specifically binds to a glycosylated ICP," or "antibody that is specific for a glycosylated ICP," "antibodies that specifically bind to a glycosylated ICP epitope," "an antibody that selectively binds to a glycosylated ICP," "antibodies that selectively bind to a glycosylated ICP epitope," "antibodies that preferentially bind to a glycosylated ICP epitope and analogous terms are used interchangeably herein and refer to antibodies capable of binding an ICP, i.e., glycosylated or WT ICP, with sufficient affinity and specificity. The anti-glycosylated ICP antibodies specifically bind to a glycosylated ICP polypeptide, such as a glycosylated ICP antigen, peptide fragment, or epitope (e.g., human PD-L1 such as a human PD-L1 polypeptide, antigen or epitope). "Preferential binding" of the anti-glycICP antibodies as provided herein may be determined based on the quantification of fluorescence intensity of the antibodies' binding to the glycosylated ICP expressed on cells versus an appropriate control, such as binding to cells expressing a non-glycosylated form of ICP, for example, as described in Example 2 herein for antibodies that preferentially bind to glycosylated PD-L1. Preferential binding of an anti-ICP antibody as described to a glycosylated ICP polypeptide or to a glycosylated ICP-expressing cell is indicated by a measured fluorescent binding intensity (MFI) value using the assay as described in Example 2 of at least 1.5-fold, at least 2-fold, at least 3-fold, at least 4-fold, at least 5-fold, at least 6-fold, at least 7-fold, at least 8-fold, at least 10-fold, at least 15-fold, at least 20-fold or greater, as compared with binding of the antibody to a non-glycosylated ICP polypeptide or a non-glycosylated ICP-expressing cell. In embodiments, an anti-glycICP antibody that preferentially or selectively binds glycosylated ICP exhibits an MFI value of from 1.5-fold to 25-fold, or from 2-fold to 20-fold, or from 3-fold to 15-fold, or from 4-fold to 8-fold, or from 2-fold to 10-fold, or from 2-fold to 5-fold greater for binding cells expressing the glycosylated form of the ICP than the MFI value of the same antibody for binding cells expressing a non-glycosylated form of the ICP or an ICP glycosylation variant which is not fully glycosylated, as determined, for example according to the flow cytometry assay in Example 2. Fold-fluorescence intensity values between and equal to all of the foregoing are intended to be included.

In embodiments, an antibody that specifically binds to a human glycosylated ICP (e.g., human PD-L1) can bind to the extracellular domain (ECD) comprising at least one N-linked glycosylated amino acid, or a peptide derived from the ECD of glycosylated ICP. An antibody that specifically binds to a human glycosylated ICP antigen (e.g., human PD-L1) can be cross-reactive with related antigens (e.g., cynomolgus (cyno) ICP antigens). In a preferred embodiment, an antibody that specifically binds to a human glycosylated ICP antigen does not cross-react with other ICP antigens. An antibody that specifically binds to a human glycosylated ICP antigen can be identified, for example, by immunoassay methods, Biacore, or other techniques known to those of skill in the art. In certain embodiments, an antibody that binds to a human glycosylated ICP, as described herein, has a dissociation constant ($K_d$) of less than or equal to 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 0.9 nM, 0.8 nM, 0.7 nM, 0.6 nM, 0.5 nM, 0.4 nM, 0.3 nM, 0.2 nM, or 0.1 nM, and/or is greater than or equal to 0.1 nM. In certain embodiments, an antibody that binds to a glycosylated ICP binds to an epitope of that protein which is conserved among the ICPs from different species (e.g., between human and cyno PD-L1). An antibody binds specifically to glycosylated ICP antigen when it binds to the glycosylated ICP with higher affinity than to any cross reactive antigen as determined using experimental techniques, such as radioimmunoassays (MA) and enzyme linked immunosorbent assays (ELISAs). Typically a specific or selective reaction will be at least twice background signal or noise and can be more than 10 times background. See, e.g., Paul, ed., 1989, *Fundamental Immunology Second Edition,* Raven Press, New York at pages 332 336, for a discussion regarding antibody specificity. In such embodiments, the extent of binding of the antibody to a "non-target" protein will be less than about 10% of the binding of the antibody to its particular target protein, for example, as determined by fluorescence activated cell sorting (FACS) analysis or radioimmunoprecipitation (MA).

In embodiments, anti-glycosylated ICP antibodies include antibodies which are specific for glycosylated ICPs, for example, anti-glycosylated ICP antibodies or anti-wild type ICP (ICP WT) antibodies, wherein the wild type ICP protein is glycosylated, include antibodies which are specific for glycosylated ICP. In preferred embodiments, the anti-glycosylated ICP antibodies specifically and preferentially bind glycosylated versus non-glycosylated ICP. In some embodiments, the anti-glycosylated ICP antibodies bind to a linear glycosylation motif of the ICP. In some embodiments, the anti-glycosylated ICP antibodies bind to a peptide sequence that is located near one or more of the glycosylation motifs in three dimensions. In some embodiments, the anti-glycosylated ICP antibodies selectively bind to one or more glycosylation motifs of the ICP or a peptide thereof having a glycosylation motif relative to an unglycosylated ICP. In other embodiments, the anti-glycosylated ICP antibodies bind to a linear epitope comprising contiguous amino acids of the ICP amino acid sequence. In yet other embodiments, the anti-glycosylated ICP antibodies bind to a conformational (nonlinear) epitope comprising non-contiguous amino acids of the glycosylated ICP. In some embodiments, an anti-glycosylated ICP antibody, or a binding portion thereof, binds to a glycosylated ICP with a $K_d$ less than at least 30%, 40%, 50%, 60%, 70%, 80%, or 90% of the $K_d$ exhibited relative to unglycosylated ICP. In certain embodiments, an anti-glycosylated ICP antibody, or a binding portion thereof, binds to a glycosylated ICP with a $K_d$ less than 50% of the Kd exhibited relative to unglycosylated ICP. In some embodiments, an anti-glycosylated ICP antibody, or a binding portion thereof, binds to glycosylated ICP with a $K_d$ that is less than 1%, 2%, 3%, 4%, 5%, 6%, 7%, 8%, 9%, 10%, 15%, 20%, 30%, 40%, 50% of the $K_d$ exhibited relative to unglycosylated ICP. In further aspects, an anti-glycosylated ICP antibody, or a binding portion thereof, binds to glycosylated ICP with a $K_d$ at least 5-10 times less than the $K_d$ exhibited relative to unglycosylated ICP. In an embodiment, an anti-ICP antibody, or a binding portion thereof, binds to glycosylated ICP with a $K_d$ at least 10 times less than the $K_d$ exhibited relative to unglycosylated ICP. In certain embodiments, the antibody binds to glycosylated ICP with a $K_d$ that is no more than 1%, 2%, 3%, 4%, 5%, 6%, 7%, 8%, 9%, 10%, 15%, or 20% of the $K_d$ exhibited by binding to the unglycosylated form of the ICP. In an embodiment, an anti-ICP antibody, or a binding portion thereof, binds to glycosylated ICP with a nanomolar affinity, such as an affinity of from 5-20 nM or from 10-20 nM, inclusive of the lower and upper values.

As used herein in reference to an antibody, the term "heavy (H) chain" refers to a polypeptide chain of about 50-70 kDa, wherein the amino-terminal portion includes a variable (V) region (also called V domain) of about 115 to 130 or more amino acids and a carboxy-terminal portion that includes a constant (C) region. The constant region (or constant domain) can be one of five distinct types, (e.g., isotypes) referred to as alpha (α), delta (δ), epsilon (ε), gamma (γ) and mu (μ), based on the amino acid sequence of the heavy chain constant region. The distinct heavy chains differ in size: α, δ and γ contain approximately 450 amino acids, while μ and ε contain approximately 550 amino acids. When combined with a light chain, these distinct types of heavy chains give rise to five well known classes (e.g., isotypes) of antibodies, namely, IgA, IgD, IgE, IgG and IgM, respectively, including four subclasses of IgG, namely IgG1, IgG2, IgG3 and IgG4. An antibody heavy chain can be a human antibody heavy chain.

As used herein in reference to an antibody, the term "light (L) chain" refers to a polypeptide chain of about 25 kDa, wherein the amino-terminal portion includes a variable domain of about 100 to about 110 or more amino acids and a carboxy-terminal portion that includes a constant region. The approximate length of a light chain (both the V and C domains) is 211 to 217 amino acids. There are two distinct types of light chains, referred to as kappa (κ) and lambda (λ), based on the amino acid sequence of the constant domains. Light chain amino acid sequences are well known in the art. An antibody light chain can be a human antibody light chain.

As used herein, the term "variable (V) region" or "variable (V) domain" refers to a portion of the light (L) or heavy (H) chains of an antibody polypeptide that is generally located at the amino-terminus of the L or H chain. The H chain V domain has a length of about 115 to 130 amino acids, while the L chain V domain is about 100 to 110 amino acids in length. The H and L chain V domains are used in the binding and specificity of each particular antibody for its particular antigen. The V domain of the H chain can be referred to as "$V_H$." The V region of the L chain can be referred to as "$V_L$." The term "variable" refers to the fact that certain segments of the V domains differ extensively in sequence among different antibodies. While the V domain mediates antigen binding and defines specificity of a particular antibody for its particular antigen, the variability is not evenly distributed across the 110-amino acid span of antibody V domains. Instead, the V domains consist of less variable (e.g., relatively invariant) stretches called framework regions (FRs) of about 15-30 amino acids separated by shorter regions of greater variability (e.g., extreme variability) called "hypervariable regions" or "complementarity determining regions" (CDRs) that are each about 9-12 amino acids long. The V domains of antibody H and L chains each comprise four FRs, largely adopting a β sheet configuration, connected by three hypervariable regions, called, which form loops connecting, and in some cases forming part of, the β sheet structure. The hypervariable regions in each chain are held together in close proximity by the FRs and, with the hypervariable regions from the other chain, contribute to the formation of the antigen-binding site of antibodies (see, e.g., Kabat et al., Sequences of Proteins of Immunological Interest, 5th Ed. Public Health Service, National Institutes of Health, Bethesda, MD, 1991)). The C domains are not involved directly in binding an antibody to an antigen, but exhibit various effector functions, such as antibody dependent cellular cytotoxicity (ADCC) and complement dependent cytotoxicity (CDC). The V domains differ extensively in sequence among different antibody classes or types. The variability in sequence is concentrated in the CDRs, which are primarily responsible for the interaction of the antibody with antigen. In specific embodiments, the variable domain of an antibody is a human or humanized variable domain.

As used herein, the terms "complementarity determining region," "CDR," "hypervariable region," "HVR," and "HV" are used interchangeably. A "CDR" refers to one of three hypervariable regions (H1, H2 or H3) within the non-framework region of the antibody $V_H$ β-sheet framework, or to one of three hypervariable regions (L1, L2 or L3) within the non-framework region of the antibody $V_L$ β-sheet framework. The term, when used herein, refers to the regions of an antibody V domain that are hypervariable in sequence and/or form structurally defined loops. Generally, antibodies comprise six hypervariable regions: three (H1, H2, H3) in the $V_H$ domain and three (L1, L2, L3) in the $V_L$ domain. Accordingly, CDRs are typically highly variable sequences interspersed within the framework region sequences of the V domain. "Framework" or "FR" residues are those variable region residues flanking the CDRs. FR residues are present, for example, in chimeric, humanized, human, domain antibodies, diabodies, linear antibodies, bispecific, or biparatopic antibodies.

A number of hypervariable region delineations are in use and are encompassed herein. CDR regions are well known to those skilled in the art and have been defined by, for example, Kabat as the regions of most hypervariability within the antibody V domains (Kabat et al., J. Biol. Chem. 252:6609-6616 (1977); Kabat, Adv. Prot. Chem. 32:1-75 (1978)). The Kabat CDRs are based on sequence variability and are the most commonly used (see, e.g., Kabat et al., Sequences of Proteins of Immunological Interest, 5th Ed. Public Health Service, National Institutes of Health, Bethesda, MD (1991)). CDR region sequences also have been defined structurally by Chothia as those residues that are not part of the conserved β-sheet framework, and thus are able to adopt different conformations (Chothia and Lesk, J. Mol. Biol. 196:901-917 (1987)). Chothia refers instead to the location of the structural loops. The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). Both numbering systems and terminologies are well recognized in the art.

Recently, a universal numbering system has been developed and widely adopted, ImMunoGeneTics (IMGT) Information System® (Lafranc et al., Dev. Comp. Immunol. 27(1):55-77 (2003)). IMGT is an integrated information system specializing in immunoglobulins (Ig), T cell receptors (TR) and the major histocompatibility complex (MHC) of human and other vertebrates. Herein, the CDRs are referred to in terms of both the amino acid sequence and the location within the light or heavy chain. As the "location" of the CDRs within the structure of the immunoglobulin V domain is conserved between species and present in structures called loops, by using numbering systems that align variable domain sequences according to structural features, CDR and framework residues and are readily identified. This information can be used in grafting and in the replacement of CDR residues from immunoglobulins of one species into an acceptor framework from, typically, a human antibody. An additional numbering system (AHon) has been developed by Honegger and Plückthun, J. Mol. Biol. 309: 657-670 (2001). Correspondence between the numbering system, including, for example, the Kabat numbering and the IMGT unique numbering system, is well known to one skilled in the art (see, e.g., Kabat, supra; Chothia and Lesk, supra; Martin, supra; and Lefranc et al., 1999, Nuc. Acids Res., 27:209-212).

CDR region sequences have also been defined by AbM, Contact and IMGT. The AbM hypervariable regions represent a compromise between the Kabat CDRs and Chothia structural loops, and are used by Oxford Molecular's AbM antibody modeling software (see, e.g., Martin, in Antibody Engineering, Vol. 2, Chapter 3, Springer Verlag). The "contact" hypervariable regions are based on an analysis of the available complex crystal structures. The residues from each of these hypervariable regions or CDRs are noted below.

Exemplary delineations of CDR region sequences are illustrated in Table 3 below. The positions of CDRs within a canonical antibody variable region have been determined by comparison of numerous structures (Al-Lazikani et al., J. Mol. Biol. 273:927-948 (1997); Morea et al., Methods 20:267-279 (2000)). Because the number of residues within a hypervariable region varies in different antibodies, additional residues relative to the canonical positions are conventionally numbered with a, b, c and so forth next to the residue number in the canonical variable region numbering scheme (Al-Lazikani et al., supra (1997)). Such nomenclature is similarly well known to those skilled in the art.

TABLE 3

Exemplary Delineations of CDR Region Sequences

| | IMGT | Kabat | AbM | Chothia | Contact |
|---|---|---|---|---|---|
| $V_H$ CDR1 | 27-38 | 31-35 | 26-35 | 26-32 | 30-35 |
| $V_H$ CDR2 | 56-65 | 50-65 | 50-58 | 53-55 | 47-58 |
| $V_H$ CDR3 | 105-117 | 95-102 | 95-102 | 96-101 | 93-101 |
| $V_L$ CDR1 | 27-38 | 24-34 | 24-34 | 26-32 | 30-36 |
| $V_L$ CDR2 | 56-65 | 50-56 | 50-56 | 50-52 | 46-55 |
| $V_L$ CDR3 | 105-117 | 89-97 | 89-97 | 91-96 | 89-96 |

An "affinity matured" antibody is one with one or more alterations (e.g., amino acid sequence variations, including changes, additions and/or deletions) in one or more HVRs thereof that result in an improvement in the affinity of the antibody for antigen, compared to a parent antibody which does not possess those alteration(s). In certain embodiments, affinity matured antibodies will have nanomolar or even picomolar affinities for the target antigen, such as the glycosylated PD-L1. Affinity matured antibodies are produced by procedures known in the art. For reviews, see Hudson and Souriau, Nature Medicine 9:129-134 (2003); Hoogenboom, Nature Biotechnol. 23: 1105-1116 (2005); Quiroz and Sinclair, Revista Ingeneria Biomedia 4: 39-51 (2010).

A "chimeric" antibody is one in which a portion of the H and/or L chain, e.g., the V domain, is identical with or homologous to a corresponding amino acid sequence in an antibody derived from a particular species or belonging to a particular antibody class or subclass, while the remainder of the chain(s), e.g., the C domain, is identical with or homologous to corresponding sequences in antibodies derived from another species or belonging to another antibody class or subclass, as well as a fragment of such an antibody, so long as it exhibits the desired biological activity (see, e.g., U.S. Pat. No. 4,816,567; and Morrison et al., Proc. Natl. Acad. Sci. USA, 81:6851-6855 (1984)).

A "humanized" nonhuman (e.g., murine) antibody is a chimeric form of an antibody that refers to a human immunoglobulin sequence (e.g., recipient antibody) in which the native CDR residues are replaced by residues from the corresponding CDRs of a nonhuman species (e.g., donor antibody) such as mouse, rat, rabbit or nonhuman primate having the desired specificity, affinity, and capacity for antigen binding and interaction. In some instances, one or more FR region residues of the human immunoglobulin may also be replaced by corresponding nonhuman residues. In addition, humanized antibodies can comprise residues that are not found in the recipient antibody or in the donor antibody. These modifications are made to further refine the humanized antibody's performance. A humanized antibody H or L chain may comprise substantially all of at least one or more variable regions, in which all or substantially all of the CDRs correspond to those of a nonhuman immunoglobulin and all or substantially all of the FRs are those of a human immunoglobulin sequence. In certain embodiments, the humanized antibody will comprise at least a portion of an immunoglobulin constant region (Fc), typically that of a human immunoglobulin. While known to those skilled in the art, further details may be found, if desired, in, e.g., Jones et al., Nature, 321:522-525 (1986); Riechmann et al., Nature, 332:323-329 (1988); and Presta, Curr. Op. Struct. Biol., 2:593-596 (1992); Carter et al., Proc. Natl. Acad. Sci. USA, 89:4285-4289 (1992); and U.S. Pat. No. 6,800,738 (issued Oct. 5, 2004), U.S. Pat. No. 6,719,971 (issued Sep. 27, 2005), U.S. Pat. No. 6,639,055 (issued Oct. 28, 2003), U.S. Pat. No. 6,407,213 (issued Jun. 18, 2002), and U.S. Pat. No. 6,054,297 (issued Apr. 25, 2000).

The terms "human antibody" and "fully human antibody" are used interchangeably herein and refer to an antibody that possesses an amino acid sequence which corresponds to that of an antibody produced by a human and/or has been made using any of the techniques for making human antibodies as practiced by those skilled in the art. This definition of a human antibody specifically excludes a humanized antibody comprising non-human antigen-binding residues. Human antibodies can be produced using various techniques known in the art, including phage-display libraries (Hoogenboom and Winter, J. Mol. Biol., 227:381 (1991); Marks et al., J. Mol. Biol., 222:581 (1991) and yeast display libraries (Chao et al., Nature Protocols 1: 755-768 (2006)). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also, van Dijk and van de Winkel, Curr. Opin. Pharmacol., 5: 368-74 (2001). Human antibodies can be prepared by administering an antigen to a transgenic animal whose endogenous Ig loci have been disabled, e.g., a mouse, and that has been genetically modified to harbor human immunoglobulin genes which encode human antibodies, such that human antibodies are generated in response to antigenic challenge (see, e.g., Jakobovits, A., Curr. Opin. Biotechnol. 1995, 6(5):561-6; Bruggemann and Taussing, Curr. Opin. Biotechnol. 1997, 8(4):455-8; and U.S. Pat. Nos. 6,075,181 and 6,150,584 regarding XENOMOUSE™ technology). See also, for example, Li et al., Proc. Natl. Acad. Sci. USA, 103:3557-3562 (2006) regarding human antibodies generated via a human B-cell hybridoma technology. In specific embodiments, human antibodies comprise a variable region and constant region of human origin. "Fully human" anti-glycosylated ICP antibodies, in certain embodiments, can also encompass antibodies which bind immune checkpoint polypeptides and are encoded by nucleic acid sequences which are naturally occurring somatic variants of human germline immunoglobulin nucleic acid sequence. In a specific embodiment, the anti-glycosylated ICP antibodies provided herein are fully human antibodies. The term "fully human antibody" includes antibodies having variable and constant regions corresponding to human germline immunoglobulin sequences as described by Kabat et al. (See Kabat, et al., 1991, Sequences of Proteins of Immunological Interest, Fifth Edition, U.S. Department of Health and Human Services, NIH Publication No. 91-3242). The phrase "recombinant human antibody" includes human antibodies that are prepared, expressed, created, or isolated by recombinant means, such as antibodies expressed using a recombinant expression vector transfected into a host cell; antibodies isolated from a recombinant, combinatorial human antibody library; antibodies isolated from an animal (e.g., a mouse or cow) that is transgenic and/or transchromosomal for human immunoglobulin genes (see e.g., Taylor, L. D., et al. (1992) Nucl. Acids Res. 20:6287-6295); or antibodies prepared, expressed, created or isolated by any other means that involves splicing of human immunoglobulin gene sequences to other DNA sequences. Such recombinant human antibodies can have variable and constant regions derived from human germline immunoglobulin sequences (See, Kabat, E. A., et al., 1991, Id). In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, the term "epitope" is the site(s) or region(s) on the surface of an antigen molecule to which a single antibody molecule binds, such as a localized region on the surface of an antigen, e.g., a ICP polypeptide or a glycosylated ICP polypeptide that is capable of being bound by one or more antigen binding regions of an anti-ICP or anti-glycICP antibody. An epitope can be immunogenic and capable of eliciting an immune response in an animal. Epitopes need not necessarily be immunogenic. Epitopes often consist of chemically active surface groupings of molecules such as amino acids or sugar side chains and have specific three dimensional structural characteristics as well as specific charge characteristics. An epitope can be a linear epitope and a conformational epitope. A region of a polypeptide contributing to an epitope can be contiguous amino acids of the polypeptide, forming a linear epitope, or the epitope can be formed from two or more non-contiguous amino acids or regions of the polypeptide, typically called a conformational epitope. The epitope may or may not be a three-dimensional surface feature of the antigen. In certain embodiments, a glycosylated immune checkpoint polypeptide epitope is a three-dimensional surface feature of a glycosylated immune checkpoint polypeptide. In other embodiments, a glycosylated immune checkpoint polypeptide epitope is linear surface feature of a glycosylated immune checkpoint polypeptide. In some embodiments, the immune checkpoint polypeptide epitope is unglycosylated immune checkpoint polypeptide. In some embodiments, the glycosylated immune checkpoint polypeptide epitope is glycosylated at one or more sites. Generally an antigen has several or many different epitopes and can react with many different antibodies. In a particular embodiment, an antiglycosylated immune checkpoint polypeptide antibody binds an epitope of a glycosylated immune checkpoint polypeptide, for example, glycosylated PD-L1, that is a conformational epitope.

An antibody binds "an epitope" or "essentially the same epitope" or "the same epitope" as a reference antibody, when the two antibodies recognize identical, overlapping, or adjacent epitopes in a three-dimensional space. The most widely used and rapid methods for determining whether two antibodies bind to identical, overlapping, or adjacent epitopes in a three-dimensional space are competition assays, which can be configured in a number of different formats, for example, using either labeled antigen or labeled antibody. In some assays, the antigen is immobilized on a 96-well plate, or expressed on a cell surface, and the ability of unlabeled antibodies to block the binding of labeled antibodies to antigen is measured using a detectable signal, e.g., radioactive, fluorescent or enzyme labels.

The term "compete" when used in the context of antiglycosylated immune checkpoint polypeptide antibodies that compete for the same epitope or binding site on a glycosylated immune checkpoint polypeptide target protein or peptide thereof means competition as determined by an assay in which the antibody under study, or binding fragment thereof, prevents, blocks, or inhibits the specific binding of a reference molecule (e.g., a reference ligand, or reference antigen binding protein, such as a reference antibody) to a common antigen (e.g., an ICP or a fragment thereof). Numerous types of competitive binding assays can be used to determine if a test antibody competes with a reference antibody for binding to a glycosylated immune checkpoint polypeptide or epitope thereof (e.g., human PD-L1 or human glycosylated PD-L1). Examples of assays that can be employed include solid phase direct or indirect radioimmunoassay (MA); solid phase direct or indirect enzyme immunoassay (EIA); sandwich competition assay (see, e.g., Stahli et al., (1983) *Methods in Enzymology* 9:242-253); solid phase direct biotin-avidin EIA (see, e.g., Kirkland et al., (1986) *J. Immunol.* 137:3614-3619); solid phase direct labeled assay; solid phase direct labeled sandwich assay (see, e.g., Harlow and Lane, (1988) *Antibodies, A Laboratory Manual*, Cold Spring Harbor Press); solid phase direct label MA using labeled iodine ($1^{125}$ label) (see, e.g., Morel et al., (1988) *Molec. Immunol.* 25:7-15); solid phase direct biotin-avidin EIA (see, e.g., Cheung, et al., (1990) *Virology* 176:546-552); and direct labeled MA (Moldenhauer et al., (1990) *Scand. J. Immunol.* 32:77-82). Typically, such an assay involves the use of a purified, glycosylated ICP antigen (e.g., human PD-L1 or glycosylated PD-L1) bound to a solid surface, or cells bearing either of an unlabeled test antigen binding protein (e.g., test anti-PD-L1 antibody) or a labeled reference antigen binding protein (e.g., reference anti-PD-L1 antibody). Competitive inhibition can be measured by determining the amount of label bound to the solid surface or cells in the presence of a known amount of the test antigen binding protein. Usually the test antigen binding protein is present in excess. Antibodies identified by competition assay (competing antibodies) include antibodies binding to the same epitope as the reference antibody and/or antibodies binding to an adjacent epitope sufficiently proximal to the epitope bound by the reference antibody so as to cause steric hindrance to occur. Additional details regarding methods for determining competitive binding are described herein. Usually, when a competing antibody protein is present in excess, it will inhibit specific binding of a reference antibody to a common antigen by at least 15%, or at least 23%, for example, without limitation, 40%, 45%, 50%, 55%, 60%, 65%, 70% or 75% or greater, as well as percent amounts between the amounts stated. In some instance, binding is inhibited by at least 80%, 85%, 90%, 95%, 96% or 97%, 98%, 99% or more.

As used herein, the term "blocking" antibody or an "antagonist" antibody refers to an antibody that prevents, inhibits, blocks, or reduces biological or functional activity of the antigen to which it binds. Blocking antibodies or antagonist antibodies can substantially or completely prevent, inhibit, block, or reduce the biological activity or function of the antigen. For example, a blocking antiglycosylated immune checkpoint polypeptide antibody can prevent, inhibit, block, or reduce the binding interaction between two ICPs that interact, e.g., PD-L1 and PD-1, thus preventing, blocking, inhibiting, or reducing the immunosuppressive functions associated with the interaction. The terms block, inhibit, and neutralize are used interchangeably herein and refer to the ability of anti-glycosylated immune checkpoint polypeptide antibodies to prevent or otherwise disrupt the ICP-ICP interaction.

As used herein, the term "polypeptide" or "peptide" refers to a polymer of amino acids of three or more amino acids in a serial array, linked through peptide bonds. "Polypeptides" can be proteins, protein fragments, protein analogs, oligopeptides and the like. The amino acids that comprise the polypeptide may be naturally derived or synthetic. The polypeptide may purified from a biological sample. For example, an ICP polypeptide or peptide may be composed of at least 3, 4, 5, 6, 7, 8, 9, 10, 11, 12, 13, 14, 15, 16, 17, 18, 19, 20, 21, 22, 23, 24, or 25 contiguous amino acids of the amino acid sequence of the ICP. In some embodiments, the polypeptide has at least 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, 210, 220, 230, 240, 250, 260, 270, 280, or 285 contiguous amino acids of a human immune checkpoint polypeptide or glycosylated immune checkpoint polypeptide. In certain embodiments, the glycosylated or un glycosylated immune checkpoint polypeptide comprises at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, at least 250 contiguous amino acid residues of the amino acid sequence of an immune checkpoint polypeptide or a glycosylated immune checkpoint.

As used herein, the term "analog" refers to a polypeptide that possesses a similar or identical function as a reference polypeptide but does not necessarily comprise a similar or identical amino acid sequence of the reference polypeptide, or possess a similar or identical structure of the reference polypeptide. The reference polypeptide may be an ICP, e.g., a PD-L1 polypeptide, a fragment of an ICP, an anti-ICP antibody, or an anti-glycosylated ICP antibody. A polypeptide that has a similar amino acid sequence with a reference polypeptide refers to a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of the reference polypeptide, which can be an ICP or an anti-glycosylated ICP antibody as described herein. A polypeptide with similar structure to a reference polypeptide refers to a polypeptide that has a secondary, tertiary or quaternary structure similar to that of the reference polypeptide, which can be an ICP or an anti-glycosylated ICP antibody. The structure of a polypeptide can be determined by methods known to those skilled in the art, including, but not limited to, X-ray crystallography, nuclear magnetic resonance (NMR), and crystallographic electron microscopy.

As used herein, the term "variant" when used in relation to an ICP or to an anti-glycosylated ICP antibody, refers to a polypeptide or an anti-glycosylated ICP antibody having one or more (such as, for example, about 1 to about 25, about 1 to about 20, about 1 to about 15, about 1 to about 10, or about 1 to about 5) amino acid sequence substitutions, deletions, and/or additions as compared to a native or unmodified ICP sequence or anti-ICP antibody sequence. For example, an ICP variant can result from one or more (such as, for example, about 1 to about 25, about 1 to about 20, about 1 to about 15, about 1 to about 10, or about 1 to about 5) changes to an amino acid sequence of a native ICP.

Also by way of example, a variant of an anti-ICP antibody can result from one or more (such as, for example, about 1 to about 25, about 1 to about 20, about 1 to about 15, about 1 to about 10, or about 1 to about 5) changes to an amino acid sequence of a native or previously unmodified anti-ICP antibody. Variants can be naturally occurring, such as allelic or splice variants, or can be artificially constructed. Polypeptide variants can be prepared from the corresponding nucleic acid molecules encoding the variants.

As used herein, the term "derivative" refers to a polypeptide that comprises an amino acid sequence of a reference polypeptide that has been altered by the introduction of amino acid residue substitutions, deletions or additions. The reference polypeptide can be an ICP or an anti-glycosylated ICP antibody. The term "derivative" as used herein also refers to an ICP or an anti-glycosylated ICP antibody that has been chemically modified, e.g., by the covalent attachment of any type of molecule to the polypeptide. For example, an ICP or an anti-glycosylated ICP antibody can be chemically modified, e.g., by glycosylation, acetylation, pegylation, phosphorylation, amidation, derivatization by known protecting/blocking groups, proteolytic cleavage, linkage to a cellular ligand, linkage to a peptide or protein tag molecule, or other protein, etc. The derivatives are modified in a manner that is different from the naturally occurring or starting peptide or polypeptides, either in the type or location of the molecules attached. Derivatives may further include deletion of one or more chemical groups which are naturally present on the peptide or polypeptide. A derivative of an ICP or an anti-glycosylated ICP antibody may be chemically modified by chemical modifications using techniques known to those of skill in the art, including, but not limited to, specific chemical cleavage, acetylation, formulation, metabolic synthesis of tunicamycin, etc. Further, a derivative of an ICP or an anti-glycosylated ICP antibody can contain one or more non-classical amino acids. A polypeptide derivative possesses a similar or identical function as the reference polypeptide, which can be an ICP or an anti-glycosylated ICP antibody described herein.

As used herein, the term "composition" refers to a product containing specified component ingredients (e.g., a polypeptide or an antibody provided herein) in, optionally, specified or effective amounts, as well as any desired product which results, directly or indirectly, from the combination or interaction of the specific component ingredients in, optionally, the specified or effective amounts.

As used herein, the term "treat," "treatment," or "treating" refers to administration or application of a therapeutic agent to a subject in need thereof, or performance of a procedure or modality on a subject, for the purpose of obtaining at least one positive therapeutic effect or benefit, such as treating a disease or health-related condition. For example, a treatment can include administration of a pharmaceutically effective amount of an antibody, or a composition or formulation thereof, that specifically binds to glycosylated ICP for the purpose of treating various types of cancer. The terms "treatment regimen," "dosing regimen," or "dosing protocol," are used interchangeably and refer to the timing and dose of a therapeutic agent, such as an anti-glycosylated ICP antibody produced by the methods described herein. As used herein, the term "subject" refers to either a human or a non-human animal, such as primates, mammals, and vertebrates having a cancer or diagnosed with a cancer. In preferred embodiments, the subject is a human. In some embodiments, the subject is a cancer patient. In an embodiment, the subject in need will or is predicted to benefit from anti-glycosylated ICP antibody, e.g., anti-glycPD-L1 antibody, treatment.

As used herein, the term "therapeutic benefit" or "therapeutically effective" refers the promotion or enhancement of the well-being of a subject in need (e.g., a subject with a cancer or diagnosed with a cancer) with respect to the medical treatment, therapy, dosage administration, of a condition, particularly as a result of the use of the anti-glycosylated ICP antibodies and the performance of the methods using these antibodies. This includes, but is not limited to, a reduction in the frequency or severity of the signs or symptoms of a disease. For example, treatment of a cancer may involve, for example, a reduction in the size of a tumor, a reduction in the invasiveness or severity of a tumor, a reduction infiltration of cancer cells into a peripheral tissue or organ; a reduction in the growth rate of the tumor or cancer, or the prevention or reduction of metastasis. Treatment of cancer may also refer to achieving a sustained response in a subject or prolonging the survival of a subject with cancer.

Methods of Producing Antibodies that Preferentially Bind Glycosylated Immune Checkpoint Proteins For antibody production, recipient animals are inoculated with an antigen, such as a glycosylated ICP or peptide to generate an immune response and produce antibodies specific for the glycosylated ICP or peptide, e.g., PD-L1. Frequently, an antigen is bound or conjugated to another molecule to enhance the immune response. As used herein, a conjugate is any peptide, polypeptide, protein, or non-proteinaceous substance bound to an antigen that is used to elicit an immune response in an animal. Antibodies produced in an animal in response to antigen inoculation comprise a variety of non-identical molecules (polyclonal antibodies) made from a variety of individual antibody producing B lymphocytes. A polyclonal antibody is a mixed population of antibody species, each of which may recognize a different epitope on the same antigen. Given the correct conditions for polyclonal antibody production in an animal, most of the antibodies in the animal's serum will recognize the collective epitopes on the antigenic compound to which the animal has been immunized. This specificity is further enhanced by affinity purification to select only those antibodies that recognize the antigen or epitope of interest.

The methods for generating monoclonal antibodies (MAbs) generally begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and may provide certain advantages. Mice (e.g., BALB/c mice) are routinely used and generally give a high percentage of stable fusions. Hybridoma technology as used in monoclonal antibody production involves the fusion of a single, antibody-producing B lymphocyte isolated from a mouse previously immunized with a glycosylated ICP antigen with an immortalized myeloma cell, e.g., a mouse myeloma cell line. This technology provides a method to propagate a single antibody-producing cell for an indefinite number of generations, such that unlimited quantities of structurally identical antibodies having the same antigen or epitope specificity, i.e., monoclonal antibodies, may be produced. Populations of hybridomas or other cells expressing the population of monoclonal antibodies derived from the immunized animal may be screened for anti-glycosylated ICP antibodies as described herein.

In a particular embodiment, a glycosylated ICP, or a glycosylated peptide portion thereof, as described herein, for example, glycosylated PD-L1 or a peptide thereof, is administered to a recipient animal, e.g., a mouse or rat, via an injection route according to a dosing scheme. Typically, an initial immunization is given; the animal is allowed to rest for a period of time, e.g., without limitation, 7-15 days; and booster immunizations are given for a determined time period, such as 2-3 weeks, or even months. During the period of booster immunizations, the animals may be tested for antibody titer in plasma or serum by methods conventionally used in the art. To this end, blood samples are obtained from animals for measurement of serum antibodies after several weeks of immunization. Several humane techniques have been developed for collection of small volumes of blood from mice, as set forth in *Clinical Chemistry of Laboratory Animals*, Eds. W. F. Loeb and F. W. Quimby, Taylor & Francis, 1999. Serum antibody titer is determined with various techniques, such as enzyme-linked immunosorbent assay (ELISA) and flow cytometry. If the antibody titer is high, cell fusion can be performed. If the titer is too low, mice can be boosted until an adequate response is achieved, as determined by repeated blood sampling. When the antibody titer is high enough, mice are commonly boosted by injecting antigen without adjuvant intraperitoneally or intravenously (via the tail veins), e.g., 3 days before fusion but 2 weeks after the previous immunization.

When the antibody titer is sufficient as determined by the practitioner in the art, a mouse is euthanized and its spleen is removed. Spleen cells are dispersed into a single cell suspension and are mixed with an immortalized myeloma cell line (e.g., without limitation, Sp/02) under conditions appropriate for cell fusion and the production of hybridomas in vitro. Fusing antibody-producing spleen cells, which have a limited life span, with cells derived from immortalized myeloma cells results in a hybridoma that is capable of unlimited growth. Myeloma cells are immortalized cells that are cultured with 8-azaguanine to ensure their sensitivity to the hypoxanthine-aminopterin-thymidine (HAT) selection medium used after cell fusion. About a week before cell fusion, myeloma cells are grown in 8-azaguanine; cells must have high viability and rapid growth. The HAT selection medium allows only fused cells to survive in culture. In the HAT selection technique, the selection growth medium contains the inhibitor aminopterin, which blocks synthetic pathways by which nucleotides are made. Therefore, cells must use a bypass pathway to synthesize nucleic acids—this pathway is defective in the myeloma cell line to which the normal antibody-producing cells are fused. Because neither the myeloma nor the antibody-producing cell can grow on its own, only the hybrid cells "hybridomas" undergo cell division and persist and proliferate in culture. (*Monoclonal Antibody Production,* 1999, Inst. For Laboratory Animal Research and National Research Council, National Academy Press).

Cell fusion is performed by co-centrifuging the freshly harvested spleen cells and myeloma cells in polyethylene glycol, a cell membrane fusion potentiator. The cells are then distributed into multi-well plates with or without feeder cells, which can be derived from saline peritoneal washes of mice. Feeder cells are believed to supply growth factors that promote growth of the hybridoma cells; however, commercial preparations resulting from the collection of media supporting the growth of cultured cells and containing growth factors can be used in lieu of mouse-derived feeder cells. Murine bone marrow-derived macrophages can also be used as feeder cells. Small clusters of hybridoma cells from the multi-well plates can be grown in tissue culture, followed by selection for antigen binding by methods described herein. Hybridomas can also be grown in mouse ascites, with cloning at a later time. Limiting dilution 'cloning' of hybridoma cells ensures that a majority of wells each contain at most a single clone. One skilled in the art can select hybridomas capable of expansion and further growth. Hybridomas are screened for the production of monoclonal antibodies having suitable binding specificity.

While screening for monoclonal antibodies may be accomplished through various procedures known in the art, e.g., in bacterial systems where antibodies are presented on the surface of bacteriophages ("phage display" procedures), other screening techniques are also envisioned. Human antibodies may be identified and isolated from human combinatorial antibody libraries. For example, bacteriophage antibody expression technology allows specific antibodies to be produced in the absence of animal immunization, as described in U.S. Pat. No. 6,946,546, which is incorporated herein by reference. These techniques are further described in Marks et al., 1992, Bio/Technol., 10:779-783; Stemmer, 1994, Nature, 370:389-391; Gram et al., 1992, Proc. Natl. Acad. Sci. USA, 89:3576-3580; Barbas et al., 1994, Proc. Natl. Acad. Sci. USA, 91:3809-3813; and Schier et al., 1996, Gene, 169(2):147-155.

For example, a hybridoma library technique may be employed in which a hybridoma cell line that produces a monoclonal antibody that specifically and preferentially binds to glycosylated ICP or a peptide thereof is selected and identified. Hybridoma libraries can be interrogated for antibody binding activity prior to cloning. Such a process includes cloning of single-cells by flow cytometry which enables the analysis of true clones and does not require multiple rounds of sub-cloning (See, e.g., Antibody Solutions, Sunnyvale, CA). FACS sorting can be used repeatedly to select those hybridoma cell variants that display an especially large number of anti-glycosylated ICP antibodies on their surface. Hybridoma libraries may have an inducible system that is highly sensitive and specific, which can be utilized in conjunction with in vivo affinity maturation in multiple species; negative selection for self-antigen binding; natural pairing of heavy and light chains; direct antibody secretion by the hybridoma; no cloning for expression; and mammalian post-translational modification of antibody. (Antibody Solutions, Sunnyvale, CA). Once a hybridoma that produces a desired anti-glycosylated ICP antibody is screened and identified using the methods described herein, a clone can be expanded and antibody isolated for further use.

Monoclonal antibodies produced by hybridoma technology or other populations of antibody expressing cells, such as phage display library, may be selected for binding specificity using protocols and techniques known for the selection and identification of antibodies that specifically bind a particular antigen. As known to those having skill in the art, a variety of direct, indirect and competitive binding assays may be used to assay for antibodies that specifically bind a target antigen. Illustratively, and without limitation, a glycosylated ICP antigen may be attached to a solid substrate and an appropriate detectably-labeled reporter molecule, e.g., a labeled secondary antibody, may be used to determine specific binding of the anti-glycICP antibody which has bound to the glycosylated ICP antigen on the solid substrate. In addition, when libraries of antibodies are screened where the antibody is displayed on the cell surface, for example a phage display library, the library may be "panned" for antibodies that bind the glycosylated ICP antigen. The antigen or ligand for which the antibody is to be selected may be labeled with a detectable or selectable label, the population of antibody expressing cells may be contacted with the detectable or selectable label and then the cells expressing antibody that binds to the labeled antigen are selected. For example, if the label is biotin, the cells expressing antibody which is bound to the biotin labeled antigen can isolated using binding of the biotin to streptavidin which may be on a solid support, beads, etc.

In particular embodiments, the population antibodies to be screened can be assayed for antibodies that preferentially bind to the glycosylated form of the ICP over the unglycosylated form of the ICP. For example, cells that express, preferentially recombinantly express, glycosylated ICP are labeled, for example, with biotin, and mixed with cells that express an unglycosylated form of the ICP, but are not labeled or have a different label. For example, the glycosylation site or sites on the ICP may be mutated (for example, substituting a glutamine for an asparagine in the glycosylation consensus site) so that the ICP is not glycosylated. The cell mixture is incubated with the antibody to be tested as well as a molecule that binds to the labeled cells (those expressing the glycosylated form) but not the unlabeled cells. For example, if the label is biotin, the cell mixture is incubated with the antibody to be tested and to a labeled streptavidin. The cells are then incubated with a labeled secondary antibody to detect any antibody bound to the cells. Any method known in the art can be used to compare the binding of the antibody to the cells expressing the glycosylated ICP and the cells expressing the unglycosylated ICP. For example, the cells expressing the glycosylated ICP and the cells expressing the unglycosylated ICP can be separated and the level of secondary antibody binding can be measured by FACS/flow cytometry analysis to assess the relative binding of the antibody to the glycosylated ICP and the unglycosylated ICP. An exemplary method is described in Example 2, antibodies having 2-fold, 3-fold, 4-fold, 5-fold, 6-fold, 7-fold, 8-fold, 9-fold or 10-fold greater binding to the glycosylated ICP as compared to the unglycosylated ICP may be selected as preferentially binding glycosylated ICP.

If antibodies that specifically bind to glycosylated ICP are first identified, those antibodies can be further screened and analyzed by any other method known in the art for comparing binding to the unglycosylated form. For example, the antibodies may be in any binding assay, such as ELISA, radioimmunoassays, BIACORE, etc. for antigen binding. In a particular embodiment, the glycosylated ICP and unglycosylated ICP are coated on a solid surface (e.g., the well of an assay plate). The unglycosylated ICP may be generated by treatment of glycosylated ICP with an enzyme to remove the glycosylation, e.g., PNGase which removes N-linked glycosylation, or by recombinantly expressing an ICP with mutant glycosylation sites so that it is not glycosylated by the expressing cells. Antibodies are then assayed for binding the glycosylated and unglycosylated forms at varying concentrations of antibodies to detect a difference in binding affinity for the glycosylated ICP as compared to the unglycosylated ICP.

In addition, preferential binding can also be tested by Western Blot or FACS flow cytometry analysis. As well known by one skilled in the art, Western blot is a laboratory research technique used to separate and identify proteins that contains epitopes which are specifically bound by an antibody. In general, the technique involves separating protein antigens (often in a cell lysate) by size/molecular weight via gel electrophoresis. The proteins separated on the gel are transferred to a solid membrane support, such as nylon, polyvinylidene fluoride (PVDF), or nitrocellulose, and an antibody, which is detectably labeled, is incubated under conditions in which the antibody can bind to the protein on the solid support that contains epitopes specifically recognized by the antibody. Bound protein can then be visualized and quantified. It is also possible to use a labeled secondary antibody that binds to the first antigen-specific antibody, for binding detection. See, by way of nonlimiting example, Mahmood and Yang, 2012, NAM J Med Sci, 4(9):429-434. Also, as known to the skilled practitioner in the art, flow cytometry is performed using automated flow cytometer instruments (FC or FCM) to quantify rapidly multiple characteristics and properties of single cells, one cell at a time as the cells flow past a laser beam. FC can measure cell size, cell granularity, amounts of specific surface receptor proteins, amounts of intracellular proteins, the amounts of cell components such as total DNA, newly synthesized DNA, gene expression as the amount messenger RNA for a particular gene, or transient signaling events in living cells. Quantities are usually relative, but can be numbers of molecules per cell when absolute values are needed. Typically, from three to six properties or components may be quantified in a single sample, cell by cell, for about $1 \times 10^4$-$1 \times 10^5$ cells in less than one minute. (Brown, M. and Wittwer, C., 2000, Clin. Chem., 46(8):1221-1229; and Martz, E., 2003, Microbiology 542, U. Massachusetts, Amherst, MA).

In addition, the antibodies may be assayed for the ability to specifically block the interaction between the glycosylated target ligand to which the antibody is directed, e.g., glycosylated PD-L1, and its cognate (ICP) binding molecule, e.g., PD-1. For example, glycosylated ICP may be either expressed on the surface of cells or adhered to a solid support and then incubated with the antibody to be tested and the cognate ICP binding partner with a detectable label. The level of binding of the labeled ICP binding partner to the ICP can then be quantified compared to a control in the absence of antibody to be tested. A reduction in binding of the ICP binding partner indicates that the antibody can inhibit or block the interaction of the ICP and the ICP binding partner. Absence of binding of the ICP binding molecule indicates that the antibody has blocked the binding of ICP to the ICP binding partner. Exemplary methods are described in Examples 2 and 5.

Forms of Antibodies Suitable for Use as ICP Inhibitors

Once the antibodies that preferentially and specifically bind the glycosylated ICP are identified and isolated, they may be further engineered, for example, to make them more appropriate as therapeutics. In the case of non-human monoclonal antibodies, the antibodies should be made "chimeric" or "humanized". Methods have been developed to replace light and heavy chain constant domains of the monoclonal antibody with analogous domains of human origin, leaving the variable regions of the foreign antibody intact. Methods have also been developed to convert variable domains of monoclonal antibodies to more human form by recombinantly constructing antibody variable domains having both rodent and human amino acid sequences. In "humanized" monoclonal antibodies, only the hypervariable CDRs are derived from non-human (e.g., mouse, rat, chicken, llama, etc.) monoclonal antibodies, and the framework regions are derived from human antibody amino acid sequences. The replacement of amino acid sequences in the antibody that are characteristic of rodents with amino acid sequences found in the corresponding positions of human antibodies reduces the likelihood of adverse immune reaction to foreign protein during therapeutic use in humans. A hybridoma or other cell producing an antibody may also be subject to genetic mutation or other changes, which may or may not alter the binding specificity of antibodies produced by the hybridoma.

Engineered antibodies may be created using monoclonal and other antibodies and recombinant DNA technology to produce other antibodies or chimeric molecules that retain the antigen or epitope binding specificity of the original antibody, i.e., the molecule has a specific binding domain. Such techniques may involve introducing DNA encoding the immunoglobulin variable region or the CDRs of an antibody into the genetic material for the framework regions, constant regions, or constant regions plus framework regions, of a different antibody. See, for instance, U.S. Pat. Nos. 5,091,513 and 6,881,557, which are incorporated herein by reference.

By known means as described herein, polyclonal or monoclonal antibodies, antibody fragments having binding activity, binding domains and CDRs (including engineered forms of any one of the foregoing), may be created that specifically bind to glycosylated ICP, one or more of its respective epitopes, or conjugates of any one of the foregoing, whether such antigens or epitopes are isolated from natural sources or are synthetic derivatives or variants of the natural compounds.

Certain animal species may be less preferable for generating therapeutic antibodies because they may be more likely to cause an immune or allergic response due to activation of the complement system through the "Fc" portion of the antibody. However, whole antibodies may be enzymatically digested into the "Fc" (complement binding) fragment, and into peptide fragments having the binding domains or CDRs. Removal of the Fc portion reduces the likelihood that this antibody fragment will elicit an undesirable immunological response and, thus, antibodies without an Fc portion may be preferential for prophylactic or therapeutic treatments. As described above, antibodies may also be constructed so as to be chimeric, humanized, or partially or fully human, so as to reduce or eliminate potential adverse immunological effects resulting from administering to an animal an antibody that has been produced in, or has amino acid sequences from, another species.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are as described in Table 1, supra. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Antibody proteins may be recombinant, or synthesized in vitro. Alternatively, a non-recombinant or recombinant antibody protein may be isolated from bacteria. It is also contemplated that bacteria containing an antibody protein variant may be implemented in compositions and methods herein to isolate antibodies with improved binding or other parameters. It is contemplated that in compositions described herein there is between about 0.001 mg and about 10 mg of total antibody polypeptide per ml. Thus, the concentration of antibody protein in a composition can be about, at least about or at most about or equal to 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, at most about, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% may be an antibody that binds glycosylated ICP.

An antibody or an immunological portion of an antibody that retains binding activity to an ICP, can be chemically conjugated to, or recombinantly expressed as, a fusion protein with other proteins. All such fused proteins are included in the definition of antibodies or an immunological portion of an antibody. In some embodiments, antibodies and antibody-like molecules generated against glycosylated immune checkpoint polypeptides or peptides thereof that are linked to at least one agent to form an antibody conjugate or payload are encompassed. In order to increase the efficacy of antibody molecules as diagnostic or therapeutic agents, it is conventional to link or covalently bind or complex at least one desired molecule or moiety to the antibody. Such a linked molecule or moiety may be, but is not limited to, at least one effector or reporter molecule. Effector molecules comprise molecules having a desired activity, e.g., cytotoxic activity. Non-limiting examples of effector molecules that may be attached to antibodies include toxins, therapeutic enzymes, antibiotics, radio-labeled nucleotides and the like. By contrast, a reporter molecule is defined as any moiety that may be detected using an assay. Non-limiting examples of reporter molecules that may be conjugated to antibodies include enzymes, radiolabel s, haptens, fluorescent labels, phosphorescent molecules, chemiluminescent molecules, chromophores, luminescent molecules, photoaffinity molecules, colored particles or ligands, such as biotin, and the like. Several methods are known in the art for attaching or conjugating an antibody to a conjugate molecule or moiety. Some attachment methods involve the use of a metal chelate complex, employing by way of nonlimiting example, an organic chelating agent such a diethylenetriaminepentaacetic acid anhydride (DTPA); ethylenetriaminetetraacetic acid; N-chloro-p-toluenesulfonamide; and/or tetrachloro-3-6α-diphenylglycouril-3 attached to the antibody. Antibodies may also be reacted with an enzyme in the presence of a coupling agent such as glutaraldehyde or periodate. Conjugates with fluorescein markers are conventionally prepared in the presence of these coupling agents or by reaction with an isothiocyanate. In another embodiment, an anti-glycosylated ICP antibody may be coupled or linked to a compound or substance, such as polyethylene glycol (PEG), to increase its in vivo half-life in plasma, serum, or blood following administration.

In an embodiment, the antibody is a chimeric antibody, for example, an antibody comprising antigen binding sequences (e.g., V domains and/or CDRs) from a non-human donor grafted to a heterologous non-human, human or humanized sequence (e.g., framework and/or constant domain sequences). In one embodiment, the non-human donor sequences are from mouse or rat. In one embodiment, an antigen binding sequence is synthetic, e.g., obtained by mutagenesis (e.g., phage display screening of a human phage library, etc.). In one embodiment, a chimeric antibody has murine V regions and human C regions. In one embodiment, the murine light chain V region is fused to a human kappa light chain C region. In one embodiment, the murine heavy chain V region is fused to a human IgG1 C region.

In an embodiment, the antibody is an immunoglobulin single variable domain derived from a camelid antibody, preferably from a heavy chain camelid antibody, devoid of light chains, which are known as $V_HH$ domain sequences or Nanobodies™. A Nanobody™ (Nb) is the smallest functional fragment or single variable domain ($V_HH$) of a naturally occurring single-chain antibody and is known to the person skilled in the art. They are derived from heavy chain only antibodies seen in camelids (Hamers-Casterman et al., 1993, *Nature*, 363:446-448; and Desmyter et al., 1996, *Nat. Struct. Biol.*, pp. 803-811). In the family of "camelids," immunoglobulins devoid of light polypeptide chains are found. "Camelids" comprise old world camelids (*Camelus bactrianus* and *Camelus dromedarius*) and new world camelids (for example, *Lama paccos, Lama glama, Lama guanicoe* and *Lama vicugna*). The single variable domain heavy chain antibody is herein designated as a Nanobody™ or a $V_HH$ antibody. The small size and unique biophysical properties of Nbs excel conventional antibody fragments for the recognition of uncommon or hidden epitopes and for binding into cavities or active sites of protein targets. Further, Nbs can be designed as multi-specific and multivalent antibodies, attached to reporter molecules, or humanized. Nbs are stable, survive the gastro-intestinal system and can easily be manufactured.

In another embodiment, the antibody is a bispecific antibody. Unifying two antigen binding sites of different specificity into a single construct, bispecific antibodies have the ability to bring together two discreet antigens with exquisite specificity and therefore have great potential as therapeutic agents. Bispecific antibodies were originally made by fusing two hybridomas, each capable of producing a different immunoglobulin. Bispecific antibodies are also produced by joining two scFv antibody fragments while omitting the Fc portion present in full immunoglobulins. Each scFv unit in such constructs can contain one variable domain from each of the heavy ($V_H$) and light ($V_L$) antibody chains, joined with one another via a synthetic polypeptide linker, the latter often being genetically engineered so as to be minimally immunogenic while remaining maximally resistant to proteolysis. Respective scFv units may be joined by a number of known techniques, including incorporation of a short (usually less than 10 amino acids) polypeptide spacer bridging the two scFv units, thereby creating a bispecific single chain antibody. The resulting bispecific single chain antibody is therefore a species containing two $V_H/V_L$ pairs of different specificity on a single polypeptide chain, in which the $V_H$ and $V_L$ domains in a respective scFv unit are separated by a polypeptide linker long enough to allow intramolecular association between these two domains, such that the so-formed scFv units are contiguously tethered to one another through a polypeptide spacer kept short enough to prevent unwanted association between, for example, the $V_H$ domain of one scFv unit and the $V_L$ of the other scFv unit.

In another embodiment, the antibody is a biparatopic antibody. As used herein the term "biparatopic antibody" refers to a bispecific binding molecule that comprises two antigen binding domains which recognize and bind to two different non-overlapping epitopes, antigenic determinants, or domains on the same protein target, e.g., a tumor-associated ICP target antigen, or a glycosylated ICP target antigen as described herein. In an embodiment, a biparatopic antibody directed against a glycICP or one or more peptide portions thereof, as described herein, comprises a first immunoglobulin variable domain and a second immunoglobulin variable domain, wherein the two binding domains bind to two different non-overlapping epitopes of the same target glycICP protein. One or both of the epitopes recognized by the first and second immunoglobulin binding domains may be glycosylated or contain glycosylated residues. Preferably, at least one of the immunoglobulins preferentially binds the glycosylated form of the glycICP protein relative to the unglycosylated form.

In another embodiment, a biparatopic antibody comprises an immunoglobulin (preferably a tetravalent IgG) that binds to an epitope on a glycICP target molecule and a scFv that binds to a different and non-overlapping epitope on the same glycICP target molecule, in which the immunoglobulin and the scFv are linked by a linker so as to permit the binding of the immunoglobulin and the scFv to the different and non-overlapping epitopes on the glycICP target molecule. Accordingly, biparatopic antibodies are created from two anti-glycICP antibodies identified by the methods described herein that bind to different epitopes (or domains) on the same glycICP target (i.e., bi-paratopic binding) to enhance binding affinity/avidity; to increase antibody load on tumor cells for enhanced effector functions, such as antibody dependent cellular cytotoxicity (ADCC) and/or complement dependent cytotoxicity (CDC); and/or to improve or increase tumor retention time. In addition, bivalent biparatopic antibodies that target two non-overlapping epitopes on a tumor-associated glycICP antigen have the potential to induce clustering of glycICP target molecules in the cell membrane, which, in turn, may promote increased internalization, lysosomal trafficking and degradation. Biparatopic antibodies directed against two different, non-overlapping epitopes on a target protein/antigen may be generated using techniques known in the art. See, e.g., B. Roberts et al., 1999, *Int. J. Cancer*, Vol. 81:285-291 (carcinoembryonic antigen, CEA); D. Lu et al., 1999, *J. Immunol. Methods*, Vol. 230:159-71 (vascular endothelial growth factor receptor 2, VEGF2); WO 2009/068627, Ablynx NV, published Jun. 4, 2009; WO 2010/142534, and Ablynx NV, published Dec. 16, 2010.

In an embodiment, a bivalent biparatopic antibody may be produced by using variable domain sequences from two different anti-glycICP antibodies, identified as described herein, that recognize and bind to different non-overlapping epitopes on a given glycICP target protein, wherein the antibody contains the single-chain variable fragment (scFv) of one of the anti-glycICP antibodies attached to the N-terminus of the H chain and/or the L chain, or, alternatively, the C-terminus of the $C_H3$ domain, of the second anti-ICP antibody that recognizes a different and non-overlapping epitope on the glycICP. The scFv may be linked to the second anti-ICP antibody via a peptide linker, for example, such as those used to link binding domains in an scFv. See, e.g., Dimasi et al., *J. Mol. Biol.*, 393:672-692 (2009). The resulting binding molecule product, or biparatopic antibody, contains four anti-glycICP binding units, or two binding units on each arm of the molecule, that are able to interact with and bind to two different epitopes on the glycICP. According to this embodiment, a bivalent biparatopic antibody that targets two non-overlapping epitopes on a glycICP expressed on the surface of a tumor cell could effectively crosslink the glycICPs through epitope binding to induce clustering of glycICPs on the cell surface, leading to the formation of large complexes that elicit and promote enhanced internalization and lysosomal degradation. In an embodiment, the biparatopic antibody is linked to a toxin or anti-cancer drug to produce an antibody-drug conjugate (ADC) as described further herein. The enhanced internalization and endocytosis of such anti-ICP biparatopic antibodies and lysosomal trafficking ultimately results in the delivery of greater amounts of toxin into the target cells and greater tumor cell killing or regression. Such effects were observed both in vitro and in vivo as described for a biparatopic anti-HER2 ADC (J. Y. Li et al., 2016, *Cancer Cell*, Vol. 29:117-129). Illustratively, biparatopic anti-glycICP antibodies or anti-glycICP ADCs may be produced that specifically bind to two non-overlapping epitopes of one the following glycosylated ICPs: PD-L1, PD-L2, PD-1, TIM-3, LAG-3, BTLA, CEACAM1, BTN1A1, BTNL2, SEMA4D, CD47, CD96, B7-H3, B7-H4, CTLA-4, VISTA, or KIR and the like as described herein, to prevent or block their interaction with their cognate binding partner and to promote their internalization and degradation, as well as killing of the tumor cells if an anti-glycICP ADC is used.

In other embodiments, anti-glycICP binding molecules or antibodies encompassed by the invention may be multi-paratopic, i.e., contain antigen binding domains which recognize and bind three, four, or more different, preferably non-overlapping, epitopes or antigenic determinants on the same glycICP target molecule. In yet other embodiments, the anti-glycICP antibodies are both bi- or multiparatopic and multivalent, i.e., also comprise antigen binding sites or "paratopes" that recognize and bind to one or more different epitopes or antigenic determinants on different target glycICP molecules.

Examples of antibody fragments include, without limitation: (i) the Fab fragment, consisting of $V_L$, $V_H$, $C_L$, and $C_{H1}$ domains; (ii) the "Fd" fragment consisting of the $V_H$ and $C_{H1}$ domains; (iii) the "Fv" fragment consisting of the $V_L$ and $V_H$ domains of a single antibody; (iv) the "dAb" fragment, which consists of a $V_H$ domain; (v) isolated CDR regions; (vi) F(ab')2 fragments, a bivalent fragment comprising two linked Fab fragments; (vii) single chain Fv molecules ("scFv"), in which a $V_H$ domain and a $V_L$ domain are linked by a peptide linker that allows the two domains to associate to form a binding domain; (viii) bi-specific single chain Fv dimers (see U.S. Pat. No. 5,091,513); and (ix) diabodies, multivalent, or multispecific fragments constructed by gene fusion (U.S. Patent Appln. Pub. No. 20050214860). Fv, scFv, or diabody molecules may be stabilized by the incorporation of disulfide bridges linking the $V_H$ and $V_L$ domains. Minibodies comprising a scFv joined to a $C_{H3}$ domain (Hu et al., 1996, *Cancer Res.*, 56:3055-3061) may also be useful. In addition, antibody-like binding peptidomimetics are also contemplated in embodiments. "Antibody like binding peptidomimetics" (ABiPs), which are peptides that act as pared-down antibodies and have certain advantages of longer serum half-life as well as less cumbersome synthesis methods, have been reported by Liu et al., 2003, *Cell Mol. Biol.*, 49:209-216).

Anti-Glycosylated PD-L1 Antibodies (Anti-glycPD-L1 Antibodies)

In a particular embodiment, methods of isolating and identifying antibodies that specifically bind to the glycosylated ICP protein, PD-L1 (e.g., a PD-L1 protein having a specific N-glycan structure; specific glycopeptides of PD-L1) or glycosylated PD-L1 peptides relative to non-glycosylated PD-L1 and inhibit the immune suppressive function of the glycosylated PD-L1/PD-1 interaction (anti-glycPD-L1 antibodies) are provided. Such an anti-glycPD-L1 antibody is useful in the treatment of disease, particularly cancer. The anti-glycPD-L1 antibodies may of the IgG, IgM, IgA, IgD, and IgE Ig classes, as well as polypeptides comprising antibody CDR domains that retain antigen binding activity. Illustratively, the anti-glycPD-L1 antibodies may be chimeric, affinity matured, humanized, or human antibodies. In a preferred embodiment, the anti-glycPD-L1 antibodies are monoclonal antibodies. In another preferred embodiment, the monoclonal anti-glycPD-L1 antibodies are humanized or human antibodies. By known means and as described herein, polyclonal or monoclonal antibodies, antibody fragments, binding domains and CDRs (including engineered forms of any one of the foregoing) may be created that are specific for glycosylated PD-L1 antigen, one or more of its respective epitopes, or conjugates of any one of the foregoing, whether such antigens or epitopes are isolated from natural sources or are synthetic derivatives or variants of the natural compounds. The antibodies may be bispecific or biparatopic.

Disease Treatment by Specific Anti-glycICP Antibodies Obtained by the Methods

In certain aspects, an antibody obtained by the described methods, or an antigen binding fragment thereof, (e.g., an antibody that specifically binds to a glycosylated ICP, such as PD-L1) may be used in treatment methods and administered to treat a cancer. Accordingly, provided herein are methods of treating a cancer by administering to a subject in need a therapeutically effective amount of at least one anti-glycosylated ICP antibody, or a binding fragment thereof, e.g., an anti-glycPD-L1 antibody, to treat the cancer. As noted herein, treatment or therapeutic treatment involves reducing, preventing, inhibiting, or blocking the growth, proliferation, migration, etc. of cancer cells. The methods provide a benefit to the subject, e.g., a human patient, undergoing treatment, with particular regard to a subject's tumor cells that express ICP cell surface proteins that can bind/interact with an ICP cognate ligand expressed on the cell surface of immune effector cells, such as T-cells, particularly, killer or cytotoxic T-cells. Treatment of these subjects with an effective amount of at least one of the anti-glycosylated ICP antibodies is expected to result in binding of the antibody(ies) to glycosylated ICP on the tumor cells and in preventing, blocking, or inhibiting the interaction of ICP-expressing tumor cells with T cells expressing cognate ICP ligand, thereby preventing or avoiding immunosuppression of T-cell activity and allowing T cells to be activated to kill tumor cells that express the ICP, such as PD-L1. Accordingly, the methods of using the anti-glycosylated ICP antibodies produced and obtained by the described methods are advantageous for a subject who is in need of, capable of benefiting from, or who is desirous of receiving the benefit of, the anti-cancer results achieved by the practice of the present methods. A subject's seeking the therapeutic benefits of the methods involving administration of at least one anti-glycosylated ICP antibody, or a binding fragment thereof, e.g., an anti-glycPD-L1 antibody or a binding fragment thereof, in a therapeutically effective amount, or receiving such therapeutic benefits offer advantages to the art. In addition, the present methods offer the further advantages of eliminating or avoiding side effects, adverse outcomes, contraindications, and the like, or reducing the risk or potential for such issues to occur compared with other treatments and treatment modalities.

Cancers for which the present treatment methods are useful include any malignant cell type, such as those found in a solid tumor or a hematological tumor, particularly tumors with cells that express glycosylated ICP, such as glycosylated PD-L1 on their surface. In general, a tumor refers to a malignant or a potentially malignant neoplasm or tissue mass of any size, and includes primary tumors and secondary tumors. A solid tumor is an abnormal tissue mass or growth that usually does not contain cysts or liquid. Exemplary solid tumors can include, but are not limited to, a tumor of an organ selected from the group consisting of pancreas, gall bladder, colon, cecum, stomach, brain, head, neck, ovary, testes, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer and gastrointestinal stromal cancer), pancreatic cancer, glioblastoma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, melanoma, superficial spreading melanoma, lentigo malignant melanoma, acral lentiginous melanomas, nodular melanomas, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's macroglobulinemia), chronic lymphocytic leukemia (CLL), acute lymphoblastic leukemia (ALL), Hairy cell leukemia, multiple myeloma, acute myeloid leukemia (AML) and chronic myeloblastic leukemia.

The cancer may specifically be of the following histological types, though it need not be limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous hi stiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The cancer to be treated with an anti-glycICP antibody obtained by the described methods, is preferably positive for an ICP expressed on tumor or cancer cells, for example, PD-L1, particularly glycosylated PD-L1. Specifically, the cancer to be treated is positive for the ICP which the anti-glycICP antibody binds. In certain embodiments, the tumor cells are also positive for a tumor cell marker such as EGFR or HER2/neu expression, e.g., as expressed on breast cancer cells. The presence or absence of these markers may indicate that combination therapy with a targeted therapeutic, such as a tyrosine kinase inhibitor, e.g., gefitinib for an EGFR-positive cancer, or Herceptin for a HER2/neu-positive cancer, in combination with the anti-glycICP antibodies, would provide a treatment benefit for a subject in need. In certain embodiments, the cancer is a BLBC.

Other markers that may be used to characterize cancers to guide choice of therapy or monitor therapy with the anti-glycICP antibodies include ALK gene rearrangements and overexpression in non-small cell lung cancer and anaplastic large cell lymphoma; alpha-fetoprotein (AFP) for liver cancer and germ cell tumors; beta-2-microglobulin (B2M) for multiple myeloma, chronic lymphocytic leukemia, and some lymphomas; beta-human chorionic gonadotropin (Beta-hCG) for choriocarcinoma and germ cell tumors; BRCA1 and BRCA2 gene mutations for ovarian cancer and breast cancer; BCR-ABL fusion gene (Philadelphia chromosome) for chronic myeloid leukemia, acute lymphoblastic leukemia, and acute myelogenous leukemia; BRAF V600 mutations for cutaneous melanoma and colorectal cancer; C-kit/CD117 for gastrointestinal stromal tumor and mucosal melanoma; CA15-3/CA27.29 for breast cancer; CA19-9 for pancreatic cancer, gallbladder cancer, bile duct cancer, and gastric cancer; CA-125 for ovarian cancer; calcitonin for medullary thyroid cancer; carcinoembryonic antigen (CEA) for colorectal cancer and some other cancers; CD20 for non-Hodgkin lymphoma; Chromogranin A (CgA) for neuroendocrine tumors; chromosomes 3, 7, 17, and 9p21 for bladder cancer; cytokeratin fragment 21-1 for lung cancer; EGFR gene mutation analysis for non-small cell lung cancer; estrogen receptor (ER)/progesterone receptor (PR) for breast cancer; fibrin/fibrinogen for bladder cancer; HE4 for ovarian cancer; HER2/neu gene amplification or protein overexpression for breast cancer, gastric cancer, and gastroesophageal junction adenocarcinoma; immunoglobulins for multiple myeloma and Waldenström macroglobulinemia; KRAS gene mutation analysis for colorectal cancer and non-small cell lung cancer; lactate dehydrogenase for germ cell tumors, lymphoma, leukemia, melanoma, and neuroblastoma; neuron-specific enolase (NSE) for small cell lung cancer and neuroblastoma; nuclear matrix protein 22 for bladder cancer; prostate-specific antigen (PSA) for prostate cancer; thyroglobulin for thyroid cancer; and urokinase plasminogen activator (uPA) and plasminogen activator inhibitor (PAI-1) for breast cancer.

The anti-glycosylated ICP antibodies, e.g., an anti-glycPD-L1 antibody, may be used as antitumor agents in a variety of modalities. In a particular embodiment, methods of using an antibody as an antitumor agent are contemplated, and, therefore, comprise contacting a population of tumor cells with a therapeutically effective amount of the antibody, or a composition containing the antibody, for a time period sufficient to block or inhibit tumor cell growth. In an embodiment, contacting a tumor cell in vivo is accomplished by administering to a patient in need, for example, by intravenous, subcutaneous, intraperitoneal, or intratumoral injection, a therapeutically effective amount of a physiologically tolerable composition comprising an anti-glycosylated ICP antibody, or a binding fragment thereof, e.g., an anti-glycPD-L1 antibody or a binding fragment thereof, as described. The antibody may be administered parenterally by injection or by gradual infusion over time. Useful administration and delivery regimens include intravenous, intraperitoneal, oral, intramuscular, subcutaneous, intracavity, transdermal, dermal, peristaltic means, or direct injection into the tissue containing the tumor cells.

Therapeutic compositions comprising antibodies are conventionally administered intravenously, such as by injection of a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required diluent, i.e., carrier, or vehicle. The anti-glycosylated ICP antibody, e.g., an anti-glycPD-L1 antibody, containing compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual.

However, suitable dosage ranges for systemic application are disclosed herein and depend on the route of administration. Suitable regimens for initial and booster administration are also contemplated and may typically involve an initial administration followed by repeated doses at one or more intervals (hours) by a subsequent injection or other administration. Exemplary multiple administrations are suitable for maintaining continuously high serum and tissue levels of antibody. Alternatively, continuous intravenous infusion sufficient to maintain concentrations in the blood in the ranges specified for in vivo therapies are contemplated.

It is contemplated that an anti-glycICP antibody produced by the described methods may be administered systemically or locally to treat disease, such as to inhibit tumor cell growth or to kill cancer cells in cancer patients with locally advanced or metastatic cancers. The antibodies may be administered alone or in combination with anti-proliferative drugs or anticancer drugs. In an embodiment, the anti-glycosylated ICP antibodies are administered to reduce the cancer load in the patient prior to surgery or other procedures. Alternatively, they can be administered at periodic intervals after surgery to ensure that any remaining cancer (e.g., cancer that the surgery failed to eliminate) is reduced in size or growth capacity and/or does not survive. As noted hereinabove, a therapeutically effective amount of an antibody is a predetermined amount calculated to achieve the desired effect. Thus, the dosage ranges for the administration of an anti-glycICP antibody are those large enough to produce the desired effect in which the symptoms of tumor cell division and cell cycling are reduced. Optimally, the dosage should not be so large as to cause adverse side effects, such as hyperviscosity syndromes, pulmonary edema, congestive heart failure, neurological effects, and the like. Generally, the dosage will vary with age of, condition of, size and gender of, and extent of the disease in the patient and can be determined by one of skill in the art such as a medical practitioner or clinician. Of course, the dosage may be adjusted by the individual physician in the event of any complication.

Treatment Methods

In certain embodiments, the compositions and methods involve the administration of an anti-glycosylated ICP antibody, or a binding portion thereof, e.g. anti-glycPD-L1 antibody, that specifically and preferentially binds to glycosylated ICP protein, e.g., PD-L1, alone, or in combination with a second or additional drug or therapy. Such drug or therapy may be applied in the treatment of any disease that is associated with a human glycosylated ICP interacting with its ligand, for example, with the interaction of human PD-L1 or glycosylated human PD-L1 with human PD-1. For example, the disease may be a cancer. In a particular and exemplary embodiment, the compositions and methods comprising at least one anti-PD-L1 antibody that binds to glycosylated PD-L1 protein, or a binding portion thereof, have a therapeutic or protective effect in the treatment of a cancer or other disease, particularly by preventing, reducing, blocking, or inhibiting the PD-1/PD-L1 interaction, thereby providing a therapeutic effect and treatment.

The compositions and methods, including combination therapies, have a therapeutic or protective effect and may enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve administering an anti-glycosylated ICP antibody or a binding fragment thereof and a second therapy. The second therapy may or may not have a direct cytotoxic effect. For example, the second therapy may be an agent that upregulates the immune system without having a direct cytotoxic effect. A tissue, tumor, and/or cell can be exposed to one or more compositions or pharmacological formulation(s) comprising one or more of the agents (e.g., an antibody or an anti-cancer agent), or by exposing the tissue, tumor, and/or cell with two or more distinct compositions or formulations, wherein one composition provides, for example, 1) an antibody, 2) an anti-cancer agent, 3) both an antibody and an anti-cancer agent, or 4) two or more antibodies. Also, it is contemplated that such a combination therapy can be used in conjunction with chemotherapy, radiotherapy, surgical therapy, or immunotherapy.

By way of example, the terms "contacted" and "exposed," when applied to a cell, are used herein to describe a process by which a therapeutic polypeptide, preferably an anti-glycPD-L1 antibody, is delivered to a target cell or is placed in direct juxtaposition with the target cell, particularly to bind specifically to the target antigen, e.g., PD-L1, particularly, glycosylated PD-L1, on the surface of tumor or cancer cells. Such binding by a therapeutic anti-glycPD-L1 antibody prevents, blocks, inhibits, or reduces the interaction of the tumor or cancer cell-expressed PD-L1 with PD-1 on an effector T-cell, thereby preventing immunosuppression associated with the PD-L1/PD-1 interaction. In embodiments, a chemotherapeutic or radiotherapeutic agent are also administered or delivered to the subject in conjunction with the anti-glycPD-L1 antibody or binding fragment thereof. To achieve cell killing, for example, one or more agents are delivered to a cell in a combined amount effective to kill the cell or prevent it from dividing.

An anti-glycosylated ICP antibody, e.g., an anti-glycPD-L1 antibody, as described herein, may be administered before, during, after, or in various combinations relative to another anti-cancer treatment. The administrations may be in intervals ranging from concurrently to minutes to days to weeks before or after one another. In embodiments in which the antibody is provided to a patient separately from an anti-cancer agent, it would be generally ensured that a significant period of time did not expire between the time of each delivery, such that the administered compounds would still be able to exert an advantageously combined effect for the patient. Illustratively, in such instances, it is contemplated that one may provide a patient with the antibody and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment or treatment cycle will last 1-90 days or more (this range includes intervening days and the last day). It is contemplated that one agent may be given on any day of day 1 to day 90 (this such range includes intervening days and the last day) or any combination thereof, and another agent is given on any day of day 1 to day 90 (this such range includes intervening days and the last day) or any combination thereof. Within a single day (24-hour period), the patient may be given one or multiple administrations of the agent(s). Moreover, after a course of treatment, it is contemplated that there may be a period of time at which no anti-cancer treatment is administered. This time period may last, for example, for 1-7 days, and/or 1-5 weeks, and/or 1-12 months or more (this such range includes intervening days and the upper time point), depending on the condition of the patient, such as prognosis, strength, health, etc. Treatment cycles would be repeated as necessary. Various combinations of treatments may be employed. In the representative examples of combination treatment regimens shown below, an antibody, such as an anti-glycosylated ICP antibody, e.g., an anti-glycPD-L1 antibody, or binding fragment thereof is represented by "A" and an anti-cancer therapy is represented by "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A.

Administration of any antibody or therapy of the present embodiments to a patient will follow general protocols for the administration of such compounds, taking into account the toxicity, if any, of the agents. Therefore, in some embodiments there is a step of monitoring adverse events and toxicity, particularly those that may be attributable to combination therapy.

In an embodiment, a therapeutic or treatment method involves the administration of an anti-glycosylated ICP antibody alone or in combination with another anticancer agent to a patient in need thereof, i.e., a patient with a cancer or tumor. Prior to administration of the anti-glycosylated ICP antibody, a sample of the patient's tumor or cancer may be evaluated for the presence of the ICP. If the results of such an evaluation reveals that the patient's tumor or cancer is positive for glycosylated ICP, the patient would be selected for treatment based on the likelihood that patient's glycosylated-ICP+ tumor or cancer would be more amenable to treatment with the anti-glycosylated ICP antibody and treatment may proceed with a more likely beneficial outcome. A medical professional or physician may advise the patient to proceed with the anti-glycosylated ICP antibody treatment method, and the patient may decide to proceed with treatment based on the advice of the medical professional or physician. In addition, during the course of treatment, the patient's tumor or cancer cells may be assayed for the presence of the glycosylated ICP as a way to monitor the progress or effectiveness of treatment. If the assay shows a change, loss, or decrease, for example, in glycosylated ICP on the patient's tumor or cancer cells, a decision may be taken by the medical professional in conjunction with the patient as to whether the treatment should continue or be altered in some fashion, e.g., a higher dosage, the addition of another anti-cancer agent or therapy, and the like.

Immunotherapy

In some embodiments of the methods, immunotherapies may be used in combination or in conjunction with administration of anti-glycICP antibodies. In the context of cancer treatment, immunotherapeutics generally rely on the use of immune effector cells and molecules to target and destroy cancer cells. Rituximab (RITUXAN®) is such an example. Checkpoint inhibitors, such as, for example, ipilumimab, are another such example. The immune effector may be, for example, an antibody specific for a marker (cell surface protein or receptor) on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target, e.g., the PD-1 on T-cells/PD-L1 on tumor cells interaction. Various effector cells include cytotoxic T cells and NK cells.

In one aspect of immunotherapy, the tumor cell must bear some marker (protein/receptor) that is amenable to targeting. Optimally, the tumor marker protein/receptor is not present on the majority of other cells, such as non-cancer cells or normal cells. Many tumor markers exist and any of these may be suitable for targeting by another drug or therapy administered with an anti-glycICP antibody in the context of the present embodiments. Common tumor markers include, for example, CD20, carcinoembryonic antigen (CEA), tyrosinase (p9'7), gp68, TAG-72, HMFG, Sialyl Lewis Antigen, MucA, MucB, PLAP, laminin receptor, erbB, and p155. An alternative aspect of immunotherapy is to combine anticancer effects with immune stimulatory effects. Immune stimulating molecules also exist and include cytokines, such as IL-2, IL-4, IL-12, GM-CSF, gamma-IFN; chemokines, such as MIP-1, MCP-1, IL-8; and growth factors, such as FLT3 ligand.

Examples of immunotherapies currently under investigation or in use are immune adjuvants, e.g., *Mycobacterium bovis*, *Plasmodium falciparum*, dinitrochlorobenzene, and aromatic compounds (U.S. Pat. Nos. 5,801,005 and 5,739,169; Hui and Hashimoto, 1998, *Infection Immun.*, 66(11): 5329-5336; Christodoulides et al., 1998, *Microbiology*, 144 (Pt 11):3027-3037); cytokine therapy, e.g., α, β, and γ interferons; IL-1, GM-CSF, and TNF (Bukowski et al., 1998, *Clinical Cancer Res.*, 4(10):2337-2347; Davidson et al., 1998, *J. Immunother* 21(5):389-398; Hellstrand et al., 1998, *Acta Oncologica*, 37(4):347-353); gene therapy, e.g., TNF, IL-1, IL-2, and p53 (Qin et al., 1998, *Proc. Natl. Acad. Sci. USA*, 95(24):14411-14416; Austin-Ward et al., 1998, *Revista Medial de Chile*, 126(7):838-845; U.S. Pat. Nos. 5,830,880 and 5,846,945); and monoclonal antibodies, e.g., anti-CD20, anti-ganglioside GM2, and anti-p185 (Hollander, 2012, *Front. Immun.*, 3:3; Hanibuchi et al., 1998, *Int. J. Cancer*, 78(4):480-485; U.S. Pat. No. 5,824,311). It is contemplated that one or more anti-cancer therapies may be employed with the antibody therapies described herein.

Protein Purification

Protein, including anti-glycosylated ICP antibody, purification techniques are well known to those of skill in the art. These techniques involve, at one level, the homogenization and crude fractionation of the cells, tissue, or organ into polypeptide and non-polypeptide fractions. The protein or polypeptide of interest may be further purified using chromatographic and electrophoretic techniques to achieve partial or complete purification (or purification to homogeneity) unless otherwise specified. Analytical methods particularly suited to the preparation of a pure protein or peptide are ion-exchange chromatography, size-exclusion chromatography, reverse phase chromatography, hydroxyapatite chromatography, polyacrylamide gel electrophoresis, affinity chromatography, immunoaffinity chromatography, and isoelectric focusing. A particularly efficient method of purifying peptides is fast-performance liquid chromatography (FPLC) or even high-performance liquid chromatography (HPLC). As is generally known in the art, the order of conducting the various purification steps may be changed, and/or certain steps may be omitted, and still result in a suitable method for the preparation of a substantially purified polypeptide.

A purified polypeptide, such as an anti-glycosylated ICP, e.g., anti-glycPD-L1 antibody, refers to a polypeptide which is isolatable or isolated from other components and purified to any degree relative to its naturally-obtainable state. An isolated or purified polypeptide, therefore, also refers to a polypeptide free from the environment in which it may naturally occur, e.g., cells, tissues, organs, biological samples, and the like. Generally, "purified" will refer to a polypeptide composition that has been subjected to fractionation to remove various other components, and which composition substantially retains its expressed biological activity. A "substantially purified" composition refers to one in which the polypeptide forms the major component of the composition, and as such, constitutes about 50%, about 60%, about 70%, about 80%, about 90%, about 95%, or more of the protein component of the composition.

Various methods for quantifying the degree of purification of polypeptides, such as antibody proteins, are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "fold purification number." The actual units used to represent the amount of activity will, of course, be dependent upon the particular assay technique chosen to follow the purification, and whether or not the expressed polypeptide exhibits a detectable activity.

There is no general requirement that the polypeptide will always be provided in its most purified state. Indeed, it is contemplated that less substantially purified products may have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "fold" purification than the same technique utilizing a low pressure chromatography system. Methods exhibiting a lower degree of relative purification may have advantages in total recovery of protein product, or in maintaining the activity of an expressed protein.

Affinity chromatography is a chromatographic procedure that relies on the specific affinity between a substance (protein) to be isolated and a molecule to which it can specifically bind, e.g., a receptor-ligand type of interaction. The column material (resin) is synthesized by covalently coupling one of the binding partners to an insoluble matrix. The column material is then able to specifically adsorb the substance from the solution that is passed over the column resin. Elution occurs by changing the conditions to those in which binding will be disrupted/will not occur (e.g., altered pH, ionic strength, temperature, etc.). The matrix should be a substance that does not adsorb molecules to any significant extent and that has a broad range of chemical, physical, and thermal stability. The ligand should be coupled in such a way as to not affect its binding properties. The ligand should also provide relatively tight binding; however, elution of the bound substance should occur without destroying the sample protein desired or the ligand.

Size-exclusion chromatography (SEC) is a chromatographic method in which molecules in solution are separated based on their size, or in more technical terms, their hydrodynamic volume. It is usually applied to large molecules or macromolecular complexes, such as proteins and industrial polymers. Typically, when an aqueous solution is used to transport the sample through the column, the technique is known as gel filtration chromatography, versus the name gel permeation chromatography, which is used when an organic solvent is used as a mobile phase. The underlying principle of SEC is that particles of different sizes will elute (filter) through a stationary phase at different rates, resulting in the separation of a solution of particles based on size. Provided that all of the particles are loaded simultaneously or near simultaneously, particles of the same size should elute together.

High-performance (aka high-pressure) liquid chromatography (HPLC) is a form of column chromatography used frequently in biochemistry and analytical chemistry to separate, identify, and quantify compounds. HPLC utilizes a column that holds chromatographic packing material (stationary phase), a pump that moves the mobile phase(s) through the column, and a detector that shows the retention times of the molecules. Retention time varies depending on the interactions between the stationary phase, the molecules being analyzed, and the solvent(s) used.

Glycosylated ICP as a Biomarker of Patient Benefit from Anti-Glycosylated ICP Antibody Treatment In an embodiment, methods are provided that involve the use of at least one anti-glycosylated ICP antibody as described. Such methods may be useful in biomarker evaluations of the tumor or cancer cells obtained from a subject who has a cancer or tumor. Provided is a method to determine whether a subject who has cancer also has a cancer or tumor that expresses a glycosylated ICP as a biomarker of ICP-bearing tumor or cancer cells, such as glycosylated PD-L1, and particularly, a detectable level of glycosylated PD-L1 on the cell surface of such cells. For example, if the subject's cancer or tumor cells are tested and determined to express glycosylated ICP, e.g., PD-L1 on the cell surface, then it is more likely that the subject treated with an anti-glycosylated ICP antibody, e.g., anti-glycPD-L1 antibody as described, either alone, or in combination with another anti-cancer agent, for example, would benefit from the treatment. Such methods comprise obtaining a sample from a subject having a cancer or tumor, testing the sample for the presence of glycosylated ICP, e.g., PD-L1, on cells derived from the subject's cancer or tumor using binding methods known and used in the art, or as described supra, and administering to the subject an effective amount of an anti-glycosylated ICP antibody, e.g., an anti-glycPD-L1 antibody, alone, or in combination with another anti-cancer agent, if the subject's cancer or tumor is found to be positive for the cell surface expression of glycosylated ICP, e.g., PD-L1 protein. Diagnosing the subject as having a cancer or tumor expressing glycosylated ICP, e.g., PD-L1, prior to treatment allows for more effective treatment and benefit to the subject, as the administered anti-glycosylated ICP antibody, e.g., anti-glycPD-L1 antibody, is more likely to block or inhibit the interaction of the subject's glycosylated ICP, e.g., glycPD-L1-expressing cancer or tumor cells with the subject's ICP-expressing T-cells, e.g., PD-1-expressing T-cells, thereby preventing immunosuppression of the T-cell activity and promoting killing of the tumor or cancer cells by activated T-cell killing. In an embodiment, the method may involve first selecting a subject whose cancer or tumor may be amenable to testing for the presence of expressed glycosylated ICP, e.g., glycosylated PD-L1 protein.

Similar methods may be used to monitor the presence of glycosylated ICP, e.g., glycosylated PD-L1, on a patient's tumor cells during a course of cancer treatment or therapy, including combination treatments with an anti-glycosylated ICP antibody, e.g., an anti-glycPD-L1 antibody, and another anticancer drug or treatment, over time, as well as after treatment has ceased. Such methods may also be used in companion diagnostic methods in which an anti-cancer treatment regimen, or combination treatment, involves testing or assaying a patient's tumor or cancer sample for glycosylated ICP-expressing tumor or cancer cells, e.g., glycosylated PD-L1-expressing tumor or cancer cells, prior to treatment and during the course of treatment, e.g., monitoring, to determine a successful outcome or the likelihood thereof.

Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions may increase the anti-hyperproliferative effects on the neighboring hyperproliferative cell population. In other embodiments, cytostatic or differentiation agents may be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

Fusions and Conjugates

The anti-glycosylated ICP antibodies provided herein can also be expressed as fusion proteins with other proteins or chemically conjugated to another moiety. In some embodiments, the antibodies or polypeptides have an Fc portion that can be varied by isotype or subclass, can be a chimeric or hybrid, and/or can be modified, for example to improve effector functions, control half-life or tissue accessibility, augment biophysical characteristics, such as stability, and improve efficiency of production, which can be associated with cost reductions. Many modifications useful in the construction of fusion proteins and methods for making them are known in the art, for example, as reported by Mueller, J. P. et al., 1997, *Mol. Immun.* 34(6):441-452; Swann, P. G., 2008, *Curr. Opin. Immunol.*, 20:493-499; and Presta, L. G., 2008, *Curr. Opin. Immunol.*, 20:460-470. In some embodiments, the Fc region is the native IgG1, IgG2, or IgG4 Fc region of the antibody. In some embodiments, the Fc region is a hybrid, for example a chimera containing IgG2/IgG4 Fc constant regions. Modifications to the Fc region include, but are not limited to, IgG4 modified to prevent binding to Fc gamma receptors and complement; IgG1 modified to improve binding to one or more Fc gamma receptors; IgG1 modified to minimize effector function (amino acid changes); IgG1 with altered/no glycan (typically by changing expression host); and IgG1 with altered pH-dependent binding to FcRn. The Fc region can include the entire hinge region, or less than the entire hinge region of the antibody.

Another embodiment includes IgG2-4 hybrids and IgG4 mutants that have reduced binding to FcR which increase their half-life. Representative IG2-4 hybrids and IgG4 mutants are described, for example, in Angal et al., 1993, *Molec. Immunol.*, 30(1):105-108; Mueller et al., 1997, *Mol. Immun.*, 34(6):441-452; and U.S. Pat. No. 6,982,323; all of which are hereby incorporated by references in their entireties. In some embodiments, the IgG1 and/or IgG2 domain is deleted. For example, Angal et al., Id., describe proteins in which IgG1 and IgG2 domains have serine 241 replaced with a proline. In some embodiments, fusion proteins or polypeptides having at least 10, at least 20, at least 30, at least 40, at least 50, at least 60, at least 70, at least 80, at least 90 or at least 100 amino acids are contemplated.

In some embodiments, anti-glycosylated ICP antibodies are linked to or covalently bind or form a complex with at least one moiety. Such a moiety may be, but is not limited to, one that increases the efficacy of the antibody as a diagnostic or a therapeutic agent. In some embodiments, the moiety can be an imaging agent, a toxin, a therapeutic enzyme, an antibiotic, a radio-labeled nucleotide, a chemotherapeutic agent, and the like.

In some embodiments, the moiety that is conjugated or fused to an anti-glycICP antibody may be an enzyme, a hormone, a cell surface receptor, a toxin, such as, without limitation, abrin, ricin A, pseudomonas exotoxin (i.e., PE-40), diphtheria toxin, ricin, gelonin, or pokeweed antiviral protein), a protein (such as tumor necrosis factor, interferon (e.g., α-interferon, β-interferon), nerve growth factor (NGF), platelet derived growth factor (PDGF), tissue plasminogen activator (TPA), or an apoptotic agent (e.g., tumor necrosis factor-α, tumor necrosis factor-β)), a biological response modifier (such as, for example, a lymphokine (e.g., interleukin-1 ("IL-1"), interleukin-2 ("IL-2"), interleukin-6 ("IL-6")), granulocyte macrophage colony stimulating factor ("GM-CSF"), granulocyte colony stimulating factor ("G-CSF"), or macrophage colony stimulating factor, ("M-CSF")), or growth factors (e.g., growth hormone ("GH")), a cytotoxin (e.g., a cytostatic or cytocidal agent, such as paclitaxel, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, a tubulysin-based microtubule inhibitor e.g., a Maytansinoid, such as Maytansinoid DM1 (N2'-deacetyl-N2'-(3-mercapto-1-oxopropyl)-maytansine; mertansine or emtansine, depending on the linker used; and Maytansinoid DM4 (N2'-deacetyl-n2'-(4-Mercapto-4-Methyl-1-oxopentyl)-6-MethylMaytansine; ravtansine), ImmunoGen, Inc., Waltham, MA), and puromycin and analogs or homologs thereof), antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, BiCNU® (carmustine; BSNU) and lomustine (CCNU), cyclophosphamide, busulfan, dibromomannitol, streptozocin, mitomycin C, and cisdichlorodiamine platinum (II) (DDP) cisplatin), an anthracycline (e.g., daunorubicin (formerly daunomycin) and doxorubicin), an antibiotic (e.g., dactinomycin (formerly actinomycin), bleomycin, mithramycin, and anthramycin (AMC)), an anti-mitotic agent and/or tubulin inhibitor, e.g., vincristine and vinblastine, monomethyl auristatin F (MMAF), monomethyl auristatin E (or desmethyl-auristatin E) (MMAE), e.g., vedotin; or combinations thereof.

Antibody-Drug Conjugates (ADCs)

Antibody drug conjugates (ADCs) are biologic therapeutic agents in which potent cytotoxic drugs are covalently linked via chemical linkers or coupling agents to antibodies, typically monoclonal antibodies, which are directed to specific target antigens, in particular, target antigens expressed or overexpressed on the surfaces of tumor or cancer cells.

Such "loaded" antibodies are designed to deliver lethal cytotoxic cargoes to tumor or cancer cells. ADCs provide a means for targeting the payload drug to neoplastic cells while reducing side effects and minimizing systemic toxicity. ADCs bind to the cell surface-expressed target antigen by virtue of the specific interaction of the antibody component of the ADC and its target antigen. After binding to the target antigen, the ADC may be internalized into the cell, particularly, if the antibody has heightened internalization activity. Examples of anti-glycICP antibodies that have internalization function are the anti-glycPD-L1 antibodies of embodiments described herein, such as STM108 and STM073. Accordingly, when such ADCs are internalized into the cell, they act directly to kill the cell or target a molecule inside the cell, which leads to apoptosis or cell death. Such ADCs comprising the anti-glycICP antibodies described herein, e.g., anti-glycPD-L1 antibodies (e.g., STM108 and STM073), particularly, monoclonal, humanized, chimeric, or human antibodies, combine the specific targeting of antibodies to glycosylated ICP on tumor and cancer cells with the cancer-killing ability of cytotoxic drugs or compounds, thereby providing further advantages for treatment and therapies with the anti-glycICP antibodies. Techniques for preparing and using ADCs are known in the art and are not intended to be limiting for the anti-glycPD-L1 antibodies described herein. (See, e.g., Valliere Douglass, J. F., et al., 2015, *Mol. Pharm.*, 12(6):1774-1783; Leal, M. et al., 2014, *Ann. N.Y. Acad. Sci.*, 1321:41-54; Panowski, S. et al., 2014, *mAbs*, 6(1):34-45; Beck, A. 2014, *mAbs*, 6(1):30-33; Behrens, C. R. et al., 2014, *mAbs*, 6(1):46-53; and Flygare, J. A. et al., 2013, *Chem. Biol. Drug Des.*, 81(1): 113-121). In embodiments, some or all of the above-described moieties, particularly, toxins and cytotoxins, may be conjugated to an anti-glycPD-L1 antibody to produce effective ADCs for treating cancer. In embodiments, the anti-glycICP antibody component of the ACD may be a bispecific, multi specific, biparatopic, or multiparatopic antibody.

Techniques for conjugating therapeutic or cytotoxic moieties to antibodies are well known; See, e.g., Amon et al., "*Monoclonal Antibodies For Immunotargeting Of Drugs In Cancer Therapy*", in MONOCLONAL ANTIBODIES AND CANCER THERAPY, Reisfeld et al. (eds.), 1985, pp. 243-56, Alan R. Liss, Inc.); Hellstrom et al., "*Antibodies For Drug Delivery*", in CONTROLLED DRUG DELIVERY (2nd Ed.), Robinson et al. (eds.), 1987, pp. 623-53, Marcel Dekker, Inc.); Thorpe, "*Antibody Carriers Of Cytotoxic Agents In Cancer Therapy: A Review*", in MONOCLONAL ANTIBODIES '84: BIOLOGICAL AND CLINICAL APPLICATIONS, Pinchera et al. (eds.), 1985, pp. 475-506); "*Analysis, Results, And Future Prospective Of The Therapeutic Use Of Radiolabeled Antibody In Cancer Therapy*", in MONOCLONAL ANTIBODIES FOR CANCER DETECTION AND THERAPY, Baldwin et al. (eds.), 1985, pp. 303-16, Academic Press; Thorpe et al., *Immunol. Rev.* 62:119-158 (1982); Carter et al., *Cancer J.* 14(3):154-169 (2008); Alley et al., *Curr. Opin. Chem. Biol.* 14(4):529-537 (2010); Carter et al., *Amer. Assoc. Cancer Res. Educ. Book.* 2005(1):147-154 (2005); Carter et al., *Cancer J.* 14(3):154-169(2008); Chari, *Acc. Chem Res.* 41(1):98-107 (2008); Doronina et al., *Nat. Biotechnol.* 21(7):778-784(2003); Ducry et al., *Bioconjug Chem.* 21(1):5-13(2010); Senter, *Curr Opin. Chem. Biol.* 13(3):235-244 (2009); and Teicher, *Curr Cancer Drug Targets.* 9(8):982-1004 (2009). A review of ADCs and ADC oncology products is found in Lambert, *British J. Clin. Pharmacol.*, 76(2):248-262 (2013) and in Bouchard et al., *Bioorganic & Medicinal Chemistry Letters*, 24:5357-5363 (2014).

In specific embodiments, anti-glycICP antibodies, e.g., anti-glycPD-L1 antibodies, which facilitate the internalization of a glycICP, e.g., PD-L1, into tumor cells, are conjugated to a highly potent biologically active drug or agent, such as a cytotoxic and/or chemotherapeutic agent, a toxin or cytotoxin as noted above, or a radionuclide, typically by chemical linkers with labile bonds, to produce an anti-glycICP antibody-drug conjugate (ADC), called an anti-glycICP antibody-ADC herein. The biologically active drug or cytotoxic agent, for example, serves as a "cytotoxic payload," which is delivered into a cell, particularly a tumor or cancer cell expressing a cell-surface target receptor or molecule that is bound by the anti-glycICP antibody-ADC. Such an anti-glycICP antibody-ADC bound to its target molecule is internalized into the cell where the cytotoxic drug payload is released. Enhancement of the cancer cell-killing activity of the internalizing anti-glycICP antibodies, such as anti-glycPD-L1 antibodies, described herein through conjugation to highly potent cytotoxic payloads affords anti-cancer ADC biologics having high anti-tumor activity and generally mild adverse effects that are well-tolerated.

An anti-glycICP antibody as described in the embodiments herein may be linked to various types of cytotoxic or DNA-acting payloads as known and used in the art, or as yet to be commercialized. For example, maytansine is a benzo-ansamacrolide that was first isolated from the bark of the Ethiopian shrub *Maytenus ovatus*. This cytotoxic agent and derivatives thereof (e.g., maytansinoids) bind to tubulin near the *Vinca* alkaloid binding site. They are considered to have a high affinity for tubulin located at the ends of microtubules and lower affinity to sites distributed throughout the microtubules. The suppression of microtubule dynamics causes cells to arrest in the G2/M phase of the cell cycle, ultimately resulting in cell death by apoptosis. (Oroudjev al., *Mol. Cancer Ther.*, 1012700-2713 (2010)). Two maytansine derivatives (thiol-containing maytansinoids) include DM1 and DM4 (ImmunoGen, Inc., Waltham, MA) have been widely used in combination with irreversible and reversible linkers. In particular, DM1 attached to an antibody with a thioether linker is called "emtansine;" DM1 attached to an antibody with an SPP linker is called "mertansine;". DM4 attached with an SPDB linker is called "ravtansine;" and DM4 attached with an sSPDB linker is called "soravtansine." (ImmunoGen, Inc., Waltham, MA). In an embodiment, the anti-glycICP antibody-ADC comprises the tubulin-acting maytansinoid payload DM1. In a particular embodiment, the anti-glycICP antibody-ADC is anti-glycPD-L1 antibody-DM1. In an embodiment, the anti-glycICP antibody-ADC comprises the tubulin-acting maytansinoid payload DM4. In a particular embodiment, the anti-glycICP antibody-ADC is anti-glycPD-L1 antibody-DM4. In an embodiment, the anti-glycICP antibody-ADC comprises a DNA-acting payload, e.g., DGN462 (Immuno-Gen, Inc., Waltham, MA In a particular embodiment, the anti-glycICP antibody-ADC is anti-glycPD-L1 antibody-DGN462. In an embodiment, the anti-glycPD-L1 antibody component of the anti-glycPD-L1 antibody-ADC is STM073, or a binding portion thereof. In an embodiment, the anti-glycPD-L1 antibody component of the anti-glycPD-L1 antibody-ADC is STM108, or a binding portion thereof.

In a particular embodiment, the cytotoxic agent conjugated to the anti-glycICP antibody is MMAE (monomethyl auristatin E (or desmethyl-auristatin E)), a highly toxic, antineoplastic agent whose antimitotic activity involves inhibiting cell division by blocking the polymerization of tubulin. Vedotin, an International Nonproprietary Name, refers to MMAE plus its linking structure to an antibody in an MMAE-antibody conjugate. In more particular embodiments, the ADC is anti-glycPD-L1 antibody-MMAE, e.g., STM073-MMAE or STM108-MMAE.

A number of chemical linkers are known and used for conjugating a cytotoxic or DNA-acting drug payload to an antibody to produce ADCs. Certain linkers embraced for use alone or in combination for producing ADCs comprising the anti-glycICP antibodies, particularly, those that internalize after binding their target as described herein, include SMCC (4-(N-Maleimidomethyl) cyclohexanecarboxylic acid N-hydroxysuccinimide ester); SPDB (N-succinimidyl 3-(2-pyridyldithio)butyrate); SPP (N-succinimidyl 4-(2-pyridyldithio)pentanoate); sulfo-SPDB or sSPDB (N-succinimidyl-4-(2-pyridyldithio)-2-sulfobutanoate); the thioether linker succinimidyl-4-(N-maleimidomethyl)cyclohexane-1-carboxylate (MCC); and vc (valine-citrulline dipeptide linker). By way of example, engineered linkers (e.g., SMCC, SPDB, S-SPDB), (Immunogen, Inc.) have been designed to be stable prior to the binding of an ADC to a tumor and then to optimize payload efficacy once the ACD is internalized inside a cancer cell. Other linkers, such as the dipeptide vc linker, which is a cathepsin-cleavable linker, may be used to conjugate an antibody to a cytotoxic agent, such as an auristatin which is a mitotic inhibitor derived from dolastatin 10, e.g., monomethylauristatin E (MMAE), e.g., vedotin. The cytotoxins may be conjugated to the antibody such that more than one toxin molecule is attached to each antibody molecule, for example, there may be, on average, 2, 3, 4, 5, 6, 7 or 8 toxin molecules per antibody.

In a particular embodiment, MMAE is indirectly linked to antibody cysteines by a maleimidocaproyl (MC) attachment group, which is coupled to valine-citrulline-p-aminobenzyloxycarbonyl-MMAE (MC-vc-PAB-MMAE). In the "MC-vc-PAB-MMAE" linear structure, "MC" consists of maleimide and caproic acid and is the moiety that attaches to an antibody, typically via cysteine groups on the H chain. In turn, "MC" is attached to a "vc" linker which consists of valine (Val) and citruline (Cit) and which is a cathepsin-cleavable linker that is cleaved by cathepsin inside of tumor or cancer cells. "vc" is attached to the spacer "PAB", i.e., paraminobenzoic acid, to which the MMAE cytotoxin is linked. MC-vc-PAB-MMAE ADCs release free, membrane-permeable MMAE when cleaved by proteases such as cathepsin B. In an embodiment, the linker to the antibody is stable in extracellular fluid, but is cleaved by cathepsin once the ADC has entered a tumor or cancer cell, thus activating the antimitotic mechanism of MMAE or other toxin drug. In another embodiment, monomethylauristatin F, (MMAF) is linked to antibody cysteines by maleimidocaproyl (MC-MMAF). In contrast to MC-vc-PAB-MMAE ADCs, MC-MMAF ADCs are uncleavable, like MCC-DM1 ADCs, and must be internalized and degraded within a cell, releasing cysteine-MC-MMAF as the active drug inside the cell.

In an embodiment, the cytotoxic payload is released in the lysosome following internalization of the ADC into a cell. In the lysosome, lysosomal enzymes digest the antibody component of the ADC. Following lysosomal degradation, the drug (and drug-linker) payload is released into the cytoplasm, where the drug binds intracellular targets, ultimately causing cell death. Optimally, the released payload is fully active, with the linker still attached. In other embodiments in which the target bound to the ADC results in poor trafficking to the lysosome, linkers which are stable outside of the target cell, but which cleave the payload from the antibody component once inside the cell provide an alternative mode for payload release within the cell, but outside of the lysosome. In other embodiments, the linker is stable in extracellular fluid, but is cleaved by cathepsin once the ADC has entered a tumor or cancer cell, thus activating the antimitotic or other cytotoxic mechanism of the toxin drug. In other embodiments, a payload released by the action of cleavable linkers is able to enter a neighboring cancer cells and kill them via a bystander effect, thus augmenting the targeting and tumor killing activity of an ADC.

By way of particular example, an anti-glycICP antibody, as represented by the anti-PD-L1 MAbs STM073 or STM108 that promote internalization of cell surface PD-L1, is coupled to DM1 via the linker SMCC (succinimidyl 4-(N-maleimidomethyl)cyclohexane-1-carboxylate). In another particular example, an anti-glycICP antibody as represented by STM073 or STM108, is coupled to DM4 via the linker SPDB (N-succinimidyl 3-(2-pyridyldithio)butyrate) or sSPDB (N-succinimidyl-4-(2-pyridyldithio)-2-sulfobutanoate). In another particular example, the auristatin monomethylauristatin E is linked to cysteine residues of an anti-glycICP antibody, e.g., STM073 or STM108, by maleimidocaproyl-valine-citrulline-p-aminobenzyloxycarbonyl (MC-vc-PAB-MMAE). In particular examples, the ADC is STM108-MC-vc-PAB-MMAE or STM073-MC-vc-PAB-MMAE.

In an embodiment, the anti-glycICP antibody-ADC comprises multiple units of a drug, such as MMAE, per molecule, such as 1-10, 1-5, 2-5, 3-5, or 2, 3, 4, 5, 6, 7, 8, 9, 10 units of drug, such as MMAE, per molecule, as well as values therebetween. In other embodiments, the antibody-drug ratio may be 2, 3, 4, 5, 6, 7, 8, 9, 10, or greater, as well as ranges between 2-10 and values therebetween. In embodiments, the anti-glycICP antibody, e.g., STM108 or STM073, is a bispecific, multispecific, biparatopic, or multiparatopic antibody, or an antigen binding portion thereof. Such ADCs comprising an anti-glycICP antibody having internalizing function as described herein, e.g., the above-mentioned STM108-MC-vc-PAB-MMAE, provide bolstered and multifaceted antineoplastic effects in the killing of tumor and cancer cells for cancer treatment. As but a few illustrative advantages, an anti-human glycICP MAb-ADC, e.g., STM108-ADC, can block the PD-1/PD-L1 interaction, thereby enhancing T cell immunity and effector function against tumor cells; it can selectively target glycosylated PD-L1 expressed on tumor and cancer cells; it can internalize PD-L1 on tumor or cancer cells after binding, thereby reducing the surface-expressed PD-L1 on tumor or cancer cells and further reducing the oncogenic potential of PD-L1; it can cause apoptosis of tumor or cancer cells into which antibody is internalized and the toxic drug is released to damage and ultimately kill the cell; and it can facilitate a bystander effect by killing nearby or neighboring tumor or cancer cells through the release of toxic drug from the apoptosed tumor or cells.

In some embodiments, antibodies as described herein may be conjugated to a marker, such as a peptide, to facilitate purification. In some embodiments, the marker is a hexahistidine peptide, i.e., the hemagglutinin "HA" tag, which corresponds to an epitope derived from the influenza hemagglutinin protein (Wilson, I. A. et al., *Cell,* 37:767-778 (1984)), or the "flag" tag (Knappik, A. et al., *Biotechniques* 17(4):754-761 (1994)).

In other embodiments, the moiety conjugated to the anti-glycICP antibodies as described herein may be an imaging agent that can be detected in an assay. Such imaging agents may be enzymes, prosthetic groups, radiolabels, nonradioactive paramagnetic metal ions, haptens, fluorescent labels, phosphorescent molecules, chemiluminescent molecules, chromophores, luminescent molecules, bioluminescent molecules, photoaffinity molecules, or colored particles or ligands, such as biotin. In embodiments, suitable enzymes include, but are not limited to, horseradish peroxidase, alkaline phosphatase, beta-galactosidase, or acetylcholinesterase; prosthetic group complexes include, but are not limited to, streptavidin/biotin and avidin/biotin; fluorescent materials include, but are not limited to, umbelliferone, fluorescein, fluorescein isothiocyanate, rhodamine, dichlorotriazinylamine fluorescein, dansylchloride or phycoerythrin; luminescent materials include, but are not limited to, luminol; bioluminescent materials include, but are not limited to, luciferase, luciferin, and aequorin; radioactive materials include, but are not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In), iodine ($^{131}$I, $^{125}$I, $^{123}$I, $^{121}$I), lanthanum ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re) rhodium ($^{105}$Rh), ruthemium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb) yttrium ($^{90}$Y), zinc ($^{65}$Zn); positron emitting metals using various positron emission tomographies, and nonradioactive paramagnetic metal ions.

The imaging agent may be conjugated to the antibodies or polypeptides described herein either directly or indirectly through an intermediate (such as, for example, a linker known in the art) using techniques known in the art. See, for example, U.S. Pat. No. 4,741,900 which reports on metal ions that can be conjugated to antibodies and other molecules as described herein for use as diagnostics. Some conjugation methods involve the use of a metal chelate complex employing, for example, an organic chelating agent, such as diethylenetriaminepentaacetic acid anhydride (DTPA); ethylenetriaminetetraacetic acid; N-chloro-p-toluenesulfonamide; and/or tetrachloro-3-6α-diphenylglycouril-3, attached to the antibody. Monoclonal antibodies can also be reacted with an enzyme in the presence of a coupling agent such as glutaraldehyde or periodate. Conjugates with fluorescein markers can be prepared in the presence of these coupling agents or by reaction with an isothiocyanate.

In some embodiments, the anti-glycICP antibodies as described herein may be conjugated to a second antibody to form an antibody heteroconjugate, for example, as described in U.S. Pat. No. 4,676,980. Such heteroconjugate antibodies can additionally bind to haptens (e.g., fluorescein), or to cellular markers, cytokines, or chemokines.

In some embodiments, the anti-glycosylated ICP antibodies described herein can also be attached to solid supports, which can be useful for carrying out immunoassays or purification of the target antigen or of other molecules that are capable of binding to the target antigen that has been immobilized to the support via binding to an antibody or antigen binding fragment as described herein. Such solid supports include, but are not limited to, glass, cellulose, polyacrylamide, nylon, polystyrene, polyvinyl chloride or polypropylene.

EXAMPLES

The Examples herein relate to a specific and representative ICP, namely, PD-L1, found by the inventors to be stably expressed in glycosylated form on tumor and cancer cells, and antibodies generated against the glycosylated form of PD-L1 and peptides thereof. Representative anti-glycPD-L1 antibodies isolated by the described methods and exemplified herein include STM004, STM115, STM073 and STM108. The antibodies STM004 and STM115 are disclosed in PCT publication WO2016/160792, published Oct. 6, 2016; the antibodies STM073 and STM108 are disclosed in U.S. provisional application Ser. No. 62/361,312, filed Jul. 12, 2016. One having skill in the art will appreciate that Examples may embrace other glycosylated ICP expressed on tumor cells, in addition to PD-L1, and their ligand ICPs expressed on immune cells, such as effector T cells.

Example 1 Materials and Methods

Cell Culture, Stable Transfectants, and Transfection. All cells were obtained from American Type Culture Collection (ATCC). These cells were grown in in DMEM/F12 or RPMI 1640 medium supplemented with 10% fetal bovine serum (FBS). PD-L1 stable transfectants in MDA-MB-468, BT549 and 293T cells were selected using puromycin (InvivoGen, San Diego, CA, USA). For transient transfection, cells were transiently transfected with DNA, such as DNA encoding PD-L1, using SN liposomes (Hu, M. C. et al., 2004, *Cell*, 117:225-237) and Lipofectamine™ 2000 (Life Technologies, Carlsbad, CA, USA).

Generation of Stable Cells Using Lentiviral Infection. The lentiviral-based shRNA (pGIPZ plasmids) used to knockdown expression of PD-L1 (Shen, J. et al., 2013, *Nature*, 497:383-387) in cells was purchased from the shRNA/ORF Core Facility (UT MD Anderson Cancer Center). Based on knock-down efficiency of PD-L1 protein expression in MDA-MB-231 or A431 cells, the inventors selected two shPD-L1 clones for this study. The mature antisense sequences are as follows: TCAATTGTCATATTGCTAC (shPD-L1 #1, SEQ ID NO: 9), TTGACTC-CATCTTTCTTCA (shPD-L1 #5, SEQ ID NO: 10). Using a pGIPZ-shPD-L1/Flag-PD-L1 dual expression construct to knock down endogenous PD-L1 and reconstitute Flag-PD-L1 simultaneously, the inventors established endogenous PD-L1 knock-down and Flag-PD-L1 WT or 4NQ mutant expressing cell lines. To generate lentivirus-expressing shRNA for PD-L1 and Flag-PD-L1, the inventors transfected 293T cells with pGIPZ-non-silence (for vector control virus), pGIPZ-shPD-L1, or pGIPZ-shPD-L1/PD-L1 WT, or pGIPZ-shPD-L1/PD-L1 4NQ mutant with FuGENE 6 transfection reagent. Twenty-four hours after transfection the medium was changed, and then the medium was collected at 24-hour intervals. The collected medium containing lentivirus was centrifuged to eliminate cell debris, and filtered through 0.45-µm filters. Cells were seeded at 50% confluence 12 hours before infection, and the medium was replaced with medium containing lentivirus. After infection for 24 hours, the medium was replaced with fresh medium and the infected cells were selected with 1 µg/ml puromycin (InvivoGen).

Plasmids. A human PD-L1 clone was obtained from the shRNA/ORF Core Facility (UT MD Anderson Cancer Center, Houston, TX, USA) and cloned into pCDH lentiviral expression vectors to establish PD-L1-Flag or PD-L1-Myc expression cell lines using known molecular biological techniques. In addition, human PD-L1 nucleic acid was also cloned into pEGFP-N1 and pCMV-HA mammalian cell expression vectors for transient transfection. pCDH/PD-L1-Flag expression vector was used as a template to generate the PD-L1-Flag NQ mutants N35Q, N192Q, N200Q, N219Q, and 4NQ (N35Q/N192Q/N200Q/N219Q) by performing site directed mutagenesis using primers presented in Table 4 below. To create a pGIPZ-shPD-L1/Flag-PD-L1 dual expression construct to knock down endogenous PD-L1 and reconstitute Flag-PD-L1 simultaneously, a shPD-L1 construct (shPD-L1 #5) which targets the 3»-UTR region of PD-L1 mRNA was selected. The Flag-PD-L1 wild type (WT) or 4NQ mutant DNA was cloned into pGIPZ-shPD-L1 (Thermo Scientific, Pittsburgh, PA, USA) which expresses shRNA specific for endogenous PD-L1. All constructs were confirmed using enzyme digestion and DNA sequencing.

Statistical analysis. Data in bar graphs represents mean fold change relative to untreated or control groups with standard deviation of three independent experiments. Statistical analyses were performed using SPSS (Ver. 20, SPSS, Chicago, IL). The correlation between protein expression and BLBC subset was analyzed using Spearman's correlation and Mann-Whitney test. Student's t test was performed for experimental data. A P value <0.05 was considered statistically significant.

TABLE 4

Primers for site directed mutagenesis

| Primers | | | Sequences (5' to 3') |
|---|---|---|---|
| N35Q | Forward | (SEQ ID NO: 11) | gtggtagagtatggtagccaaatgacaattgaatgcaaa |
| | Reverse | (SEQ ID NO: 12) | tttgcattcaattgtcatttggctaccatactctaccac |
| N192Q | Forward | (SEQ ID NO: 13) | gagaggagaagcttttccaggtgaccagcacactgag |
| | Reverse | (SEQ ID NO: 14) | ctcagtgtgctggtcacctggaaaagcttctcctctc |
| N200Q | Forward | (SEQ ID NO: 15) | gaccagcacactgagaatccagacaacaactaatgagat |
| | Reverse | (SEQ ID NO: 16) | atctcattagttgttgtctggattctcagtgtgctggtc |
| N219Q | Forward | (SEQ ID NO: 17) | gagaggagaagcttttccaagtgaccagcacactgaga |
| | Reverse | (SEQ ID NO: 18) | tctcagtgtgctggtcacttggaaaagcttctcctctctc |

Antibodies and Chemicals. The following antibodies were used in the experiments described in the Examples: Flag (F3165; Sigma-Aldrich, St. Louis, MO, USA); PD-L1 (13684; Cell Signaling Technology, Danvers, MA, USA); PD-L1 (329702; BioLegend, San Diego, CA, USA,); PD-L1 (GTX117446; GeneTex, Irvine, CA, USA); PD-L1 (AF156; R&D Systems, Minneapolis, MN, USA); PD-1 (ab52587; Abcam, Cambridge, MA, USA).

Immunoblot Analysis and Immunocytochemistry. Immunoblot analysis was performed as described previously (Lim et al., 2008, *Gastroenterology*, 135:2128-2140; and Lee et al., 2007, Cell, 130:440-455). Image acquisition and quantification of band intensity were performed using an Odyssey® infrared imaging system (LI-COR Biosciences, Lincoln, NE, USA). For immunocytochemistry, cells were fixed in 4% paraformaldehyde at room temperature for 15 minutes, permeabilized in 5% Triton X-100 for 5 minutes, and then were stained using primary antibodies. The secondary antibodies used were anti-mouse Alexa Fluor 488 or 594 dye conjugate and/or anti-rabbit Alexa Fluor 488 or 594 dye conjugate (Life Technologies). Nuclei were stained with 4',6-diamidino-2-phenylindole (DAPI blue) (Life Technologies). After mounting, the cells were visualized using a multiphoton confocal laser-scanning microscope (Carl Zeiss, Thornwood, NY, USA).

PD-L1 and PD-1 Interaction Assay. To measure the interaction of PD-1 protein and PD-L1 protein, cells were fixed in 4% paraformaldehyde at room temperature for 15 minutes and then were incubated with recombinant human PD-1 Fc chimera protein (R&D Systems) for 1 hour. The secondary antibodies used were anti-human Alexa Fluor 488 dye conjugate (Life Technologies). Nuclei were stained with 4',6-diamidino-2-phenylindole (DAPI blue) (Life Technologies). The fluorescence intensity of Alexa Fluor 488 dye was then measured using a microplate reader Synergy Neo (BioTeK, Winooski, VT, USA) and normalized to the intensity by total protein quantity. To take an image, after mounting, the cells were visualized using a confocal laser-scanning microscope (Carl Zeiss).

Example 2 Production of and Screening for Glycosylated PD-L1-Binding Antibodies

This representative Example provides a description of obtaining monoclonal antibodies that specifically bind a glycosylated ICP, namely, glycosylated PD-L1; however, the methods described herein are applicable to generating antibodies that specifically bind other glycosylated immune checkpoint molecules to inhibit immunosuppression by preventing association of the glycosylated ICP with its interacting ligand.

Hybridomas producing monoclonal antibodies generated against glycosylated human PD-L1 were obtained by the fusion of SP2/0 murine myeloma cells with spleen cells isolated from human PD-L1-immunized BALB/c mice (n=6) (Antibody Solution, Inc.) according to standardized protocol. Before fusion, sera from the immunized mice were validated for binding to the PD-L1 immunogen using FACS analysis. Monoclonal antibody (MAb)-producing hybridomas were generated. The isotype of all of the MAbs was IgG1. The hybridomas that produced antibodies were again tested for specificity for glycosylated PD-L1. To this end, 42 candidate MAb-producing hybridomas were selected, grown in ADCF medium, and their monoclonal antibody-containing supernatant was concentrated and purified.

To identify anti-glycPD-L1 MAbs that were specific for and which preferentially bound glycosylated PD-L1 antigen versus non-glycosylated PD-L1, different types of assays were performed. In a screening assay to detect preferential binding of MAbs to glycosylated PD-L1, antibody binding was determined based on the measurement of fluorescence intensity of a secondary antibody that recognized the antibody being tested through FACS analysis (using membrane bound proteins). By way of example, the assay was performed using the BT549 human breast cancer cell line. Illustratively, BT549 cells overexpressing PD-L1 WT (fully glycosylated) were labeled with biotin according to conventional procedures and then mixed with BT549 cells overexpressing PD-L1 4NQ (fully unglycosylated PD-L1 variant) that were not labeled with biotin. The mixed cells were incubated with antibodies to be tested and recombinant streptavidin conjugated with PE (rSA-PE). The cells and were further incubated with secondary antibodies conjugated with FITC (SA-FITC). After washing, cells were gated to separate the biotin-rSA-PE labeled cells (glycosylated PD-L1) and the cells not labeled with biotin-rSA-PE (the unglycosylated PD-L1 4NQ cells). Mean fluorescence intensity (MFI) was measured to assess relative binding of anti-PD-L1 antibodies to membrane bound WT or 4NQ PD-L1 via secondary antibodies conjugated with FITC (SA-FITC). Antibodies that exhibited significantly higher MFI on WT PD-L1 over 4NQ PD-L1 were selected for further evaluation. Results for the fluorescence binding analysis of the STM004, STM073, STM108, and STM115 anti-glycPD-L1 MAbs are presented in Table 5 below, which shows the MFI values for antibody binding to BT549 cells expressing wild type (glycosylated) PD-L1, (BT549PD-L1WT Cells) versus antibody binding to BT549 cells expressing variant (non-glycosylated 4NQ) PD-L1, (BT549PD-L1 4NQ Cells).

TABLE 5

Mean Fluorescence Intensity Values for Anti-glycPD-L1 MAbs

| MAb | MFI (BT549PD-L1WT Cells) | MFI (BT549PD-L1 4NQ Cells) |
|---|---|---|
| STM004 | 42.53 | 8.70 |
| STM073 | 63.90 | 12.21 |
| STM108 | 117.42 | 27.57 |
| STM115 | 51.14 | 21.31 |

In another assay, both glycosylated human PD-L1 protein and non-glycosylated PD-L1, i.e., PD-L1 protein treated with PNGase F, were coated onto a solid phase and tested for binding affinity of the MAbs to the PD-L1 antigens. It will be understood that "PD-L1 antigen" is synonymous with "PD-L1 protein." Twelve (12) of the MAbs showed a higher affinity interaction with glycosylated PD-L1 protein compared to non-glycosylated PD-L1 protein (PNGase F treated protein). For further specificity analysis, selected MAbs were analyzed by Western Blot and FACS flow cytometry analysis. From the various analyses, MAbs, such as STM004, STM073, STM108, and STM115 were found to specifically bind the glycosylated form of PD-L1 compared with the non-glycosylated form of PD-L1, which further validated the specificity of these MAbs for glycosylated PD-L1 antigen. See FIG. 1.

Figure 2:
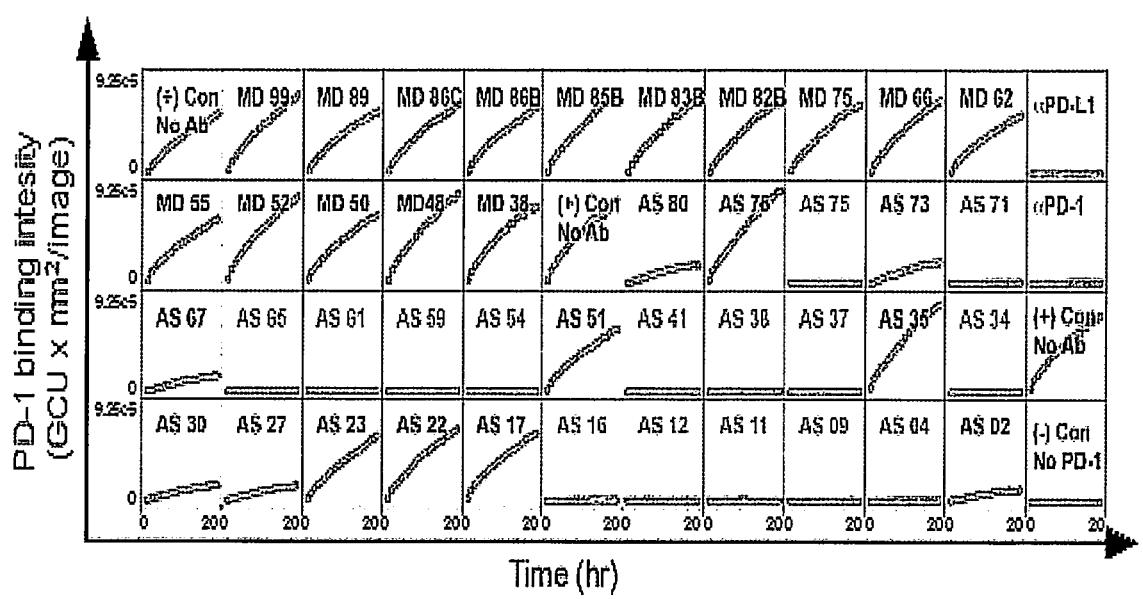
FIG. 2. Blockade of anti-human PD-L1 antibody for PD-L1 and PD-1 binding. PD-L1 expressing BT549 cells were incubated with anti-human PD-L1 antibody and fluorescent labeled PD-1-Fc-fusion protein. Ligand and receptor binding was quantified by IncuCyteTMZoom at every hour. The designations in red indicates that an antibody showed a complete blockade of PD-L1/PD-1 binding.

In some cases, the purified MAbs were further tested for their ability to neutralize or inhibit the interaction between PD-L1 and PD-1 (PD-L1/PD-1 interaction) using a live-cell imaging assay, IncuCyte™, (Essen Bioscience). For this assay, BT-549 cells expressing PD-L1 were incubated with anti-human PD-L1 antibody and with fluorescent-labeled PD-1-Fc fusion proteins. Ligand and receptor binding was quantified by IncyCyte™ Zoom every hour, according to the manufacturer's instructions. Based on this assay and as shown in FIG. 2, of the 42 MAbs tested, 15 MAbs completely blocked the binding of PD-L1 to PD-1.

Preferential binding to glycosylated PD-L1 was confirmed by western blot and flow cytometry analysis. FIG. 3B demonstrates that 5 of the anti-glycPD-L1 antibodies identified by the screening method described herein bind to glycosylated PD-L1 ("WT") but not to the unglycosylated PD-L1 4NQ. FIG. 3C also confirms the preferential binding of these 5 antibodies for glycosylated or WT PD-L1 vs the unglycosylated PD-L1 4NQ mutant by flow cytometry.

Example 3 Identification of Binding Regions of Specific Glycosylated PD-L1-Binding Antibodies To identify the regions of monoclonal anti-glycPD-L1 antibodies which bound to glycosylated PD-L1, wild type (glycosylated) PD-L1 (PD-L1 WT), and the glycosylation variant proteins N35/3NQ, N192/3NQ, N200/3NQ, and N219/3NQ (FIGS. 4A-4C) were overexpressed in PD-L1 knockdown BT549 cells. As determined by Western blot in FIG. 4C, some MAbs recognized particular PD-L1 mutants with higher levels of binding compared with other PD-L1 mutants, demonstrating that such MAbs were site-specific for the glycosylation recognized. Further, Western blot analysis using liver cancer cell lysate also revealed that different anti-glycPD-L1 antibodies recognize different patterns of PD-L1 glycosylation (FIG. 4D).

Example 4 Immunohistochemical Staining Using Anti-glycPD-L1 Antibodies

Figure 5:
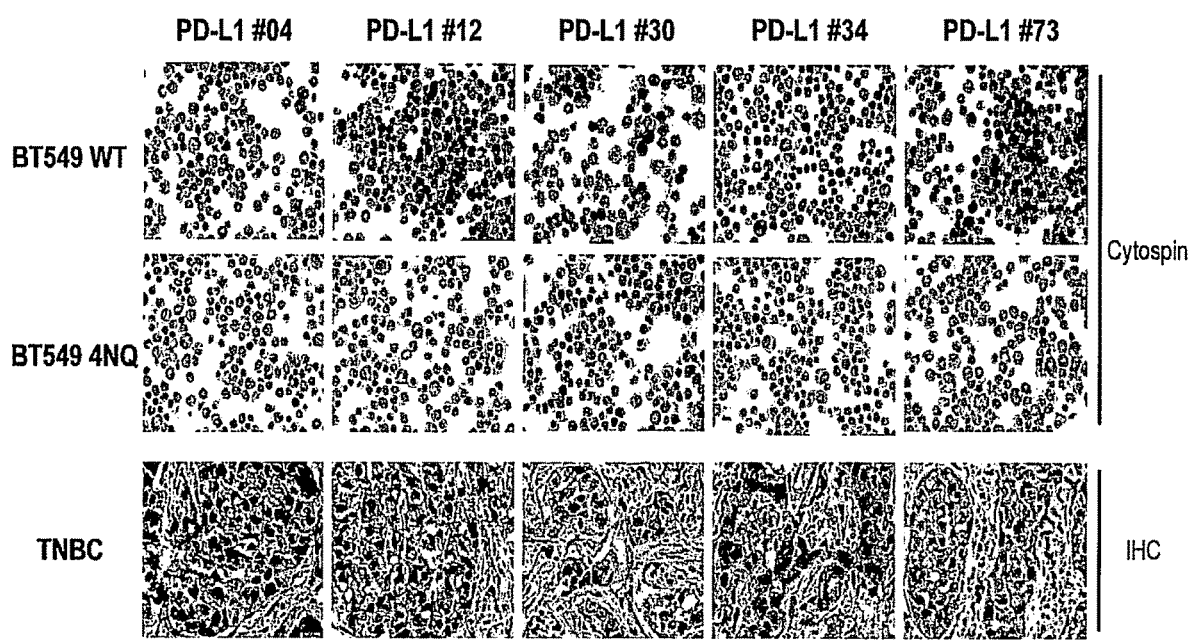
FIG. 5. Characterization of anti-glycosylated PD-L1 monoclonal antibodies by Immunohistochemistry (IHC). For cytospin analysis, BT-549 cells expressing either PD-L1 WT or PD-L1 4NQ protein were spread and stained with 5 anti-glycPD-L1 antibodies. For IHC staining, breast cancer patient samples were stained with anti-glycPD-L1 antibodies.

The histopathologic relevance of these MAbs was further demonstrated by immunohistochemical (IHC) staining as shown in FIG. 5. In a cytospin staining analysis, the anti-glycPD-L1 monoclonal antibodies consistently recognized and bound the glycosylated PD-L1 protein, but not unglycosylated PD-L1 protein. In a human triple negative breast cancer patient sample, the anti-glycPD-L1 monoclonal antibodies also showed membrane and cytoplasm staining in a 1:30 ratio. These data demonstrated that the anti-glycPD-L1 monoclonal antibodies can be used in biomarker analyses for detection of glycosylated PD-L1 as biomarker.

Example 5 Binding Assay

To determine whether an anti-glycPD-L1 monoclonal antibody as described herein specifically inhibits the interaction of PD-1 and PD-L1, the following binding assay was performed. On Day 0 of the assay, serum-containing medium was removed from PD-L1-expressing BT549 target cell culture and gently rinsed twice with D-PBS. Cells were harvested and counted. The cell suspension was centrifuged (1000 RPM, 5 minutes) and the cell pellet was resuspended in culture medium at 50,000 cells/mL. A manual multichannel pipette was used to seed the cells (100 µL/well, i.e., 5000 cells/well) into every well of a flat-bottom microplate. The plate was allowed to stand at ambient temperature for 30 minutes. Thereafter, the plates containing the cells were incubated overnight in a 5% $CO_2$ incubator.

On Day 1 of the assay (i.e., the next morning), culture medium containing 1 µg/mL PD-1/Fc and a 1:400 dilution of Alex Fluor 488-goat anti-human IgG was prepared and warmed to 37° C. in an incubator. The cell plate was removed from the incubator and the medium was aspirated, taking care not to damage the cell layer. 50 µL of test antibody was added to each well in a dose-dependent manner. 50 µL of the culture medium containing PD-1/Fc and Alex Fluor 488-goat anti-human IgG was added to every well. The cell plate was positioned in the IncuCyte ZOOM® instrument and allowed to equilibrate for 20 minutes prior to the first scan. 24-hr automated repeat scanning (10×) was scheduled for every 1-2 hours for up to 24 hours. Objective: 10×; Vessel Type: Corning 3596; Scan Mode: Standard; Scan Pattern: 4 images per well; Channel: Phase+"Green". The binding of different concentrations of representative monoclonal anti-glycPD-L1 antibodies is shown in FIGS. 6A-6C relative to controls (FIG. 6D). FIG. 6A shows results for STM004, FIG. 6B shows results for STM073 and FIG.

6C shows results for STM108. Binding to PD-1 decreased as the concentration of the anti-glycPD-L1 antibody increased, demonstrating that the anti-glycPD-L1 antibody inhibits PD-L1 binding to PD-1.

Example 6 T Cell Killing Assay

T cell killing assays were utilized to determine the cytotoxic activity of anti-glycPD-L1 monoclonal antibodies on tumor cells. The protocol followed is as follows: On Day 0, serum-containing medium was removed from glycosylated wild type PD-L1-(PD-L1 WT) expressing BT549 RFP target cell cultures and gently rinsed twice with PBS. Cells were harvested and counted. The cell suspension was centrifuged (1000 RPM, 4 minutes) and the cell pellet was resuspended in culture medium at 50,000 cells/mL. Using a manual multichannel pipette, the cells were seeded (100 μL/well, i.e., 5000 cells/well) into every well of a flat-bottom microplate. The plate was allowed to stand at ambient temperature for 30 minutes and then was positioned into a IncuCyte ZOOM® live-cell imager where it was left to equilibrate for 20 minutes before scheduling the first scan. Twenty-four hour (24 hr) repeat scanning (10× objective) was scheduled for every 3 hours, with the first scan commencing immediately. Cell confluence was monitored for the next 18 hours (overnight) until the desired confluence (e.g., 20%) was achieved.

The next morning, the day of the assay (i.e., Day 1), a 10 μM solution of IncuCyte™ Caspase 3/7 apoptosis green fluorescence detection reagent (Essen BioScience 4440) was prepared in assay medium (4× final assay concentration of 2.5 μM) and warmed to 37° C. in an incubator. An anti-CD3 antibody (100 ng/mL)+IL-2 (10 ng/mL) T cell activator treatment was prepared at 4× final assay concentration in assay medium and warmed to 37° C. Test MAbs were also prepared. The target cell plate was removed from the incubator and the medium was aspirated, taking care not to damage the cell layer. Using a multichannel pipette, 25 μL of the warmed caspase 3/7 solution was transferred into each well. Thereafter, 25 μL of the warmed anti-CD3 antibody+ IL-2, and the antibodies, were placed into the appropriate wells of the cell plate. An additional 50 μL medium containing the effector cells (PBMCs or Total T cells) was added to form a total assay volume of 100 μL. The de-bubbled cell plate was positioned in the IncuCyte ZOOM® instrument and allowed to equilibrate for 20 minutes prior to the first scan. 24-hr repeat scanning was scheduled for every 2-3 hours for up to 5 days. (Objective 10×; Vessel Type: Corning 3596; Scan Mode: Standard; Scan Pattern: 2 images per well; Channel: Phase+"Green" (+"Red" if NucLight™ Red target cells were used).

Figure 7A:
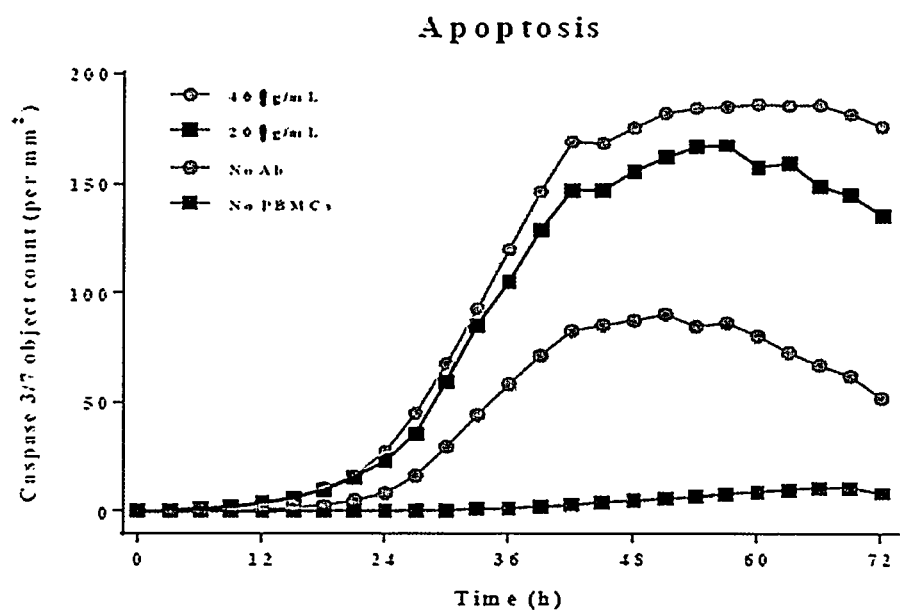
FIGS. 7A and 7B. Anti-glycPD-L1 Antibodies Enhance Tumor Cell Killing by T Cells. Two different anti-glycosylated PD-L1 antibodies generated using the method described herein were tested in a cellular cytotoxicity assay as described in Example 6 to assess the cytotoxicity of PBMC-derived T-cells against tumor cells (BT 549).
Figure 7B:
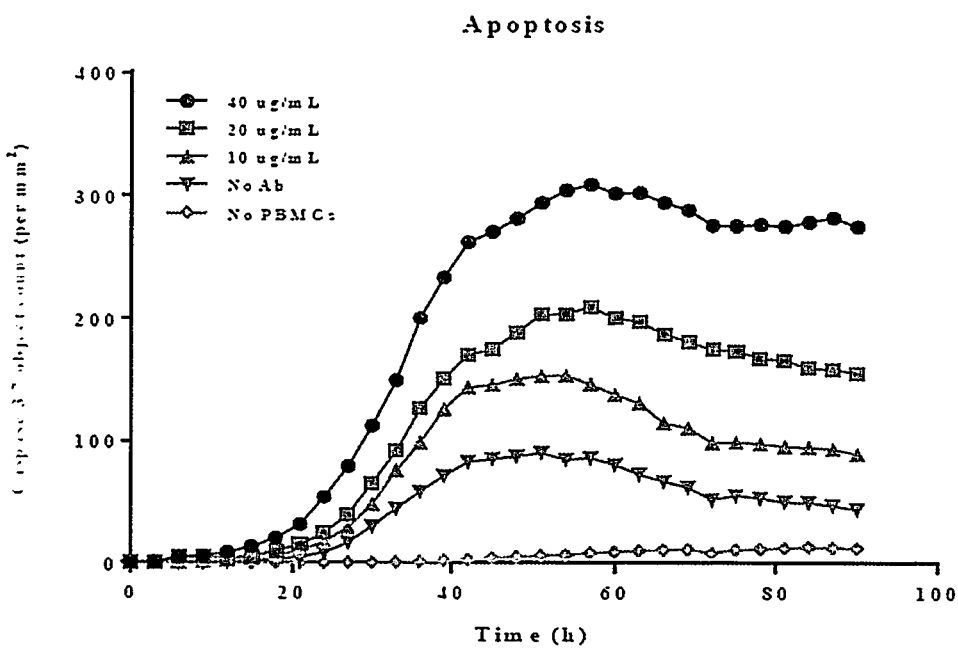

For analysis, target-cell apoptosis was quantified in the IncuCyte™ software by counting the total number of "large" green-fluorescent objects (nuclei) in the field of view over time. The proliferation of target cells was measured from the red object count, corresponding to the number of red cell nuclei. Data were expressed as the number of fluorescent objects per mm$^2$. Data showed enhancement of tumor cell killing through the addition of antibodies tested. FIG. 7A shows results for STM004 and FIG. 7B shows results for STM073.

Example 7 Binding of PD-L1 by Anti-glycPD-L1 Antibodies Promotes PD-L1 Internalization and Degradation To determine whether an anti-glycICP antibody promotes internalization and degradation following binding to its cognate ICP binding molecule, a cell staining assay was performed. In this Example, the anti-glycICP antibody used was the anti-PD-L1 MAb, STM108. For the assay, A431 cells were incubated in serum free medium overnight and then incubated with 10 μg of the anti-glycPD-L1 antibody for two days. The cells were then harvested, and PD-L1 in the cells was assessed by Western blot. Incubation of the cells with the anti-glycPD-L1 MAb showed a reduced level of PD-L1 in the cells compared to control (IgG).

The cellular internalization of STM108 MAb was visualized by labelling the antibody with pHrodo™ Red dye using the pHrodo™ Red Microscale Labeling Kit (ThermoFischer Scientific, Rochester, NY) according to the manufacturer's instructions. Briefly, for the analysis, cells were seeded at time 0; at 24 hours after seeding, cells were incubated with labeled STM108 MAb (5 μg/mL). After 1 hour, an image scan of the cells was begun using an IncuCyte ZOOM® instrument with scheduled 24-hour repeat scanning (10×) for every 1 hour. Objective: 10×; Vessel Type: Corning 356407; Scan Mode: Standard; Scan Pattern; 3 images per well; Channel: Phase+"Red."

Figure 8A:
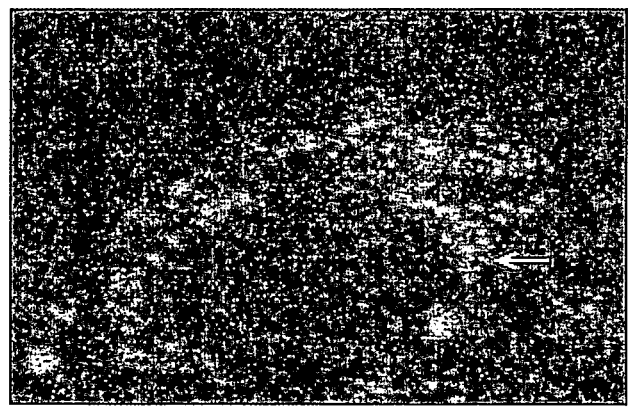
FIGS. 8A-8C. Internalization and Degradation of PD-L1 Following Binding By Anti-glycPD-L1 Antibodies.
Figure 8B:
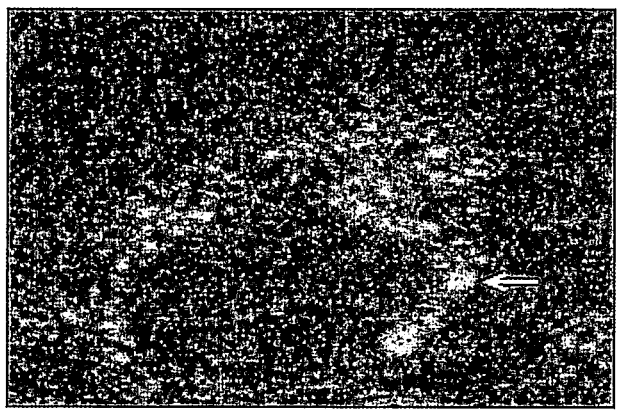
Figure 8C:

FIGS. 8A-8C provide an example of PD-L1 internalization and degradation via live cell imaging analysis following binding of anti-glycPD-L1 MAb STM108 to PD-L1 expressed on BT549-PD-L1 cells. In FIGS. 8A-8C, STM108 is conjugated to a red fluorescent dye, pHrodo™ Red (succinimidyl ester (pHrodo™ Red, SE) using the pHrodo™ Red Microscale Labeling Kit, (ThermoFisher Scientific, Rochester, NY), as described above. Green staining reflects cells stained with LysoTracker® Green DND-26, which is a cell permeable green dye that stains acidic compartments (lysosomes) in live cells imaged via live cell imaging. FIG. 8A shows that at a first time point (Time 0), the STM108 antibody is internalized into cells as observed by the intense red intracellular staining of cells indicated by the arrow. FIG. 8B shows the weakened intracellular red staining in the same cells depicted in FIG. 8A, at a time 2 minutes after Time 0 in FIG. 8A. FIG. 8C shows the lack of red intracellular staining 4 minutes after Time 0 in FIG. 8A, which reflects the degradation of the STM108 antibody and/or the antibody-antigen complex inside the cells. These images reflect that an anti-glycICP antibody, namely an anti-glycPD-L1 antibody such as STM108 MAb, effectuates internalization and degradation of PD-L1 after binding to PD-L1 expressed on the cell surface.

Example 8 Internalization of PD-L1 Bound by Anti-glycPD-L1 Antibodies in Tumor Cells Versus Total T Cells Anti-glycPD-L1 antibodies were tested for the ability to internalize into PD-L1 positive tumor cells after binding cell-surface expressed PD-L1, as compared to activated or non-activated T cells. The anti-glycPD-L1 antibodies STM004, STM073 and STM108, and mouse IgG as control were incubated with non-activated total T cells from peripheral blood, activated total T cells from peripheral blood and NCI-H226 cells, which express PD-L1. For T cell activation, total T cells were mixed with beads, e.g., inert, superparamagnetic beads, covalently coupled with anti-CD3 and anti-CD28 antibodies (e.g., ThermoFisher Scientific, Rochester, NY) at a 1:1 ratio to stimulate T cells in a manner mimics stimulation by antigen-presenting cells (See, e.g., A. Trickett et al., 2003, *J. Immunol. Methods*, 275, Issues 1-2:251-255). All antibodies were labeled with pHrodo™ Red and internalization was visualized as described above. FIGS. 9A-9D and FIGS. 9E-9H show that none of the antibodies tested were internalized into non-activated total T cells or activated total T cells. FIGS. 9I-9L show that the STM073 and STM108 MAbs were internalized into NCI- H226 cells following incubation with these cells, as evidenced by red intracellular staining, compared with the labeled control antibody, mIgG (FIG. 9I) and with labeled non-internalizing STM004 MAb. (FIG. 9J), which showed no red intracellular staining. This example demonstrates that the anti-glycPD-L1 antibodies STM073 and STM108 are examples of anti-glycICP antibodies that are selectively internalized into PD-L1-expressing tumor cells but are not internalized into either activated or non-activated T cells.

Example 9 Efficacy of PD-L1 ADC in Tumor Cell Killing and Reduction of Tumor Volume Both in vitro and in vivo experiments were conducted to evaluate the efficacy of an ADC comprising an anti-human ICP antibody, in particular, an anti-human glycPD-L1 MAb, i.e., STM108 MAb, coupled to the cytotoxin MMAE in tumor killing and in reducing tumor volume. The STM108-ADC comprises the STM108 MAb chemically linked via cysteines to MC-vc-PAB-MMAE, as described hereinabove, for specific delivery of the MMAE cytotoxin payload to PD-L1-expressing tumor or cancer cells. Measured physical properties of the STM108-ADC (STM108-MC-vc-PAB-MMAE) are as follows:

| | |
|---|---|
| $A_{248\ nm}$ of ADC | 2.548 |
| $A_{280\ nm}$ of ADC | 3.635 |
| Ratio $A_{248\ nm}/A_{280\ nm}$ | 0.70 |
| Drug Antibody Ratio | 4.13 |

Figure 10A:
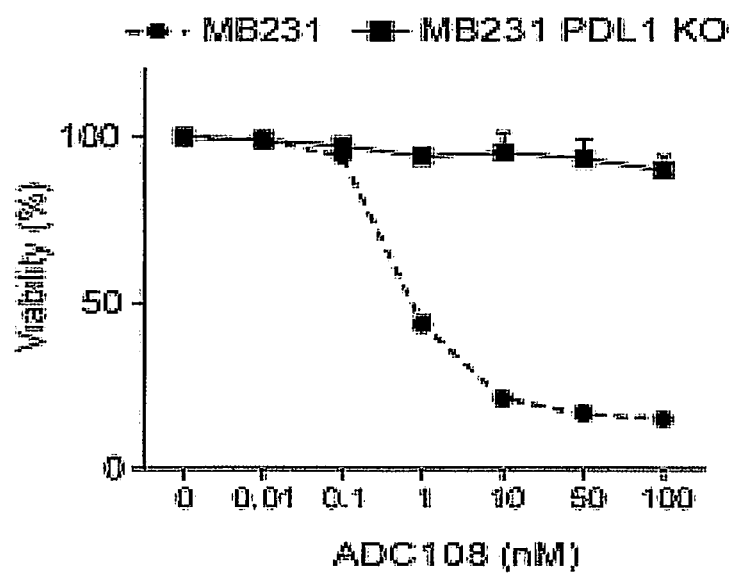
FIGS. 10A-10D Anti-tumor Efficacy of an Anti-glycPD-L1 Antibody-ADC.
Figure 10B:
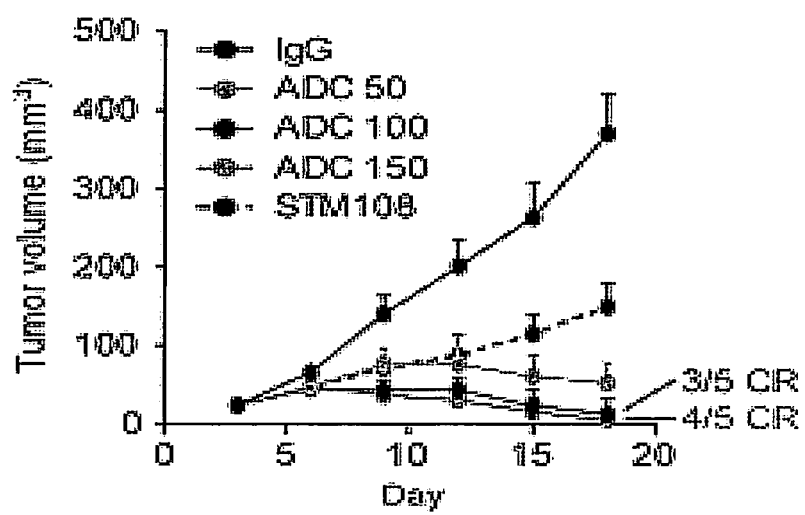

In connection with this Example, FIGS. 10A-10D present the results of experiments conducted to evaluate the efficacy of STM108-ADC in killing PD-L1-expressing and non-PD-L1-expressing tumor cells and in reducing the volume of tumors in tumor-grafted mice as compared to controls (IgG and STM108 MAb alone). FIG. 10A shows the % viability of PD-L1-expressing MDA-MB231 (human breast carcinoma cell line) tumor cells ("MB231") following exposure to different concentrations (nM) of STM108-ADC (filled black circles) compared with the % viability of MB231 cells molecularly engineered to knock out their expression of PD-L1 ("MB231 PDL1 KO") following exposure to different concentrations of STM108-ADC, i.e., "ADC108" (filled black squares). As observed, the viability of MB231 cells that did not express PD-L1 on their surface was not significantly affected by STM108-ADC at even the highest concentration, while the viability of PD-L1-expressing MB231 cells was significantly reduced, particularly at STM108-ADC concentrations of 1 nM up to 100 nM. In FIG. 10B, an MDA-MB231 mouse model of breast cancer was used in which animals grafted with tumors derived from MB231 cells were treated with either an IgG-MMAE control (100 µg); with STM108-ADC at 50 at 100 or at 150 µg; or with STM108 MAb alone (100 m). The results demonstrated that tumor volume was effectively decreased in tumor-bearing animals treated with STM108-ADC at all dose levels, as well as, to some extent, with STM108 MAb (100 m), compared with animals treated with the IgG-MMAE control. In addition, it was surprisingly found that complete remission ("CR") occurred in 3 out of 5 (3/5) animals treated with STM108-ADC (100 µg) and in 4 out of 5 (4/5) animals treated with STM108-ADC (150 µg) by about day 18.

Figure 10C:
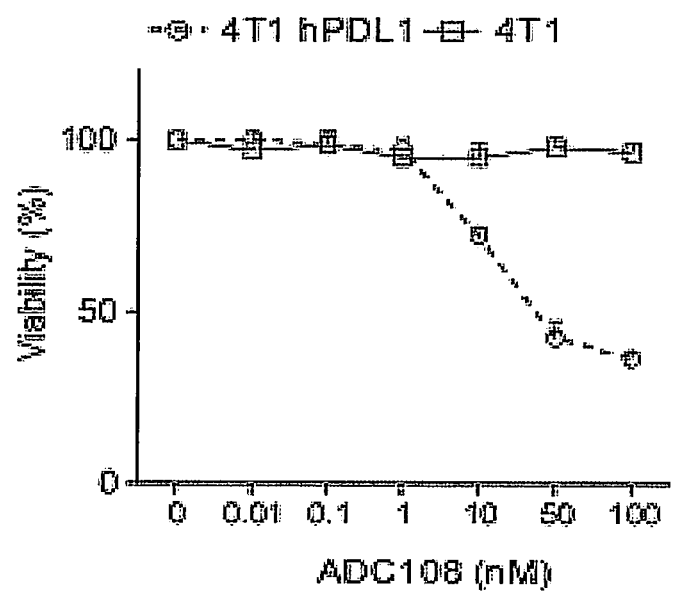

FIG. 10C shows the % viability of 4T1 mammary carcinoma cells molecularly engineered to express human PD-L1 on the cell surface ("4T1 hPDL1") following exposure to different concentrations (nM) of STM108-ADC (open red circles) compared with the % viability of 4T1 cells that naturally do not express PD-L1 ("4T1") following exposure to different concentrations of STM108-ADC, i.e., "ADC108" (open red squares). As observed, the viability of 4T1 cells that do not express PD-L1 on their surface was not significantly affected by STM108-ADC at even the highest concentration, while the viability of PD-L1-expressing 4T1 cells was reduced at STM108-ADC concentrations of greater than 10 nM to 100 nM.

4T1 syngeneic mouse models of breast cancer were used in which the animals (Balb/c mice) were grafted with tumors derived from 4T1 mammary carcinoma cells that had been molecularly engineered to express PD-L1 or the cell surface ("4T1 hPD-L1"), or in which the Balb/c mice were grafted with tumors derived from untransfected 4T1 mammary carcinoma cells that do not naturally express PD-L1 on the cell surface ("4T1"). All procedures with BALB/c mice (6- to 8-week-old females; Jackson Laboratories, Bar Harbor, Maine, USA) were conducted under guidelines approved by the Institutional Animal Care and Use Committee at MD Anderson. Mice were divided according to the mean tumor volume in each group. 4T1 cells ($1\times10^5$ cells in 25 µL of medium mixed with 25 µL of Matrixgel Basement Membrane Matrix [BD Biosciences, San Jose, CA, USA]) were injected into the mammary fat pad. IgG-MMAE control (100 µg), STM108 MAb (100 µg), or STM108-ADC (150 µg) were injected intraperitoneally on days 3, 5, 7, 9, 11, and 13 after tumor cell inoculation of mice. Tumors were measured every 3 days with a caliper, and tumor volume was calculated using the following formula: it/6×length×width.

Figure 10D:
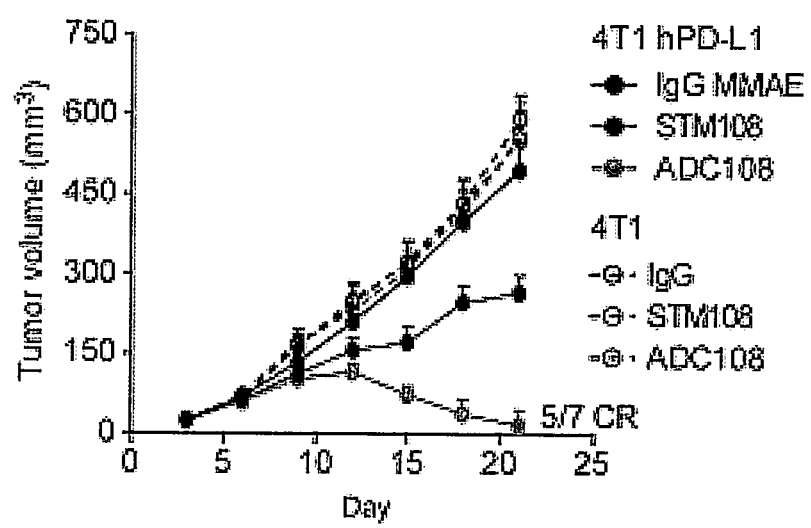

As observed in FIG. 10D, in animals harboring 4T1-derived tumors having little or no cell-surface PD-L1 expression (open circles/dotted lines), the results showed that tumor volume increased over time for all treatment types, i.e., IgG-MMAE control, STM108 MAb, or STM108-ADC. In animals harboring tumors derived from PD-L1-expressing 4T1 cells and treated with the IgG-MMAE control, tumor volume in treated animals also increased over time (solid black circles). By contrast, in animals harboring tumors derived from PD-L1-expressing 4T1 cells and treated with either the STM108 MAb (solid blue circles) or with STM108-ADC (solid red circles), tumor volume was effectively decreased. In addition, it was surprisingly found that complete remission ("CR") occurred in 5 out of 7 (5/7) animals treated with STM108-ADC by about day 21.

The beneficial and effective antineoplastic and therapeutic aspects related to the use of an ADC comprising an anti-glycICP antibody, e.g., an anti-glycPD-L1 MAb such as STM108, described hereinabove, in treating cancers, e.g., two types of breast tumors, are underscored by the in vivo results showing significant reduction in tumor volume and complete remission of tumors in animals that had been treated with the anti-glycPD-L1 MAb ADC within 25 days after treatment, e.g., by about 15-23 days.

All of the methods disclosed and claimed herein can be made and executed without undue experimentation in light of the present disclosure. While the compositions and methods have been described in terms of preferred embodiments, it will be apparent to those of skill in the art that variations may be applied to the methods and in the steps or in the sequence of steps of the methods described herein without departing from their concept, spirit and scope. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the described embodiments as defined by the appended claims.

All patents, published patent applications, and other publications cited herein are hereby incorporated by reference in the present application.

What is claimed is:

1. A method of identifying and isolating an antibody that preferentially binds a glycosylated immune checkpoint protein (ICP) antigen, said method comprising
   a) screening a population of antibodies for specific binding to a glycosylated ICP antigen;
   b) screening the antibodies that specifically bind the glycosylated ICP antigen for weaker binding to the unglycosylated form of the ICP antigen than to the glycosylated ICP antigen; and
   c) isolating an antibody that binds to the glycosylated ICP with greater affinity than to the unglycosylated form of the ICP;
   wherein the glycosylated ICP antigen is a human glycosylated ICP antigen, and
   i) wherein the human glycosylated ICP antigen is an isolated polypeptide comprising a fragment of at least 7 contiguous amino acids of human PD-L1, said polypeptide comprising at least one amino acid at position N35, N192, N200 or N219 of human PD-L1, wherein at least one of the amino acids N35, N192, N200 or N219 of PD-L1 is glycosylated, or
   ii) wherein the human glycosylated ICP antigen is an isolated polypeptide comprising a fragment of at least 7 contiguous amino acids of human PD-1, said polypeptide comprising at least one amino acid at position N49, N58, N74 or N116 of human PD-1, wherein at least one of the amino acids N49, N58, N74 or N116 of PD-1 is glycosylated.

2. The method of claim 1 wherein the population of antibodies are monoclonal antibodies obtained from an animal immunized with the glycosylated ICP antigen or peptide thereof.

3. The method of claim 1 further comprising prior to said screening step:
   a) administering to a recipient animal a glycosylated ICP antigen or peptide thereof in an effective amount to elicit a specific anti-glycosylated ICP antibody immune response in the animal;
   b) producing a population of hybridomas from said animal that secrete a population of antibodies.

4. The method of claim 2 wherein the animal is transgenic for genes that express human immunoglobulins.

5. The method of claim 1 in which the population of antibodies is a phage display antibody library or a human antibody repertoire library.

6. The method of claim 1 wherein said antibodies are tested for binding to the glycosylated ICP antigen with a $K_d$ less than half of the $K_d$ exhibited by the antibody's binding to the unglycosylated form of the ICP antigen.

7. The method of claim 1, wherein said antibodies are tested for binding to the glycosylated ICP antigen with a measured fluorescence intensity (MFI) value for binding cells expressing the glycosylated ICP antigen of at least 2-fold to 20-fold greater than the MFI value exhibited by the antibody's binding to cells expressing the unglycosylated form of the ICP antigen where the antibody is directly or indirectly labeled with a fluorescent label.

8. The method of claim 1, wherein the glycosylated ICP antigen or peptide thereof is expressed on a tumor or cancer cell, and the ICP ligand is expressed on an immune cell or wherein the glycosylated ICP antigen or peptide thereof is expressed on an immune cell, and the ICP ligand is expressed on a tumor or cancer cell.

9. The method of claim 8, wherein the immune cell is an effector T cell or a natural killer cell (NK cell).

10. The method of claim 1, which further comprises testing the antibody for inhibiting binding of the ICP to its cognate ICP binding partner.

11. The method of claim 1, further comprising identifying the amino acids comprising complementarity determining regions (CDRs) of the antibody and humanizing the amino acid sequences surrounding the CDRs to produce a humanized antibody.

12. The method of claim 1, wherein the human glycosylated ICP antigen is human PD-L1, wherein at least one of the amino acids corresponding to position N35, N192, or N200 of PD-L1 is glycosylated.

13. The method of claim 1, wherein the human glycosylated ICP antigen is human PD-1, wherein at least one of the amino acids corresponding to position N49, N58, N74 or N116 of PD-1 is glycosylated.

14. The method of claim 1, which further comprises linking an scFv containing the antigen binding domain of a second antibody that binds an epitope of the human glycosylated ICP that does not overlap with the epitope of said antibody to the N-terminus of the heavy chain and/or light chain of said antibody.

15. The method of claim 1, wherein said antibodies are tested for binding to the glycosylated ICP antigen with a Kd less than 20% of the Kd exhibited by the antibody's binding to the unglycosylated form of the ICP antigen.

16. The method of claim 1, wherein the human glycosylated ICP antigen is an isolated polypeptide comprising an extracellular domain of human PD-1, wherein position N58 of PD-1 is glycosylated.

17. The method of claim 1, wherein screening a population of antibodies for specific binding to a glycosylated ICP antigen comprises screening a population of antibodies for specific binding to an ICP antigen glycosylated at N35, N192, and N200 of human PD-L1.

18. The method of claim 1, wherein screening a population of antibodies for specific binding to a glycosylated ICP antigen comprises screening a population of antibodies for specific binding to an ICP antigen glycosylated at N200 of human PD-L1.

19. The method of claim 1, wherein screening a population of antibodies for specific binding to a glycosylated ICP antigen comprises screening a population of antibodies for specific binding to an ICP antigen glycosylated at N35 of human PD-L1.

20. The method of claim 1, wherein screening a population of antibodies for specific binding to a glycosylated ICP antigen comprises screening a population of antibodies for specific binding to an ICP antigen glycosylated at N192 of human PD-L1.

21. The method of claim 1, wherein the glycosylated ICP antigen is a normally expressed, human antigen.

22. The method of claim 1, wherein the glycosylated ICP antigen is expressed on a cancer cell.

* * * * *

SEQUENCE LISTING

<160> NUMBER OF SEQ ID NOS: 19

<210> SEQ ID NO 1
<211> LENGTH: 290
<212> TYPE: PRT
<213> ORGANISM: Homo sapiens

<400> SEQUENCE: 1

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
290

<210> SEQ ID NO 2
<211> LENGTH: 288
<212> TYPE: PRT
<213> ORGANISM: Homo sapiens

<400> SEQUENCE: 2

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp

```
                20                  25                  30
Asn Pro Pro Thr Phe Ser Pro Ala Leu Leu Val Val Thr Glu Gly Asp
            35                  40                  45
Asn Ala Thr Phe Thr Cys Ser Phe Ser Asn Thr Ser Glu Ser Phe Val
50                  55                  60
Leu Asn Trp Tyr Arg Met Ser Pro Ser Asn Gln Thr Asp Lys Leu Ala
65                  70                  75                  80
Ala Phe Pro Glu Asp Arg Ser Gln Pro Gly Gln Asp Cys Arg Phe Arg
                85                  90                  95
Val Thr Gln Leu Pro Asn Gly Arg Asp Phe His Met Ser Val Val Arg
            100                 105                 110
Ala Arg Arg Asn Asp Ser Gly Thr Tyr Leu Cys Gly Ala Ile Ser Leu
        115                 120                 125
Ala Pro Lys Ala Gln Ile Lys Glu Ser Leu Arg Ala Glu Leu Arg Val
    130                 135                 140
Thr Glu Arg Arg Ala Glu Val Pro Thr Ala His Pro Ser Pro Ser Pro
145                 150                 155                 160
Arg Pro Ala Gly Gln Phe Gln Thr Leu Val Val Gly Val Val Gly Gly
                165                 170                 175
Leu Leu Gly Ser Leu Val Leu Leu Val Trp Val Leu Ala Val Ile Cys
            180                 185                 190
Ser Arg Ala Ala Arg Gly Thr Ile Gly Ala Arg Arg Thr Gly Gln Pro
        195                 200                 205
Leu Lys Glu Asp Pro Ser Ala Val Pro Val Phe Ser Val Asp Tyr Gly
    210                 215                 220
Glu Leu Asp Phe Gln Trp Arg Glu Lys Thr Pro Glu Pro Pro Val Pro
225                 230                 235                 240
Cys Val Pro Glu Gln Thr Glu Tyr Ala Thr Ile Val Phe Pro Ser Gly
                245                 250                 255
Met Gly Thr Ser Ser Pro Ala Arg Arg Gly Ser Ala Asp Gly Pro Arg
            260                 265                 270
Ser Ala Gln Pro Leu Arg Pro Glu Asp Gly His Cys Ser Trp Pro Leu
        275                 280                 285

<210> SEQ ID NO 3
<211> LENGTH: 289
<212> TYPE: PRT
<213> ORGANISM: Homo sapiens

<400> SEQUENCE: 3

Met Lys Thr Leu Pro Ala Met Leu Gly Thr Gly Lys Leu Phe Trp Val
1               5                   10                  15
Phe Phe Leu Ile Pro Tyr Leu Asp Ile Trp Asn Ile His Gly Lys Glu
            20                  25                  30
Ser Cys Asp Val Gln Leu Tyr Ile Lys Arg Gln Ser Glu His Ser Ile
        35                  40                  45
Leu Ala Gly Asp Pro Phe Glu Leu Glu Cys Pro Val Lys Tyr Cys Ala
    50                  55                  60
Asn Arg Pro His Val Thr Trp Cys Lys Leu Asn Gly Thr Thr Cys Val
65                  70                  75                  80
Lys Tyr Leu Glu Arg Gln Thr Ser Trp Lys Glu Lys Asn Ile Ser
                85                  90                  95
Phe Phe Ile Leu His Phe Glu Pro Val Leu Pro Asn Asp Asn Gly Ser
            100                 105                 110
```

```
Tyr Arg Cys Ser Ala Asn Phe Gln Ser Asn Leu Ile Glu Ser His Ser
            115                 120                 125

Thr Thr Leu Tyr Val Thr Asp Val Lys Ser Ala Ser Glu Arg Pro Ser
            130                 135                 140

Lys Asp Glu Met Ala Ser Arg Pro Trp Leu Leu Tyr Arg Leu Leu Pro
145                 150                 155                 160

Leu Gly Gly Leu Pro Leu Leu Ile Thr Thr Cys Phe Cys Leu Phe Cys
                165                 170                 175

Cys Leu Arg Arg His Gln Gly Lys Gln Asn Glu Leu Ser Asp Thr Ala
            180                 185                 190

Gly Arg Glu Ile Asn Leu Val Asp Ala His Leu Lys Ser Glu Gln Thr
            195                 200                 205

Glu Ala Ser Thr Arg Gln Asn Ser Gln Val Leu Leu Ser Glu Thr Gly
            210                 215                 220

Ile Tyr Asp Asn Asp Pro Asp Leu Cys Phe Arg Met Gln Glu Gly Ser
225                 230                 235                 240

Glu Val Tyr Ser Asn Pro Cys Leu Glu Glu Asn Lys Pro Gly Ile Val
                245                 250                 255

Tyr Ala Ser Leu Asn His Ser Val Ile Gly Pro Asn Ser Arg Leu Ala
            260                 265                 270

Arg Asn Val Lys Glu Ala Pro Thr Glu Tyr Ala Ser Ile Cys Val Arg
            275                 280                 285

Ser

<210> SEQ ID NO 4
<211> LENGTH: 187
<212> TYPE: PRT
<213> ORGANISM: Homo sapiens

<400> SEQUENCE: 4

Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
                20                  25                  30

Gly Lys Gly Ala Cys Pro Val Phe Glu Cys Gly Asn Val Val Leu Arg
            35                  40                  45

Thr Asp Glu Arg Asp Val Asn Tyr Trp Thr Ser Arg Tyr Trp Leu Asn
50                  55                  60

Gly Asp Phe Arg Lys Gly Asp Val Ser Leu Thr Ile Glu Asn Val Thr
65                  70                  75                  80

Leu Ala Asp Ser Gly Ile Tyr Cys Cys Arg Ile Gln Ile Pro Gly Ile
                85                  90                  95

Met Asn Asp Glu Lys Phe Asn Leu Lys Leu Val Ile Lys Pro Ala Lys
            100                 105                 110

Val Thr Pro Ala Pro Thr Leu Gln Arg Asp Phe Thr Ala Ala Phe Pro
            115                 120                 125

Arg Met Leu Thr Thr Arg Gly His Gly Pro Ala Glu Thr Gln Thr Leu
130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175

Thr Ile Arg Val Asp His His His His His
            180                 185
```

<210> SEQ ID NO 5
<211> LENGTH: 412
<212> TYPE: PRT
<213> ORGANISM: Homo sapiens

<400> SEQUENCE: 5

```
Leu Gln Pro Gly Ala Glu Val Pro Val Val Trp Ala Gln Glu Gly Ala
 1               5                  10                  15
Pro Ala Gln Leu Pro Cys Ser Pro Thr Ile Pro Leu Gln Asp Leu Ser
            20                  25                  30
Leu Leu Arg Arg Ala Gly Val Thr Trp Gln His Gln Pro Asp Ser Gly
        35                  40                  45
Pro Pro Ala Ala Ala Pro Gly His Pro Leu Ala Pro Gly Pro His Pro
    50                  55                  60
Ala Ala Pro Ser Ser Trp Gly Pro Arg Pro Arg Arg Tyr Thr Val Leu
65                  70                  75                  80
Ser Val Gly Pro Gly Gly Leu Arg Ser Gly Arg Leu Pro Leu Gln Pro
                85                  90                  95
Arg Val Gln Leu Asp Glu Arg Gly Arg Gln Arg Gly Asp Phe Ser Leu
            100                 105                 110
Trp Leu Arg Pro Ala Arg Arg Ala Asp Ala Gly Glu Tyr Arg Ala Ala
        115                 120                 125
Val His Leu Arg Asp Arg Ala Leu Ser Cys Arg Leu Arg Leu Arg Leu
    130                 135                 140
Gly Gln Ala Ser Met Thr Ala Ser Pro Pro Gly Ser Leu Arg Ala Ser
145                 150                 155                 160
Asp Trp Val Ile Leu Asn Cys Ser Phe Ser Arg Pro Asp Arg Pro Ala
                165                 170                 175
Ser Val His Trp Phe Arg Asn Arg Gly Gln Gly Arg Val Pro Val Arg
            180                 185                 190
Glu Ser Pro His His His Leu Ala Glu Ser Phe Leu Phe Leu Pro Gln
        195                 200                 205
Val Ser Pro Met Asp Ser Gly Pro Trp Gly Cys Ile Leu Thr Tyr Arg
    210                 215                 220
Asp Gly Phe Asn Val Ser Ile Met Tyr Asn Leu Thr Val Leu Gly Leu
225                 230                 235                 240
Glu Pro Pro Thr Pro Leu Thr Val Tyr Ala Gly Ala Gly Ser Arg Val
                245                 250                 255
Gly Leu Pro Cys Arg Leu Pro Ala Gly Val Gly Thr Arg Ser Phe Leu
            260                 265                 270
Thr Ala Lys Trp Thr Pro Pro Gly Gly Gly Pro Asp Leu Leu Val Thr
        275                 280                 285
Gly Asp Asn Gly Asp Phe Thr Leu Arg Leu Glu Asp Val Ser Gln Ala
    290                 295                 300
Gln Ala Gly Thr Tyr Thr Cys His Ile His Leu Gln Glu Gln Gln Leu
305                 310                 315                 320
Asn Ala Thr Val Thr Leu Ala Ile Ile Thr Val Thr Pro Lys Ser Phe
                325                 330                 335
Gly Ser Pro Gly Ser Leu Gly Lys Leu Leu Cys Glu Val Thr Pro Val
            340                 345                 350
Ser Gly Gln Glu Arg Phe Val Trp Ser Ser Leu Asp Thr Pro Ser Gln
        355                 360                 365
Arg Ser Phe Ser Gly Pro Trp Leu Glu Ala Gln Glu Ala Gln Leu Leu
    370                 375                 380
```

-continued

Ser Gln Pro Trp Gln Cys Gln Leu Tyr Gln Gly Glu Arg Leu Leu Gly
385                 390                 395                 400

Ala Ala Val Tyr Phe Thr Glu Leu Ser Ser Pro Gly
            405                 410

<210> SEQ ID NO 6
<211> LENGTH: 526
<212> TYPE: PRT
<213> ORGANISM: Homo sapiens

<400> SEQUENCE: 6

Met Ala Val Phe Pro Ser Ser Gly Leu Pro Arg Cys Leu Leu Thr Leu
1               5                   10                  15

Ile Leu Leu Gln Leu Pro Lys Leu Asp Ser Ala Pro Phe Asp Val Ile
            20                  25                  30

Gly Pro Pro Glu Pro Ile Leu Ala Val Val Gly Glu Asp Ala Lys Leu
        35                  40                  45

Pro Cys Arg Leu Ser Pro Asn Ala Ser Ala Glu His Leu Glu Leu Arg
50                  55                  60

Trp Phe Arg Lys Lys Val Ser Pro Ala Val Leu Val His Arg Asp Gly
65                  70                  75                  80

Arg Glu Gln Glu Ala Glu Gln Met Pro Glu Tyr Arg Gly Arg Ala Thr
                85                  90                  95

Leu Val Gln Asp Gly Ile Ala Lys Gly Arg Val Ala Leu Arg Ile Arg
            100                 105                 110

Gly Val Arg Val Ser Asp Asp Gly Glu Tyr Thr Cys Phe Phe Arg Glu
        115                 120                 125

Asp Gly Ser Tyr Glu Glu Ala Leu Val His Leu Lys Val Ala Ala Leu
130                 135                 140

Gly Ser Asp Pro His Ile Ser Met Gln Val Gln Glu Asn Gly Glu Ile
145                 150                 155                 160

Cys Leu Glu Cys Thr Ser Val Gly Trp Tyr Pro Glu Pro Gln Val Gln
                165                 170                 175

Trp Arg Thr Ser Lys Gly Glu Lys Phe Pro Ser Thr Ser Glu Ser Arg
            180                 185                 190

Asn Pro Asp Glu Glu Gly Leu Phe Thr Val Ala Ala Ser Val Ile Ile
        195                 200                 205

Arg Asp Thr Ser Ala Lys Asn Val Ser Cys Tyr Ile Gln Asn Leu Leu
210                 215                 220

Leu Gly Gln Glu Lys Lys Val Glu Ile Ser Ile Pro Ala Ser Ser Leu
225                 230                 235                 240

Pro Arg Leu Thr Pro Trp Ile Val Ala Val Ala Val Ile Leu Met Val
                245                 250                 255

Leu Gly Leu Leu Thr Ile Gly Ser Ile Phe Phe Thr Trp Arg Leu Tyr
            260                 265                 270

Asn Glu Arg Pro Arg Glu Arg Asn Glu Phe Ser Ser Lys Glu Arg
        275                 280                 285

Leu Leu Glu Glu Leu Lys Trp Lys Lys Ala Thr Leu His Ala Val Asp
290                 295                 300

Val Thr Leu Asp Pro Asp Thr Ala His Pro His Leu Phe Leu Tyr Glu
305                 310                 315                 320

Asp Ser Lys Ser Val Arg Leu Glu Asp Ser Arg Gln Lys Leu Pro Glu
                325                 330                 335

Lys Thr Glu Arg Phe Asp Ser Trp Pro Cys Val Leu Gly Arg Glu Thr

```
                340                 345                 350
Phe Thr Ser Gly Arg His Tyr Trp Glu Val Glu Val Gly Asp Arg Thr
            355                 360                 365
Asp Trp Ala Ile Gly Val Cys Arg Glu Asn Val Met Lys Lys Gly Phe
        370                 375                 380
Asp Pro Met Thr Pro Glu Asn Gly Phe Trp Ala Val Glu Leu Tyr Gly
385                 390                 395                 400
Asn Gly Tyr Trp Ala Leu Thr Pro Leu Arg Thr Pro Leu Pro Leu Ala
                405                 410                 415
Gly Pro Pro Arg Arg Val Gly Ile Phe Leu Asp Tyr Glu Ser Gly Asp
            420                 425                 430
Ile Ser Phe Tyr Asn Met Asn Asp Gly Ser Asp Ile Tyr Thr Phe Ser
        435                 440                 445
Asn Val Thr Phe Ser Gly Pro Leu Arg Pro Phe Phe Cys Leu Trp Ser
    450                 455                 460
Ser Gly Lys Lys Pro Leu Thr Ile Cys Pro Ile Ala Asp Gly Pro Glu
465                 470                 475                 480
Arg Val Thr Val Ile Ala Asn Ala Gln Asp Leu Ser Lys Glu Ile Pro
                485                 490                 495
Leu Ser Pro Met Gly Glu Asp Ser Ala Pro Arg Asp Ala Asp Thr Leu
            500                 505                 510
His Ser Lys Leu Ile Pro Thr Gln Pro Ser Gln Gly Ala Pro
        515                 520                 525

<210> SEQ ID NO 7
<211> LENGTH: 468
<212> TYPE: PRT
<213> ORGANISM: Homo sapiens

<400> SEQUENCE: 7

Met Gly His Leu Ser Ala Pro Leu His Arg Val Arg Val Pro Trp Gln
1               5                   10                  15
Gly Leu Leu Leu Thr Ala Ser Leu Leu Thr Phe Trp Asn Pro Pro Thr
            20                  25                  30
Thr Ala Gln Leu Thr Thr Glu Ser Met Pro Phe Asn Val Ala Glu Gly
        35                  40                  45
Lys Glu Val Leu Leu Leu Val His Asn Leu Pro Gln Gln Leu Phe Gly
    50                  55                  60
Tyr Ser Trp Tyr Lys Gly Glu Arg Val Asp Gly Asn Arg Gln Ile Val
65                  70                  75                  80
Gly Tyr Ala Ile Gly Thr Gln Gln Ala Thr Pro Gly Pro Ala Asn Ser
                85                  90                  95
Gly Arg Glu Thr Ile Tyr Pro Asn Ala Ser Leu Leu Ile Gln Asn Val
            100                 105                 110
Thr Gln Asn Asp Thr Gly Phe Tyr Thr Leu Gln Val Ile Lys Ser Asp
        115                 120                 125
Leu Val Asn Glu Glu Ala Thr Gly Gln Phe His Val Tyr Pro Glu Leu
    130                 135                 140
Pro Lys Pro Ser Ile Ser Ser Asn Asn Ser Asn Pro Val Glu Asp Lys
145                 150                 155                 160
Asp Ala Val Ala Phe Thr Cys Glu Pro Glu Thr Gln Asp Thr Thr Tyr
                165                 170                 175
Leu Trp Trp Ile Asn Asn Gln Ser Leu Pro Val Ser Pro Arg Leu Gln
            180                 185                 190
```

-continued

```
Leu Ser Asn Gly Asn Arg Thr Leu Thr Leu Leu Ser Val Thr Arg Asn
            195                 200                 205

Asp Thr Gly Pro Tyr Glu Cys Glu Ile Gln Asn Pro Val Ser Ala Asn
210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Thr Cys His Ala Asn Asn Ser
    290                 295                 300

Val Thr Gly Cys Asn Arg Thr Thr Val Lys Thr Ile Ile Val Thr Glu
305                 310                 315                 320

Leu Ser Pro Val Val Ala Lys Pro Gln Ile Lys Ala Ser Lys Thr Thr
                325                 330                 335

Val Thr Gly Asp Lys Asp Ser Val Asn Leu Thr Cys Ser Thr Asn Asp
            340                 345                 350

Thr Gly Ile Ser Ile Arg Trp Phe Phe Lys Asn Gln Ser Leu Pro Ser
        355                 360                 365

Ser Glu Arg Met Lys Leu Ser Gln Gly Asn Thr Thr Leu Ser Ile Asn
    370                 375                 380

Pro Val Lys Arg Glu Asp Ala Gly Thr Tyr Trp Cys Glu Val Phe Asn
385                 390                 395                 400

Pro Ile Ser Lys Asn Gln Ser Asp Pro Ile Met Leu Asn Val Asn Tyr
                405                 410                 415

Asn Ala Leu Pro Gln Glu Asn Gly Leu Ser Pro Gly Ala Ile Ala Gly
            420                 425                 430

Ile Val Ile Gly Val Val Ala Leu Val Ala Leu Ile Ala Val Ala Leu
        435                 440                 445

Ala Cys Phe Leu His Phe Gly Lys Thr Gly Arg Thr Thr Pro Met Thr
    450                 455                 460

His Leu Thr Arg
465

<210> SEQ ID NO 8
<211> LENGTH: 862
<212> TYPE: PRT
<213> ORGANISM: Homo sapiens

<400> SEQUENCE: 8

Met Arg Met Cys Thr Pro Ile Arg Gly Leu Leu Met Ala Leu Ala Val
1               5                   10                  15

Met Phe Gly Thr Ala Met Ala Phe Ala Pro Ile Pro Arg Ile Thr Trp
            20                  25                  30

Glu His Arg Glu Val His Leu Val Gln Phe His Glu Pro Asp Ile Tyr
        35                  40                  45

Asn Tyr Ser Ala Leu Leu Leu Ser Glu Asp Lys Asp Thr Leu Tyr Ile
    50                  55                  60

Gly Ala Arg Glu Ala Val Phe Ala Val Asn Ala Leu Asn Ile Ser Glu
65                  70                  75                  80

Lys Gln His Glu Val Tyr Trp Lys Val Ser Glu Asp Lys Lys Ala Lys
                85                  90                  95
```

-continued

Cys Ala Glu Lys Gly Lys Ser Lys Gln Thr Glu Cys Leu Asn Tyr Ile
            100                 105                 110

Arg Val Leu Gln Pro Leu Ser Ala Thr Ser Leu Tyr Val Cys Gly Thr
            115                 120                 125

Asn Ala Phe Gln Pro Ala Cys Asp His Leu Asn Leu Thr Ser Phe Lys
            130                 135                 140

Phe Leu Gly Lys Asn Glu Asp Gly Lys Gly Arg Cys Pro Phe Asp Pro
145                 150                 155                 160

Ala His Ser Tyr Thr Ser Val Met Val Asp Gly Glu Leu Tyr Ser Gly
                    165                 170                 175

Thr Ser Tyr Asn Phe Leu Gly Ser Glu Pro Ile Ile Ser Arg Asn Ser
            180                 185                 190

Ser His Ser Pro Leu Arg Thr Glu Arg Ala Ala Asn Tyr Thr Ser Ser
            195                 200                 205

Leu Asn Leu Pro Asp Lys Thr Leu Gln Phe Val Lys Asp His Pro Leu
            210                 215                 220

Met Ser His Thr Lys Trp Val Arg Tyr Asn Gly Pro Val Pro Lys Pro
225                 230                 235                 240

Arg Pro Gly Ala Cys Ile Asp Ser Glu Ala Cys Ala Tyr Asn Leu Ser
                    245                 250                 255

Thr Ala Glu Glu Val Phe Ser His Gly Lys Tyr Met Gln Ser Thr Thr
            260                 265                 270

Val Glu Gln Ser Pro Gly Leu Lys Val Pro Val Phe Tyr Ala Leu Phe
            275                 280                 285

Thr Pro Gln Leu Asn Asn Val Gly Leu Ser Ala Val Lys Ala Arg Leu
            290                 295                 300

Ile Cys Ser Arg Pro Asp Ser Gly Leu Val Phe Asn Val Leu Arg Asp
305                 310                 315                 320

Val Phe Val Leu Arg Pro Arg Ile Ala Arg Val Cys Lys Gly Asp Gln
                    325                 330                 335

Gly Gly Leu Arg Thr Leu Gln Lys Lys Trp Thr Ser Phe Leu Gly Glu
            340                 345                 350

Asp Asp Arg Val Tyr Phe Phe Thr Glu Val Ser Val Glu Tyr Glu
            355                 360                 365

Phe Val Phe Arg Val Leu Ile Tyr Ala Ile Pro Trp Leu Asn Glu Pro
            370                 375                 380

Ser Phe Val Phe Ala Asp Val Ile Arg Lys Ser Pro Asp Ser Pro Asp
385                 390                 395                 400

Asp Asp Ser Val Thr Pro Ile Asp Asn Arg Pro Arg Leu Ile Lys Lys
                    405                 410                 415

Asp Val Asn Tyr Thr Gln Ile Val Asp Arg Thr Gln Ala Leu Asp
            420                 425                 430

Gly Thr Val Tyr Asp Val Met Phe Val Ser Thr Asp Arg Gly Ala Leu
            435                 440                 445

His Lys Ala Ile Ser Leu Glu His Ala Val His Ile Ile Glu Glu Thr
            450                 455                 460

Gln Leu Phe Gln Asp Phe Glu Pro Val Gln Thr Leu Leu Ser Ser
465                 470                 475                 480

Lys Lys Gly Asn Arg Phe Val Tyr Ala Gly Ser Asn Ser Gly Val Val
                    485                 490                 495

Gln Ala Pro Leu Ala Phe Cys Gly Lys His Gly Thr Cys Glu Asp Cys
            500                 505                 510

Val Leu Ala Arg Asp Pro Tyr Cys Ala Trp Ser Pro Thr Ala Thr
515                 520                 525

Cys Val Ala Leu His Gln Thr Glu Ser Pro Ser Arg Gly Leu Ile Gln
530                 535                 540

Glu Met Ser Gly Asp Ala Ser Val Cys Pro Asp Lys Ser Lys Gly Ser
545                 550                 555                 560

Tyr Arg Gln His Phe Phe Lys His Gly Gly Thr Ala Glu Leu Lys Cys
                565                 570                 575

Ser Gln Lys Ser Asn Leu Ala Arg Val Phe Trp Lys Phe Gln Asn Asp
            580                 585                 590

Val Leu Lys Ala Glu Ser Pro Lys Tyr Gly Leu Met Gly Arg Lys Asn
        595                 600                 605

Leu Leu Ile Phe Asn Leu Ser Glu Gly Asp Ser Gly Val Tyr Gln Cys
    610                 615                 620

Leu Ser Glu Glu Arg Val Lys Asn Lys Thr Val Phe Gln Val Val Ala
625                 630                 635                 640

Lys His Val Leu Glu Val Lys Val Val Pro Lys Pro Val Ala Pro
                645                 650                 655

Thr Leu Ser Val Val Gln Thr Glu Gly Ser Arg Ile Ala Thr Lys Val
                660                 665                 670

Leu Val Ala Ser Thr Gln Gly Ser Ser Pro Pro Thr Pro Ala Val Gln
            675                 680                 685

Ala Thr Ser Ser Gly Ala Ile Thr Leu Pro Pro Lys Pro Ala Pro Thr
        690                 695                 700

Gly Thr Ser Cys Glu Pro Lys Ile Val Ile Asn Thr Val Pro Gln Leu
705                 710                 715                 720

His Ser Glu Lys Thr Met Tyr Leu Lys Ser Ser Asp Asn Arg Leu Leu
                725                 730                 735

Met Ser Leu Phe Leu Phe Phe Val Leu Phe Leu Cys Leu Phe Phe
                740                 745                 750

Tyr Asn Cys Tyr Lys Gly Tyr Leu Pro Arg Gln Cys Leu Lys Phe Arg
            755                 760                 765

Ser Ala Leu Leu Ile Gly Lys Lys Pro Lys Ser Asp Phe Cys Asp
770                 775                 780

Arg Glu Gln Ser Leu Lys Glu Thr Leu Val Glu Pro Gly Ser Phe Ser
785                 790                 795                 800

Gln Gln Asn Gly Glu His Pro Lys Pro Ala Leu Asp Thr Gly Tyr Glu
                805                 810                 815

Thr Glu Gln Asp Thr Ile Thr Ser Lys Val Pro Thr Ala Arg Glu Asp
            820                 825                 830

Ser Gln Arg Ile Asp Asp Leu Ser Ala Arg Asp Lys Pro Phe Asp Val
        835                 840                 845

Lys Cys Glu Leu Lys Phe Ala Asp Ser Asp Ala Asp Gly Asp
850                 855                 860

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tcaattgtca tattgctac                                                    19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ttgactccat ctttcttca                                             19

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtggtagagt atggtagcca aatgacaatt gaatgcaaa                       39

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tttgcattca attgtcattt ggctaccata ctctaccac                       39

<210> SEQ ID NO 13
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gagaggagaa gcttttccag gtgaccagca cactgag                         37

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctcagtgtgc tggtcacctg gaaaagcttc tcctctc                         37

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gaccagcaca ctgagaatcc agacaacaac taatgagat                       39

```
<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atctcattag ttgttgtctg gattctcagt gtgctggtc                              39

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gagagaggag aagcttttcc aagtgaccag cacactgaga                             40

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tctcagtgtg ctggtcactt ggaaaagctt ctcctctctc                             40

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 19

His His His His His His
1               5
```